US012774446B2

(12) United States Patent
Ludlam et al.

(10) Patent No.: US 12,774,446 B2
(45) **Date of Patent: *Oct. 27, 2026**

(54) MICROFLUIDIC-ENABLED MULTIWELL CELL CULTURE DEVICES AND SYSTEMS FOR PRECISION CULTURE, CONTROL AND MONITORING OF LIVING CELLS

(71) Applicants: Cairn Biosciences, Inc., San Francisco, CA (US); The Regents of the University of California, Oakland, CA (US)

(72) Inventors: Mary J. C. Ludlam, San Francisco, CA (US); Austin Blanco, Lincoln, CA (US); David Wartmann, Berkeley, CA (US); Richard A. Mathies, Walnut Creek, CA (US)

(73) Assignees: The Regents of the University of California, Oakland, CA (US); Cairn Biosciences, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/623,528

(22) Filed: Apr. 1, 2024

(65) Prior Publication Data

US 2024/0327776 A1 Oct. 3, 2024

Related U.S. Application Data

(63) Continuation of application No. 16/614,290, filed as application No. PCT/US2018/032838 on May 15, 2018, now Pat. No. 11,946,035.

(Continued)

(51) Int. Cl.

*C12M 3/06* (2006.01)
*C12M 1/00* (2006.01)

(Continued)

(52) U.S. Cl.

CPC ............ *C12M 41/48* (2013.01); *C12M 23/12* (2013.01); *C12M 23/16* (2013.01); *C12M 29/00* (2013.01);

(Continued)

(58) Field of Classification Search

CPC .............................. C12M 23/16; C12M 41/48

See application file for complete search history.

(56) References Cited

U.S. PATENT DOCUMENTS

| | | | |
|---|---|---|---|
| 11,946,035 | B2 | 4/2024 | Ludlam |
| 2005/0266393 | A1 | 12/2005 | Baxter et al. |

(Continued)

FOREIGN PATENT DOCUMENTS

| | | | |
|---|---|---|---|
| CN | 1369039 | A | 9/2002 |
| CN | 1630707 | A | 6/2005 |

(Continued)

OTHER PUBLICATIONS

El-Ali, J. et al. (Jul. 27, 2006). "Cells on Chips," Nature 442:403-411.

(Continued)

*Primary Examiner* — Jonathan M Hurst

(74) *Attorney, Agent, or Firm* — Morrison & Foerster LLP

(57) ABSTRACT

Devices, systems, methods, and techniques regarding a microfluidic-enabled multiwell device with closed-loop monitoring and control of various parameters of the microfluidic environment are provided. A microfluidic-enabled multiwell device may have a removable and disposable microfluidics module layer and a reusable sensor module layer. The sensor module layer may be configured to monitor and control parameters of the environment inside the microfluidics module layer, store data regarding the parameters, and wirelessly transmit the data. The device may be con- (Continued)

figured to individually address flow of fluid to any one of a plurality of wells, using one or more pneumatic micro-pumps. The device may be configured to automatically execute one or more live cell cultures, assays, and/or protocols. The device may be configured to be received in a docking station and/or portable manifold adapter, and to be fluidly, pneumatically, and/or electronically coupled to the station, adapter, or other laboratory equipment.

49 Claims, 41 Drawing Sheets

Related U.S. Application Data

(60) Provisional application No. 62/507,139, filed on May 16, 2017.

(51) Int. Cl.

| | |
|---|---|
| ***C12M 1/32*** | (2006.01) |
| ***C12M 1/34*** | (2006.01) |
| ***C12M 1/36*** | (2006.01) |
| *G06F 3/0481* | (2022.01) |

(52) U.S. Cl.

CPC ............ *C12M 29/20* (2013.01); *C12M 41/44* (2013.01); *G06F 3/0481* (2013.01)

(56) References Cited

U.S. PATENT DOCUMENTS

| | | | |
|---|---|---|---|
| 2006/0199260 | A1 | 9/2006 | Sinskey |
| 2006/0234298 | A1 | 10/2006 | Chiu et al. |
| 2007/0166199 | A1* | 7/2007 | Zhou ................. B01L 3/502738 422/400 |
| 2007/0275455 | A1 | 11/2007 | Hung et al. |
| 2012/0245042 | A1 | 9/2012 | Liu et al. |
| 2013/0337565 | A1 | 12/2013 | Banes et al. |
| 2014/0356849 | A1 | 12/2014 | Wikswo et al. |
| 2016/0263572 | A1 | 9/2016 | Gaige et al. |
| 2017/0081625 | A1 | 3/2017 | Wikswo |
| 2019/0330579 | A1* | 10/2019 | Guenat .................. C12M 25/02 |
| 2021/0002602 | A1 | 1/2021 | Ludlam et al. |

FOREIGN PATENT DOCUMENTS

| | | | |
|---|---|---|---|
| CN | 1778900 | A | 5/2006 |
| CN | 101198688 | A | 6/2008 |
| CN | 101506643 | A | 8/2009 |
| CN | 101715483 | A | 5/2010 |
| CN | 101827931 | A | 9/2010 |
| CN | 104245917 | A | 12/2014 |
| CN | 105682802 | A | 6/2016 |
| CN | 106085846 | A | 11/2016 |
| EP | 2935559 | B1 | 9/2020 |
| WO | 0101025 | A2 | 1/2001 |
| WO | 0101025 | A3 | 7/2001 |
| WO | 03027223 | A2 | 4/2003 |
| WO | 2008008149 | A2 | 1/2008 |
| WO | 2008008149 | A3 | 7/2008 |
| WO | 2008115626 | A2 | 9/2008 |
| WO | 2008115626 | A3 | 11/2008 |
| WO | 2010023497 | A1 | 3/2010 |
| WO | 2013082612 | A1 | 6/2013 |
| WO | 2015191916 | A1 | 12/2015 |
| WO | 2017062609 | A1 | 4/2017 |

OTHER PUBLICATIONS

European Examination Report mailed on Jan. 17, 2024, for European Patent Application No. 18731562.7, filed on Nov. 15, 2019, 4 pages.

European Examination Report mailed on Jun. 23, 2023, for European Patent Application No. 18731562.7, filed on Nov. 15, 2019, 7 pages.

Grover, W. H. et al. (2006, e-pub. Apr. 6, 2006). "Development and Multiplexed Control of Latching Pneumatic Valves Using Microfluidic Logical Structures," Lab Chip 6:623-631.

Gómez-Sjöberg, R. et al. (Nov. 15, 2007, e-pub. Oct. 23, 2007). "Versatile, Fully Automated, Microfluidic Cell Culture System," Anal. Chem. 79:8557-8563.

International Preliminary Report on Patentability, mailed on Nov. 28, 2019, for PCT Application No. PCT/US2018/032838, filed on May 15, 2018, 7 pages.

International Search Report and Written Opinion mailed on Sep. 6, 2018, for PCT Application No. PCT/US2018/032838, filed on May 15, 2018, 15 pages.

Liding, W. et al. (2012). Polymer Micro-Nanofabrication Technology, National Defense Industry Press, p. 94, 5 pages. (English Translation).

Machinery Industry Press. (Oct. 31, 1997). "Machine Tool Design Manual," vol. 4, Design of Hydraulic Pneumatic System and Modern Design Method of Machine Tool, Hydraulic and Pneumatic System Design and Unit Modern Bed Design, Machinery Industry Press, p. 492, 5 pages. (English Translation).

Nunes, P.S. et al. (Mar. 22, 2010). "Refractive Index Sensor Based on a 1D Photonic Crystal in a Microfluidic Channel," Sensors 10:2348-2358.

Peng, C-C. et al. (2013). "A Microfluidic Cell Culture Array With Various Oxygen Tensions," Lab Chip p. 1-11.

Reichen, M. et al. (2013). "Development of a Multiplexed Microfluidic Platform for the Automated Cultivation of Embryonic Stem Cells," Journal of Laboratory Automation 18(6):519-529.

Wang, H-Y. (Oct. 31, 2008, e-pub. Jun. 12, 2008). "A Microfluidic Cell Array With Individually Addressable Culture Chambers," Biosensors and Bioelectronics 24(4):613-617.

Weltin, A. et al. (2014). "Cell Culture Monitoring for Drug Screening and Cancer Research: A Transparent, Microfluidic, Multi-Sensor Microsystem," Lab Chip 14:138-146.

Yu, H. et al. (2007, e-pub. Jan. 2, 2007). "A Plate Reader-Compatible Microchannel Array for Cell Biology Assays," Lab Chip 7:388-391.

Zhang, B. et al. (Dec. 2009, e-pub. Jul. 21, 2009). "A Self-Contained Microfluidic Cell Culture System," Biomed. Microdevices 11(6):1233-1237.

* cited by examiner

300

1 2 3 4 5 6 7 8

| NUMBER | AREA (mm^2) | CELL DIAMETER (μm) = | 5 | 10 | 15 | 20 | 25 |
|---|---|---|---|---|---|---|---|
| 1 | 22.79 | | 1.16E+06 | 2.90E+05 | 1.29E+05 | 7.25E+04 | 4.64E+04 |
| 2 | 22.33 | | 1.14E+06 | 2.84E+05 | 1.26E+05 | 7.11E+04 | 4.55E+04 |
| 3 | 15.50 | | 7.89E+05 | 1.97E+05 | 8.77E+04 | 4.93E+04 | 3.16E+04 |
| 4 | 17.02 | | 8.67E+05 | 2.17E+05 | 9.63E+04 | 5.42E+04 | 3.47E+04 |
| 5 | 28.84 | | 1.47E+06 | 3.67E+05 | 1.63E+05 | 9.18E+04 | 5.88E+04 |
| 6 | 24.38 | | 1.24E+06 | 3.10E+05 | 1.38E+05 | 7.76E+04 | 4.97E+04 |
| 7 | 19.55 | | 9.96E+05 | 2.49E+05 | 1.11E+05 | 6.22E+04 | 3.98E+04 |
| 8 | 23.71 | | 1.21E+06 | 3.02E+05 | 1.34E+05 | 7.55E+04 | 4.83E+04 |

9 10 11 12 13 14 15 16

| NUMBER | AREA (mm^2) | CELL DIAMETER (μm) = | 5 | 10 | 15 | 20 | 25 |
|---|---|---|---|---|---|---|---|
| 9 | 17.82 | | 9.08E+05 | 2.27E+05 | 1.01E+05 | 5.67E+04 | 3.63E+04 |
| 10 | 11.92 | | 6.07E+05 | 1.52E+05 | 6.75E+04 | 3.80E+04 | 2.43E+04 |
| 11 | 13.59 | | 6.92E+05 | 1.73E+05 | 7.69E+04 | 4.33E+04 | 2.77E+04 |
| 12 | 15.26 | | 7.77E+05 | 1.94E+05 | 8.64E+04 | 4.86E+04 | 3.11E+04 |
| 13 | 16.93 | | 8.62E+05 | 2.16E+05 | 9.58E+04 | 5.39E+04 | 3.45E+04 |
| 14 | 18.60 | | 9.48E+05 | 2.37E+05 | 1.05E+05 | 5.92E+04 | 3.79E+04 |
| 15 | 23.71 | | 1.21E+06 | 3.02E+05 | 1.34E+05 | 7.55E+04 | 4.83E+04 |
| 16 | 25.04 | | 1.28E+06 | 3.19E+05 | 1.42E+05 | 7.97E+04 | 5.10E+04 |

17 18 19 20 21

| NUMBER | AREA (mm^2) | CELL DIAMETER (µm) = | 5 | 10 | 15 | 20 | 25 |
|---|---|---|---|---|---|---|---|
| 17 | 24.33 | | 1.24E+06 | 3.10E+05 | 1.38E+05 | 7.75E+04 | 4.96E+04 |
| 18 | 13.11 | | 6.68E+05 | 1.67E+05 | 7.42E+04 | 4.17E+04 | 2.67E+04 |
| 19 | 15.63 | | 7.96E+05 | 1.99E+05 | 8.85E+04 | 4.98E+04 | 3.18E+04 |
| 20 | 15.25 | | 7.77E+05 | 1.94E+05 | 8.63E+04 | 4.86E+04 | 3.11E+04 |
| 21 | 14.79 | | 7.53E+05 | 1.88E+05 | 8.37E+04 | 4.71E+04 | 3.01E+04 |

MICROFLUIDIC-ENABLED MULTIWELL CELL CULTURE DEVICES AND SYSTEMS FOR PRECISION CULTURE, CONTROL AND MONITORING OF LIVING CELLS

RELATED APPLICATIONS

This application is a continuation application of U.S. patent application Ser. No. 16/614,290, which adopts the international filing date of May 15, 2018, which is the National Phase application under 35 U.S.C. § 371 of International Application No. PCT/US2018/032838, filed May 15, 2018, which is related to and claims priority to U.S. Provisional Patent Application No. 62/507,139, titled "MICROFLUIDIC-ENABLED MULTI-WELL CELL CULTURE PLATE FOR PRECISION CULTURE, CONTROL AND MONITORING OF LIVING CELLS," filed May 16, 2017, which is hereby incorporated by reference in their entirety.

STATEMENT AS TO FEDERALLY SPONSORED RESEARCH

This invention was made with government support under contract no. HHSN271201600007C awarded by the National Institutes of Health. The government has certain rights in the invention.

FIELD

This relates generally to multiwell devices, and particularly to systems and equipment for mirofluidic-enabled multiwell devices for the culture, manipulation and assaying of living cells.

BACKGROUND

The culture, monitoring, manipulation and assaying of living cells is a cornerstone of modern biomedical research, and a major component of preclinical drug discovery activities. The maintenance and inspection of cells is typically carried out manually, relying on repeated, visual inspections and manual media exchanges. Alternatively, these manipulations may be carried out using automated robotic instrumentation that reduces error and variability while using smaller reagent volumes.

SUMMARY

Known solutions for maintenance, inspection, and other manipulation of cells in modern biomedical research are flawed. Manual techniques for control and inspection of equipment, device, and media and are cumbersome and time consuming, are susceptible to human error, and are poorly standardized; require manual media exchanges that may be poorly standardized, and consume large volumes of reagents and cells. Robotic systems occupy large footprint, are costly to implement, are frequently run as a core facility by specialist staff, and are generally used solely for complex, high-throughput screening applications. New approaches to enable the reliable, efficient monitoring and manipulation of live cells over a period of several weeks in a cost-effective format are therefore needed. Disclosed herein are systems, methods, and techniques that address this need through use of multiwell plate systems (e.g., a "SmartPlate") that enables microfluidic-enabled long-term culture, monitoring, and manipulation of live cells in a miniaturized multiwell format that incorporates microenvironment monitoring and closed loop control capabilities. The footprint and well positioning of such integrated multiwell devices may conform to ANSI/SLAS microplate standards, making them compatible with a wide range of standard laboratory instrumentation. The multiwell plate's tiered design may comprise disposable and/or reusable substrate, a microfluidic module, and/or sensing and control modules. The overall system (e.g., including docking stations, control systems, and the like) may be miniaturized for use in tabletop, laboratory, mobile, portable, clinical, field, and/or point-of care settings.

In some embodiments, the substrate may form the lower layer of the multiwell device and may be configured with materials, geometries, and coatings according to various applications. The microfluidic module may be the central layer of the multiwell device and may enable media exchange and perfusion, addition and washout of test compounds, and sampling of media. The sensing and control unit may be the top layer of the multiwell device and may be configured to accommodate monitoring and control of multiple parameters including temperature, pH, and confluency, according to experimental needs.

The systems disclosed herein may thus enable cost-effective and programmable implementation of long-term cell culture in a miniaturized multiwell format that is accessible to researchers in laboratory and field environments. The systems may be well-suited to a wide range of applications that entail long term cell culture ranging from the culture and assaying of immortalized 2D cell cultures to the complex applications such as the generation, culture, and assaying of 3D cell-based models, co-culture models, or reprogramming and differentiation of induced pluripotent stem (IPS) cells. Furthermore, the systems may be compatible with the culture of clinical samples, enabling, for example, testing of patient samples. The multiwell nature of the systems may enable highly parallelized testing of multiple experimental conditions at a scale that conserves significant volumes of reagents and samples compared with both manual and robotic implementation of comparable protocols.

The systems and techniques disclosed herein, along with the next-generation assays and models that they will enable, may benefit public health by significantly enhancing the throughput and robustness of live cell systems used to evaluate the efficacy of therapeutics, in turn improving the ability to identify beneficial therapies for unmet medical needs.

DETAILED DESCRIPTION

The use of advanced cell-based disease models and long-term live cell assays in drug discovery is increasing rapidly. Maintaining these cellular systems in industry standard multiwell plates typically relies on repeated cumbersome and time-consuming visual inspections and manual media exchanges, as explained above. New approaches to enable the efficient monitoring and manipulation of cell cultures in multiwell plates over a period of several weeks are therefore needed.

Disclosed herein are various systems, devices, and techniques that may address this need by leveraging multiwell systems that enables plate-based sensing of microenvironment parameters and automated microfluidic-enabled media exchange and perfusion capabilities in an integrated device with a footprint and well positioning that conforms to the ANSI/SLAS microplate standards.

Figure 1:
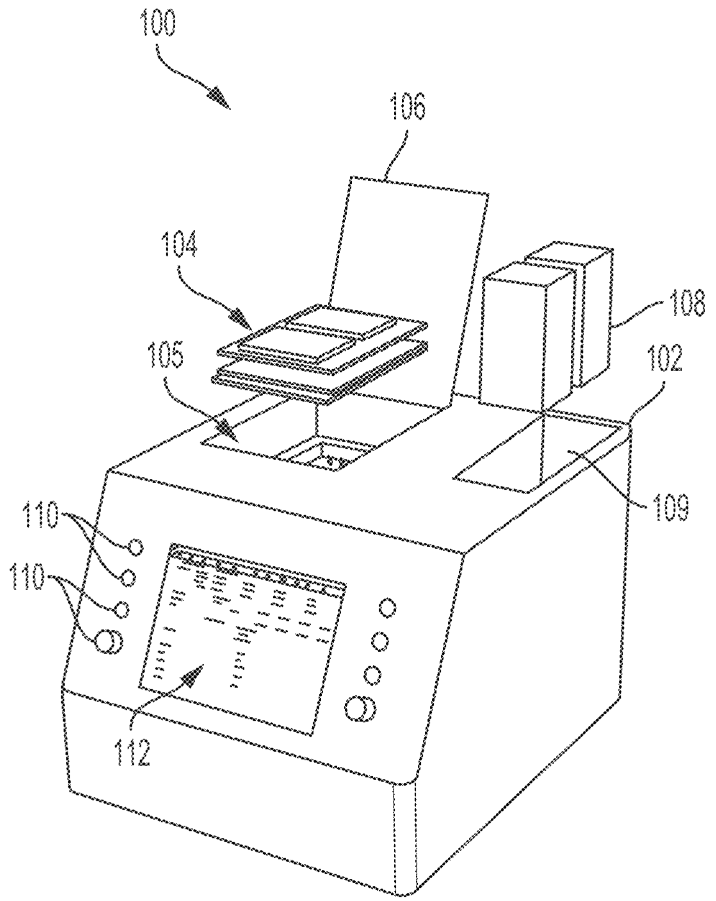
FIG. 1 depicts a cell culture system, in accordance with some embodiments.

FIG. 1 depicts a cell culture system 100, in accordance with some embodiments. As shown in FIG. 1, cell culture system 100 may comprise docking station 102, microfluidic-enabled multiwell plate 104, plate docking portion 105, cover 106, fluid cartridge 108, input devices 110, and display 112. In some embodiments, as described further hereinbelow, system 100 may constitute a tabletop laboratory system configured to manipulate and monitor live cells for various cultures, assays, and/or protocols carried out inside multiwell plate 104. Microfluidic-enabled multiwell plate 104 may comprise a plurality of wells for culture and/or assaying of live cells, one or more sensors for collection of information including data regarding the microenvironment inside plate 104, and one or more valves and/or pumps for automated control of flow of fluid inside plate 104. Components and characteristics of microfluidic-enabled multiwell plates such as multiwell plate 104, in some embodiments, will be discussed below in greater detail.

In some embodiments, docking station 102 may be a tabletop laboratory device having an exterior housing and configured to be placed on a tabletop or bench top and operated by a user. In some embodiments, docking station 102 may be less than or equal to 10 cm, 20 cm, 30 cm, 40 cm, or 50 cm in width. In some embodiments, docking station 102 may be greater than or equal to 10 cm, 20 cm, 30 cm, 40 cm, or 50 cm in width. In some embodiments, docking station 102 may be less than or equal to 10 cm, 20 cm, 30 cm, 40 cm, or 50 cm in height. In some embodiments, docking station 102 may be greater than or equal to 10 cm, 20 cm, 30 cm, 40 cm, or 50 cm in height. In some embodiments, docking station 102 may be less than or equal to 10 cm, 20 cm, 30 cm, 40 cm, or 50 cm in depth. In some embodiments, docking station 102 may be greater than or equal to 10 cm, 20 cm, 30 cm, 40 cm, or 50 cm in depth.

As shown in FIG. 1, docking station 102 may comprise plate docking portion 105 configured to receive multiwell plate device 104. In some embodiments, plate docking portion 105 may be configured to fluidly connect docking station 102 and multiwell plate device 104 such that media and/or cell suspensions may flow between the two.

Furthermore, plate docking portion 105 may be configured to electronically communicatively couple docking station 102 and multiwell plate device 104 such that information may be electronically transmitted between the two. In some embodiments, docking station 102 and multiwell plate device 104 may be configured to communicate with one another via signals sent over one or more physical electronic connections that are connected when multiwell plate 104 is inserted into docking portion 105. In some embodiments, docking station 102 and multiwell plate device 104 may be configured to communicate with one another via signals sent over one or more wireless electronic communications links, which in some embodiments may be activated/deactivated when multiwell plate 104 is inserted into/removed from docking portion 105. In some embodiments, an electrical connection may be formed between docking portion 105 and multiwell plate 104 such that one or more batteries of multiwell plate 104 may be charged by docking station 102 while multiwell plate 104 is inserted into docking portion 105.

As shown in FIG. 1, docking station 102 may comprise cover 106, which may be configured to cover plate device 104 and shield it from external light, air, heat, and/or contaminants while it is connected to docking station 102.

As shown in FIG. 1, docking station 102 may comprise cartridge docking portion 109 configured to receive cartridge 108. In some embodiments, cartridge docking portion 109 may be configured to fluidly connect docking station 102 and cartridge 108 such that media and/or cell suspensions may flow from cartridge 108 to docking station 102 under the force of one or more pumps. In some embodiments, fluid flow may be caused by pneumatic actuation of microvalves, diaphragm valves, and/or electrically driven pumps. In some embodiments, the pumps or vacuums that cause fluid to flow from cartridge 108 to docking station 102 may be located in cartridge 108, in docking station 102, external to docking station 102 (e.g., laboratory vacuum equipment), and/or in a mutliwell device docked with docking station 102. In some embodiments, system 100 may be configured to be able to be used with external and/or internal pneumatic sources, and the pneumatic source used may be chosen by a user depending on available resources (e.g., in a remote field application, internal pneumatic sources may be required to be used).

In some embodiments, cartridge 108 may be configured to house fluid media and/or cell suspensions inside an exterior housing, and may be configured to be able to be physically inserted by a user into docking portion 109, wherein physically inserting cartridge 108 may cause a fluid connection between docking station 102 and cartridge 108 to be connected. In some embodiments, using a cartridge such as cartridge 108 may ensure sterility of cell suspension and other fluids used in system 100 by minimizing the need for users or robots to physically manipulate the fluids in open space.

In some embodiments, in addition to or alternately to a media cartridge docking to cartridge docking portion 109, a media cartridge may be configured to dock directly to a multiwell device. In some embodiments, a media cartridge configured to dock directly to a multiwell device may have a smaller physical form factor than a media cartridge configured to dock to cartridge docking portion 109. In some embodiments, a miniaturized media cartridge configured to dock directly to a multiwell device may allow the multiwell device to be moved to and/or from docking station 102 to other laboratory equipment (e.g., microscopes) or to other locations without interrupting media supply. In some embodiments, system 100 may comprise a first adapter configured to allow a media cartridge configured to dock to cartridge docking portion 109 to alternately dock directly to a multiwell device; in some embodiments, system 100 may comprise a second adapter configured to allow a media cartridge configured to dock directly to a multiwell device to alternately dock to cartridge docking portion 109. In some embodiments, multiwell device 104 may comprise one or more reservoirs configured to be filled with reagent and/or other fluid by docking portion 109 such that multiwell device 104 may be removed from docking station 102 (for example to be transported to another piece of laboratory equipment) without interrupting the continuous availability of media supply.

In some embodiments, in addition to or alternately to a media cartridge docking to cartridge docking portion 109, cell suspension and/or other fluids may be fed into a multiwell device via a one or more pipettes, one or more tubes, one or more syringes, one or more gravitational systems, one or more reservoirs located on the multiwell device, or any other suitable fluid communication mechanism.

In some embodiments, in addition to or alternately to media cartridge 108, system 100 may comprise a separate cell-loading cartridge, vial, or other device configured to dispense cell suspension and optionally be disposed after use. In some embodiments, a small epi-like vial may be loaded into docking station 102 by a user, and the vial or cartridge may maintain the cell suspension in a sterile tissue culture environment.

In some embodiments, docking station 102 may comprise various pneumatic connection ports configured to pneumatically couple docking station 102 to a multiwell device inserted into docking station 102 and/or to pneumatically couple docking station 102 to a source of pressure and/or vacuum. In some embodiments, a pneumatic manifold (discussed in further detail below) may be disposed inside a housing of docking station 102 and may be configured to selectively pneumatically connect a common source of pressure and/or vacuum to one of various pneumatic connections to a multiwell device; by selectively pneumatically connecting one of various pneumatic lines of the multiwell device to the source of pressure and/or vacuum, valves and/or pumps of the multiwell device may be selectively pneumatically actuated in order to control the flow of fluid inside the multiwell device.

In some embodiments, in addition to cartridge 108 and/or one or more other input sources, system 100 may further comprise an output reservoir that may be connected to a multiwell device and/or docking station 102. In some embodiments, an output reservoir may be any well, reservoir, bag, or other fluid container, and may be configured to receive flow of cell suspension and/or other fluid media from other components of system 100 following use of the fluids. In some embodiments, an output reservoir may comprise a plurality of separate compartments or wells for keeping collected fluid separate following collection. In some embodiments, as described below, the ability to individually address flow to and/or from any well of a multiwell device may allow collection of cell suspension from separate wells in a multiwell device (e.g., smart plate device) into separate compartments, wells, or containers of an output reservoir. In some embodiments, an output reservoir may comprise or be associated with one or more sensors configured to detect flow of fluid into and/or inside the output reservoir.

As further shown in FIG. 1, docking station 102 may comprise user input devices 110, which may comprise electronic and/or physical buttons, keys, knobs, switches, levers, joysticks, touch-pads, touch-screens, microphones, cameras, or the like. Input devices 110 may be configured to detect one or more inputs executed by a user, and to accordingly send one or more signals to a processor associated with device 100, wherein the signal sent indicates the detection of the input executed by the user.

As further shown in FIG. 1, docking station 102 may comprise display 112, which may in some embodiments be a touch-screen display that may also serve as an input device. Display 112 may be configured to display information regarding microenvironment data collected from multiwell plate 104, environmental data collected from a physical environment surrounding multiwell plate 104 and/or station 102, instructions for a user, alerts for a user, queries for a user, information regarding a status of system 100, and/or log data stored locally or remotely from system 100.

In some embodiments, system 100, including docking station 102 and multiwell plate 104 (in addition to other multiwell devices described herein) may be configured to enable performing cultures, assays, and other protocols on live cells over extended periods of time, with no human or robotic intervention (or minimized human or robotic intervention), and without the use of an incubator. In some embodiments, system 100 may enable performing cultures, assays, and other protocols over a period of greater than 24 hours, 48 hours, 72 hours, 1 week, or 2 weeks, 1 month, 3 months, or 6 months. In some embodiments, system 100 may enable performing cultures, assays, and other protocols over a period of less than 24 hours, 48 hours, 72 hours, 1 week, or 2 weeks. In some embodiments, minimizing physical intervention by humans or robots may minimize opportunities for a sample to become contaminated or compromised.

In some embodiments, system 100 may comprise one or more computing components such as processors, memory, storage, and communication interfaces for wireless and/or wired communication. In some embodiments, system 100 may be configured to receive stores and/or execute instructions for controlling one or more control, monitoring, input receiving, data outputting, and/or logging functions of system 100 for the execution of cultures, assays, and or other live cell protocols. In some embodiments, system 100 may be configured to be the primary control module for controlling the functioning of a multiwell device inserted in system 100, such as by being inserted in docking station 102. In some embodiments, one or more computing components of system 100 may be located locally to docking station 102 (e.g., they may be comprised in docking station 102), and/or they may be located remotely from docking station 102 (e.g., they may communicate with docking station 102, and/or with other components of system 100) via wired or wireless (e.g., network) electronic communication.

Figure 2A:
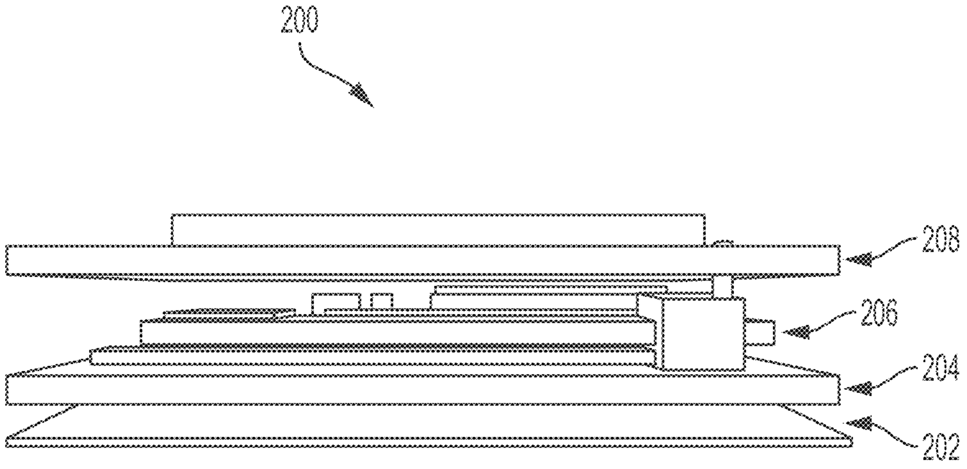
FIGS. 2A-2C depict various views of a multiwell plate device for use in a cell culture system, in accordance with some embodiments.
Figure 2B:
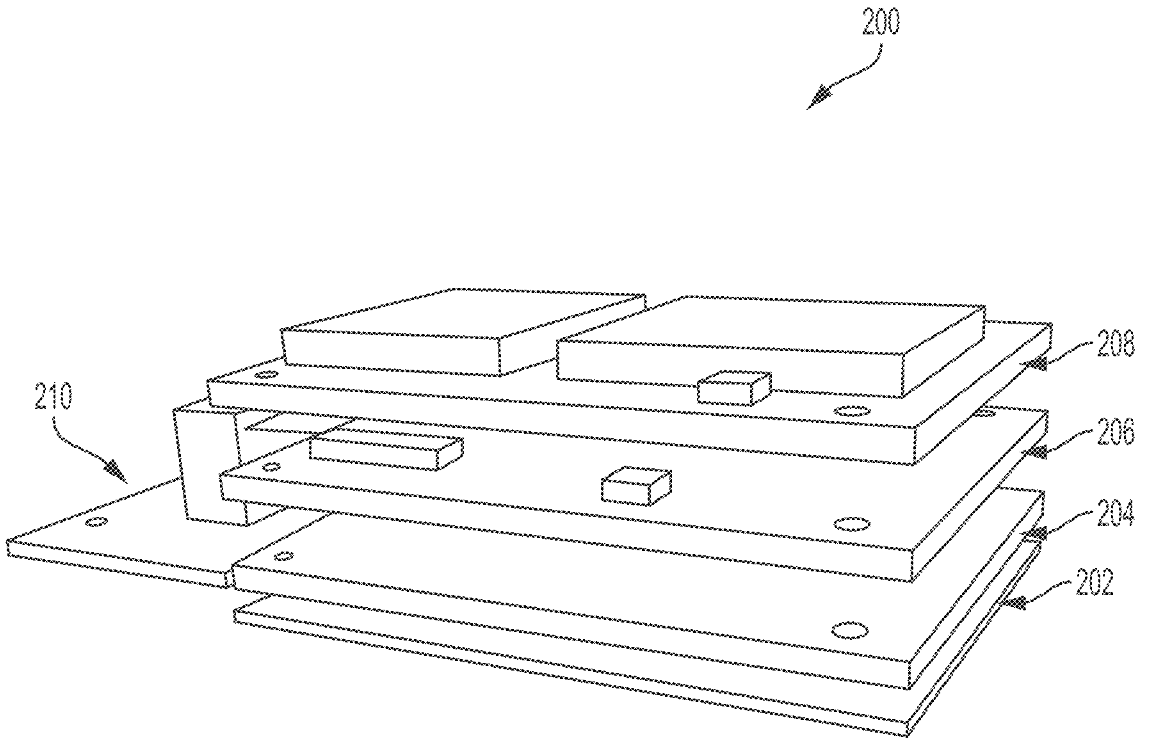
Figure 2C:
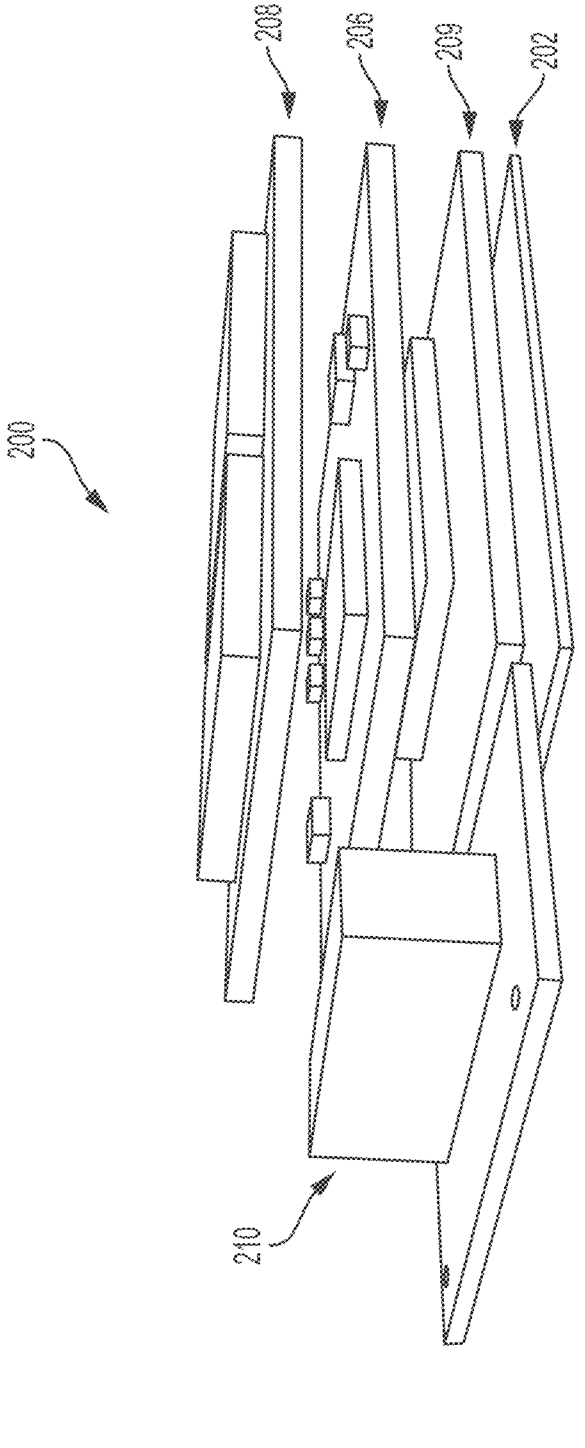

FIGS. 2A-2C depict various views of multiwell plate device 200 for use in a cell culture system such as system 100, in accordance with some embodiments. In some embodiments, multiwell plate device 200 may share some or all characteristics in common with multiwell plate 104 as discussed above with reference to FIG. 1. As shown in FIGS. 2A-2C, multiwell plate device 200 may comprise microfluidics layer 200, sensor layer 204, microcontroller layer 206, and battery layer 208. In some embodiments, any one or more of the four layers 202-208 may be configured to be able to be removed from the other layers and reattached to the other layers. In this way, the layers may act as modules that may be removed, used in one or more downstream analysis procedures or other procedures, disposed of, replaced, and/or recombined by a user. In some embodiments, a user may select a microfluidics layer or a sensor layer having channel arrangements or properties, well arrangements or properties, and/or sensor arrangements or properties suitable for a desired culture, assay, or protocol. In some embodiments, the layers may be attached to one another by a mechanical connection, an adhesive connection, a magnetic connection, and/or by application of external force (e.g., they may be clamped or pressed together). In some embodiments, any one or more of the four layers 202-208 may be referred to as modules.

In some embodiments, multiwell plate device 200 may be configured to enable culture and/or assaying of live cells in a plurality of individually-addressable wells in the microfluidic layer; may be configured to enable automated control and monitoring of microenvironment conditions and external conditions by one or more sensors in device 200; and may be configured to enable automated control of flow of fluid to and from the wells in the microfluidic layer via one or more micro-valves and/or micro-pumps.

In some embodiments, multiwell plate device 200 may have a length and/or width of less than 7 inches, 5 inches, less than 3 inches, less than 2 inches, or less than 1 inch. In some embodiments, multiwell plate device 200 may have a length and/or width of greater than 7 inches, 5 inches, less than 3 inches, less than 2 inches, or less than 1 inch. In some embodiments, multiwell plate device 200 may have a height of less than 5 mm, 10 mm, 25 mm, or 50 mm. In some embodiments, multiwell plate device 200 may have a height of greater than 5 mm, 10 mm, 25 mm, or 50 mm. In some embodiments, multiwell plate device 200 may be configured to have a footprint that enables the device to be inserted into docking station 102 and/or into other laboratory or field equipment such as a microscope.

In some embodiments, microfluidics layer 202 may comprise a plurality of wells configured to house live cells for culture, assaying, and/or other live-cell protocols. Media and or cell suspensions may flow to and/or from one or more of the wells via microfluidic channels in microfluidics layer 202. Flow of fluid in microfluidics layer 202 may be driven by one or more pneumatic micro-pumps and controlled by one or more micro-valves, which may be automatically driven and/or actuated by a local or remote electronic controller.

In some embodiments, a single pump-stroke of a micropump of microfluidics layer 202, may be configured to displace a volume of fluid per cycle (e.g., per pump-stroke) of less than 2000 nL, 1500 nL, 1000 nL, 500 nL, 250 nL, 100 nL, 50 nL, 10 nL, or 5 nL. In some embodiments, a single pump-stroke a micropump of microfluidics layer 202 may be configured to displace a volume of fluid per cycle of greater than 2000 nL, 1500 nL, 1000 nL, 500 nL, 250 nL, 100 nL, 50 nL, 10 nL, or 5 nL. In some embodiments a diaphragm volume of a micropump of microfluidics layer 202 may be less than 2000 nL, 1500 nL, 1000 nL, 500 nL, 250 nL, 100 nL, 50 nL, 10 nL, or 5 nL. In some embodiments a diaphragm volume of a micropump of microfluidics layer 202 may be greater than 2000 nL, 1500 nL, 1000 nL, 500 nL, 250 nL, 100 nL, 50 nL, 10 nL, or 5 nL. In some embodiments, a pump step of a micropump of microfluidics layer 202 may be less than 500 mS, 400 mS, 300 mS, 200 mS, or 100 mS. In some embodiments, a pump step of a micropump of microfluidics layer 202 may be greater than 500 mS, 400 mS, 300 mS, 200 mS, or 100 mS.

In some embodiments, a valve actuation vacuum for a microvalve of microfluidics layer 202 may be −90 kPa±50 kPa, −90 kPa±30 kPa, or −90 kPa±10 kPa. In some embodiments, a valve actuation pressure for a microvalve of microfluidics layer 202 may be +40 kPa±20 kPa, +40 kPa±10 kPa, or +40 kPa±5 kPa.

In some embodiments, sensor layer 204 may be adjacent to microfluidics layer 202. Sensor layer 204 may comprise a printed circuit board and one or more sensors configured to detect one or more characteristics of a microenvironment inside a well and/or channel of microfluidics layer 202. In some embodiments, the detected characteristics of the microenvironment may include one or more of temperature, pressure, pH, humidity, CO2, O2, confluency, fluid flow, input fluid temperature, and/or output fluid temperature. In some embodiments, the sensors used in detecting the characteristics of the microenvironment may be located in sensor layer 204, in microfluidics layer 202, or both.

In some embodiments, a microfluidic multiwell device and/or associated system may be configured to generate a two-dimensional or three-dimensional gradient heat-map of a microfluidic layer such as microfluidic layer 202, in accordance with temperature data received from one or more temperature sensors such as sensors disposed on sensor layer 204.

In some embodiments, confluency monitoring may be achieved electronically through impedance spectroscopy (e.g., the use of interdigitated electrodes that may be controlled and operated by sensor layer 204) or by microscopic imaging and deep learning image analysis software/AI.

In some embodiments, sensor layer 204 may comprise all or part of one or more components such as pneumatic pumps, microvalves, heating elements, and/or other components configured to control or modify one or more detected characteristics of the microenvironment. Thus, multiwell device 200 may detect the characteristics of the microenvironment and may automatically cause them to be controlled to be modified or maintained, such as by adjusting them to a predefined value or range, or by ensuring that they do not deviate from a predefined value or range.

In some embodiments, humidity may be regulated to be maintained at or near 100%, as cells may be harmed by contact with air.

In some embodiments, CO2 levels may be adjusted by the addition of CO2 to a delivered media, such as chemically and/or physically by adding CO2 gas. In some embodiments, CO2 content may determine pH of media. In some embodiments, pH buffer may be added into media to stabilize it, and through continuous exchange of media pH may not change dramatically.

In some embodiments, oxygen regulation (which may be based on measurement of environmental and/or internal oxygen conditions) may include use of one or more degassers to achieve hypoxic conditions.

In some embodiments, pressure may be monitored environmentally for data logging and regulated internally for pneumatic actuation of micropumps, degassers, and/or general fluid actuation.

In some embodiments, temperature may be regulated internally for cell culture conditions using one or more heating or cooling elements based on external and/or internal temperature measurements.

In some embodiments, confluence may be regulated by measuring cell culture conditions and viability of cells, and performing assays and protocols to decrease numbers of cells in a certain area of a well.

In some embodiments, regulation and/or adjustment of any one or more microenvironmental, internal, environmental, and/or external conditions may be performed at least in part on the basis of monitoring of any one or more microenvironmental, internal, environmental, and/or external conditions.

In some embodiments, microcontroller layer 206 may be adjacent to sensor layer 204, such as by being located on the opposite side of sensor layer 204 as microfluidics layer 202. Microcontroller layer 206 may comprise one or more computing components such as processors, memory, storage, and communication interfaces for wireless and/or wired communication. In some embodiments, microcontroller layer 206 may be configured to receive stores and/or execute instructions for controlling one or more control, monitoring, input receiving, data outputting, and/or logging functions of multiwell device 200 for the execution of cultures, assays, and or other live cell protocols. In some embodiments, microcontroller layer 206 may be configured to be the primary control module for controlling the functioning of multiwell device 200.

In some embodiments, microcontroller layer 206 may comprise, or may be communicatively coupled with, one or more sensors configured to sense environmental data regarding an environment surrounding multiwell device 200 (e.g., as distinct from microenvironmental data regarding the microenvironment inside microfluidics layer 202. In some embodiments, the environmental data regarding an environment surrounding multiwell device 200 may comprise one or more of temperature, pressure, humidity, CO2, O2, and/or ambient light characteristics and intensity. In some embodiments, microcontroller layer 206 may be configured to change or maintain one or more characteristics of multiwell device 200 and/or of the contents of microfluidics layer 202 in accordance with the detected surrounding environmental data.

In some embodiments, the ability to control the temperature of the microenvironment, such as via one or more heating elements on-board multiwell device 200 or included in an associated device docking station 102, may enable performing long-term cell cultures and assays without the use of an incubator. That is, by monitoring and controlling the temperature of the system via heating elements of the system, cultures, assays, and other protocols may be performed in a tabletop or benchtop (e.g., room-temperature) environment, or even outdoors.

In some embodiments, battery layer 208 may be adjacent to microcontroller layer 206, such as by being located on the opposite side of microcontroller layer 206 as sensor layer 204. Battery layer may in some embodiments comprise one or more batteries or other power sources configured to provide electrical power for one or more components of multiwell device 200. In some embodiments, multiwell device may be configured to draw power from one or more other sources or electrical power aside from battery layer 208, such as from batteries located elsewhere inside or outside device 200, or from one or more electrical power connections, such as a connection to a docking station or other laboratory equipment to which device 200 may be connected.

As shown in FIGS. 2B and 2C, multiwell device 200 may in some embodiments comprise $CO_2$ sensor 210, which may be configured to detect $CO_2$ levels of a microenvironment of device 200 and/or of the environment surrounding device 200, and may be configured to send signals regarding the detected $CO_2$ levels to sensor layer 204 and/or microcontroller layer 206. In some embodiments, $CO_2$ sensor 210 may be included as part of sensor layer 204; in some embodiments, $CO_2$ sensor 210 may have a height that is greater than a height of sensor layer 204, and $CO_2$ sensor 210 may be positioned in device 200 alongside one or more of the layers and may span a height of two or more of the layers of device 200.

In some embodiments, multiwell device 200 may be configured to form a sterile microenvironment that may not be contaminated by physical handling of the outside of multiwell device 200. In this way, multiwell device 200 may be used in a non-sterile environment to perform sterile cultures, assays, and protocols.

In some embodiments, in addition to the layers discussed above, multiwell device 200 may comprise a substrate layer, which may be a bottommost layer of a multiwell device and may be a glass or plastic (e.g., borofloat glass, any suitable polymer, any suitable copolymer, etc.) layer that may be disposed opposite a microfluidics layer from other layers such as a sensor layer or control layer. In some embodiments, a substrate layer may be configured for imaging, such as by being a thin, antireflective layer configured for high-resolution imaging. In some embodiments, the substrate layer may be configured to be strong enough to support the assembly of the microfluidics module and the multiwell device in which it is disposed. In some embodiments, the substrate layer may have a thickness of less than 25 μm, 50

μm, 100 μm, 500 μm, 1 mm, or 1.5 mm, or 2 mm. In some embodiments, the substrate layer may have a thickness of greater than 25 μm, 50 μm, 100 μm, 500 μm, 1 mm, or 1.5 mm, or 2 mm. In some embodiments, the substrate layer (and other layers such as those in the microfluidics layer) may be configured to not be autofluorescent, to be sufficiently transparent, to be sufficiently flat, to be sufficiently thin, and/or to be sufficiently uniform in thickness such that high-resolution microscopic images may be captured through the layer. In some embodiments, a substrate layer may comprise one or more wells, and may thereby serve as a part of the microfluidics layer (e.g., it may replace the well layers discussed below). In some embodiments, a microfluidics layer may be micropatterned or microengraved and may contain one or more structures such as micropillars or nanopillars.

Figure 3A:
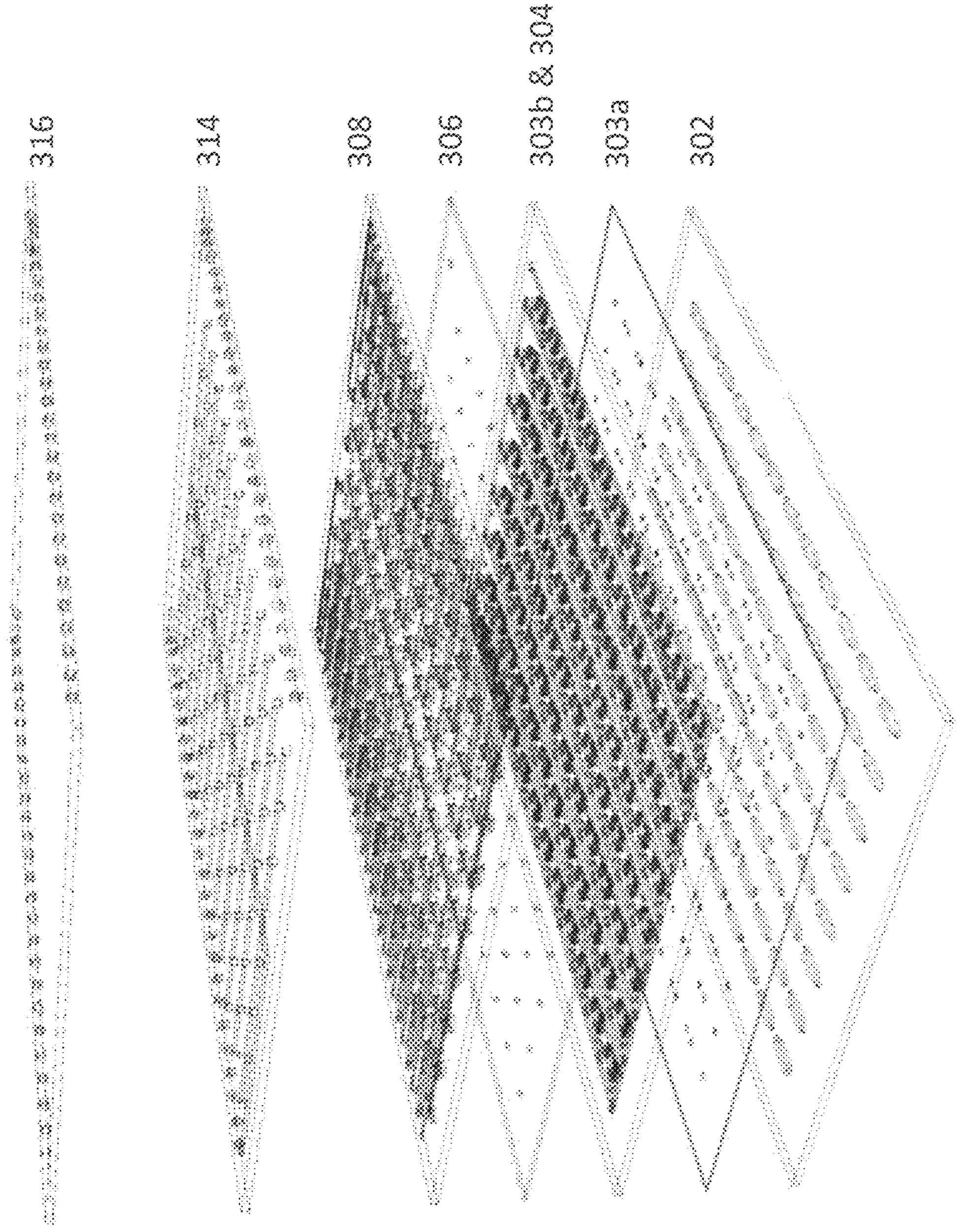
FIG. 3A depicts an exploded view of a microfluidics layer of a multiwell plate device, in accordance with some embodiments.

FIG. 3A depicts an exploded view of a microfluidics layer 300 of a multiwell plate device, in accordance with some embodiments. In some embodiments, microfluidics layer 300 may share any one or more characteristics in common with microfluidics layer 202 as discussed above with reference to FIGS. 2A-2C. In some embodiments, microfluidics layer 300 may be configured to be permanently or impermanent attached to other layers and/or modules (e.g., sensor layers, control layers, and/or battery layers) of a plate device, thereby forming a multiwell plate device configured for performing cultures, assays, and other protocols for live cells. In some embodiments, microfluidics layer 300 may comprise a plurality of wells configured to hold cell suspensions, reagents, and/or other media for use in performing cultures, assays, and other protocols. Microfluidics layer 300 may further comprise microfluidic channels connected to one or more fluid inputs and fluid output, such that the microfluidic channels may be used to deliver fluid to and/or from the microfluidic wells. In some embodiments, one or more of the layers in microfluidics layer 300 may be formed from glass, plastic, Teflon, PDMS, gas-permeable membranes, cyclic olefin copolymer (COC), or other suitable materials. In some embodiments, a substrate layer of microfluidics layer 300 may be made from glass while one or more of the other layers may be made from PDMS or other types of polymers.

As shown in FIG. 3A, microfluidic layer 300 may itself comprise a plurality of sub-layers, including well layer 302, degasser membrane layer 303*a*, degasser layer 303*b*, fluid routing layer 304, pneumatic membrane layer 306, pneumatic layer 308, degasser control layer 314, and sealing layer 316. In some embodiments, microfluidics layer 300 may further comprise one or more additional layers and/or sub-layers not depicted in FIG. 3A.

In some embodiments, well layer 302 may comprise the plurality of wells themselves, while fluid routing layer 304 may comprise microfluidic channels through which fluid may flow to and/or from the channels. In some embodiments, pneumatic membrane layer 306 and pneumatic layer 308 may work together to use pneumatic force to cause the opening and/or closing of microvalves and/or the actuation of micropumps to control the flow of fluid through the microfluidic channels of layer 304 and into and/or out of the wells of layers 302.

In some embodiments, the layers included in microfluidics layer 300 may be stacked with well layer 302 on one side (e.g., the bottom of microfluidics layer 300), followed by fluid routing layer 304, then pneumatic membrane layer 306, then pneumatic layer 308 on the opposite side (e.g., the top of microfluidics layer 300) as well layer 302.

In some embodiments, one or more of layers 304, 306, and 308 may be permanently bonded to one another, such as by being molded, pressed, and/or heated and melted together, and may thereby create a reusable and/or autoclavable control layer. Well layer 302 may then be impermanently connected to the control layer, such as by adhesives, such that well layer 302 may be removed upon experiment completion. In some embodiments, UV ozone treatments may be used to create a strong bond between layers, and that bond may thereafter be released via the use of acids and/or organic solvents. In some embodiments, the layers may be pressed or forced together via external mechanical force without being permanently and/or adhesively bonded to one another. In some embodiments, one or more alignment devices such as guiding pillars, which may be included in a multiwell device itself or may be included in an external device such as docking station 102, may be used in order to align different layers as they are being permanently or impermanently attached to one another.

In some embodiments, one or more of the layers of microfluidics layer 300 may be customized according to experimental needs, for example, to comprise impedance sensors, micro-engraved structures, well geometry for 3D culture, and/or alternative substrate material.

In some embodiments, pneumatic membrane layer 306 may comprise a flexible (e.g., PDMS/teflon) membrane that separates pneumatic layer 308 from fluid routing layer 304, such that pneumatic membrane layer 306 may be caused to deform by pressure exerted on pneumatic membrane layer 306 by pneumatic layer 308. As pneumatic membrane layer 306 deforms, one or more gates or valves may be caused to be actuated such that flow of fluid in fluid routing layer 304 may be controlled by the deformation of pneumatic membrane layer 306. In some embodiments, pneumatic membrane layer 306 may have a thickness of less than 200 μm, 150 μm, 100 μm, or 50 μm. In some embodiments, pneumatic membrane layer 306 may have a thickness of greater than 200 μm, 150 μm, 100 μm, or 50 μm.

In some embodiments, microfluidics layer 300 may have a footprint of 2 inches by 3 inches, or may have a footprint of any other suitable size. In some embodiments, microfluidics layer 300 may have a length and/or width of less than 5 inches, less than 3 inches, less than 2 inches, or less than 1 inch. In some embodiments, microfluidics layer 300 may have a length and/or width of greater than 5 inches, less than 3 inches, less than 2 inches, or less than 1 inch. In some embodiments, microfluidics layer 300 may conform with ANSI/SLAS footprint standards. In some embodiments, microfluidics layer 300 may have a height of less than 1 mm, 2 mm, 3 mm, 4 mm, 5 mm, or 10 mm. In some embodiments, microfluidics layer 300 may have a height of greater than 1 mm, 2 mm, 3 mm, 4 mm, 5 mm, or 10 mm.

In some embodiments, it may be important that one or more components of microfluidics layer 300 remains clean and free from contaminants prior to microfluidic chip fabrication. In some embodiments, one or more cleaning procedures may be performed before and/or during chip fabrication; in some embodiments, cleaning procedures may not be required before and/or during cell loading, cell culture, and/or biological assay procedures. In some embodiments, cleaning of one or more components of microfluidics layer 300 may comprise Piranha cleaning, which may be used to remove organic residues. Two different solutions may be used in Piranha cleaning. In some embodiments, an acid may be used: the acid may comprise a 3:1 mixture of concentrated sulfuric acid (H2SO4) with hydrogen peroxide (H2O2). In some embodiments, a base may be used: the base may comprise a 3:1 mixture of ammonium hydroxide (NH4OH) with hydrogen peroxide (H2O2). Both the acid and the base may be dangerous when hot; in some embodiments, the reaction in the acid is self-starting whereas the base piranha may be required to be heated to 60 degrees Celsius before the reaction initiates. Piranha acids and bases may be prepared in a clean and prepared chemical hood. Once the solution is made, the one or more components of microfluidics layer 300 may be carefully placed inside and be gently agitated for about 10 minutes, then rinsed sufficiently with water and blown dry with an air gun.

In some embodiments, lab cleaning of one or more components of microfluidics layer 300 substrate layer may comprise placing the one or more components in a dish and add a 20 mM Trition-X solution, or other detergent solution; the one or more components may then be placed in ultrasound bath for about five minutes. The one or more components may be rinsed with water and placed in a new dish, where Acetone may be added and the one or more components may be sonicated for about 10 minutes. The one or more components may then be transferred to IPA and sonicated for about 10 minutes. The one or more components may then be removed and blown dry and placed in a dish with a lid. In some embodiments, the one or more cleaned components may be placed on a hot plate at about 150 degrees Celsius for about 30 minutes to remove excess humidity.

In some embodiments, sterilization of one or more components of microfluidics layer 300 may after fabrication and prior to execution of a cell culture, assay, and/or protocol may comprise autoclaving and washing. (In some embodiments, the sterilization may comprise one or more aspects of techniques discussed below in Example 1.) In some embodiments, a rinse using 70% ethanol may be performed for about 15 minutes, a rinse using 1M NaOH may then be performed for about 30 minutes, and a rinse PBS/media may then be performed for about one hour.

In some embodiments, one or more components may be packaged and/or shipped in a sterile (e.g., sealed) condition, such that sterilization before use in a culture, assay, and/or protocol by an end user may not be necessary, and such that the one or more components may be ready for use upon being unsealed. In some embodiments in which one or more components may be removed and replaced from a multiwell device, a new sterile component may be used rather than cleaning a previously used component for subsequent use.

Figure 3B:
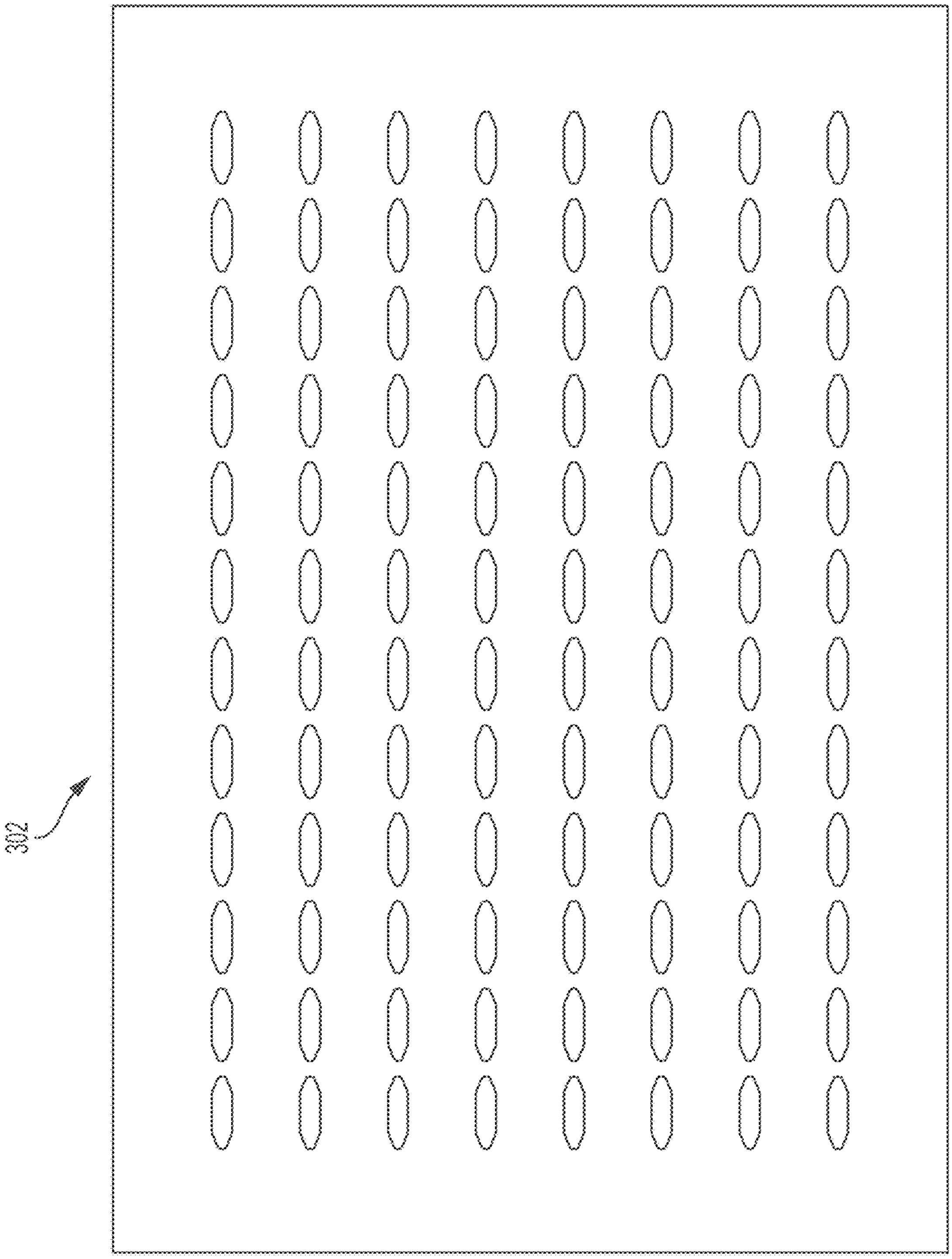
FIG. 3B depicts a well layer of a microfluidics layer of a multiwell plate device, in accordance with some embodiments.

FIG. 3B shows an isolated view of well layer 302, in accordance with some embodiments. As shown, well layer 302 may comprise 96 wells arranged in an 8×12 grid. In some embodiments, well layer 302 may comprise a smaller total number of wells, such as 6, 12, 24, or 48 wells. In some embodiments, well layer 302 may comprise a total number of wells greater than 96. In some embodiments, the effective area of one or more of the wells in well layer 302 may be less than 5 $mm^2$, less than 10 $mm^2$, less than 20 $mm^2$, less than 30 $mm^2$, or less than 50 $mm^2$. In some embodiments, the effective area of one or more of the wells in well layer 302 may be greater than 5 $mm^2$, less than 10 $mm^2$, less than 20 $mm^2$, less than 30 $mm^2$, or less than 50 $mm^2$.

In some embodiments, wells of well layer 302 may each have an input channel (e.g., inlet) and/or an output channel (e.g., outlet), which may open to a layer adjacent to well layer 302. Thus, input channels and/or output channels of well layer 302 may be in fluid communication with microfluidic channels of fluid routing layer 304, such that fluid may be delivered into the inputs from fluid routing layer 304 and out of the outputs to fluid routing layer 304. In some embodiments, the inlets and/or outlets of well layer 302 may have a width of less than 2 mm, less than 1 mm, less than 0.75 mm, less than 0.5 mm, or less than 0.25 mm. In some embodiments, the inlets and/or outlets of well layer 302 may have a width of greater than 2 mm, less than 1 mm, less than 0.75 mm, less than 0.5 mm, or less than 0.25 mm.

In some embodiments, well layer 302 may have a height of less than 0.05 mm, 0.1 mm, 0.25 mm, 0.5 mm, 0.75 mm, 1 mm, or 2 mm. In some embodiments, well layer 302 may have a height of greater than 0.05 mm, 0.1 mm, 0.25 mm, 0.5 mm, 0.75 mm, 1 mm, or 2 mm.

In some embodiments, well layer 302 may be provided as a separate (e.g., detachable and replaceable) module from the rest of the layers of microfluidics layer 300, which may provide flexibility to vary its configuration to include, in some embodiments, additional sensors (e.g. impedance sensing electrodes); alternative well geometries (e.g. micropatterning or specialized well shape for 3D cultures); alternative materials (e.g. glass, COC, others); and/or alternative coatings (e.g. firbonectin, polylysine etc.). In some embodiments, multiple different well layers having varying characteristics may nonetheless be configured to attach to the same fluid routing layer of a microfluidic device to be in fluid communication with the device; that is, multiple different well layers may be configured such that, by aligning either or any of the well layers with the same fluid routing layer, either or any of the well layers will be in fluid communication with the well layer and thereby be compatible for use with the same microfluidic device. In some embodiments, one or more well layers may be configured such that one or more wells may be used as a reservoirs, mixing areas, and/or compartment etc. for application-specific operations and/or assays.

In some embodiments, well layer 302 may be a substrate layer of microfluidics layer 300 and/or of a multiwell device.

In some embodiments, well layer 302 may be micropatterned and/or microengraved, and/or may contain micropillars and/or nanopillars. In some embodiments, one or more of a thickness, material, micropatterning, coating, and geometrical configuration of well layer 302 may be configured for microscopic imaging. In some embodiments, one or more of a material, micropatterning, coating, and geometrical configuration of well layer 302 may be configured for 2D culture of adherent cells. In some embodiments, one or more of a material, micropatterning, coating, and geometrical configuration of well layer 302 may be configured for co-culture of more than one type of adherent cell. In some embodiments, a system may be configured to address one cell suspension having a first type of adherent cell to a well, and to then address a second cell suspension having a second type of adherent cell to the same reservoir. In some embodiments, the first and second cell suspensions may be drawn from separate reservoirs or other separate sources. In some embodiments, one or more of a material, micropatterning, coating, and geometrical configuration of well layer 302 may be configured for co-culture of adherent cells with other cell types. In some embodiments, one or more of a material, micropatterning, coating, and geometrical configuration of well layer 302 may be configured for culture of suspension cells. In some embodiments, one or more of a material, micropatterning, coating, and geometrical configuration of well layer 302 may be configured for culture of 3D culture models. In some embodiments, the 3D models comprise one or more of tumor spheroids, organoids, vascular networks, bioprinted 3D tissue models, and iPSC-derived 3D tissue models. In some embodiments, one or more of a material, micropatterning, coating, and geometrical configuration of well layer 302 may be configured for culture of one or more of immortalized cells, iPSC, iPSC-derived, or primary cells. In some embodiments, any one or more of the characteristics of well layer 302 set out in this paragraph, and/or any one or more characteristics of a well layer set out elsewhere in this application, may apply equally to a substrate layer that is separate from a well layer.

In some embodiments, well layer 302 may be provided to a user after cells have been seeded into one or more layers and frozen there, such that the user could then attach the well layer to a system and thaw the cells and start an experiment after the cells have thawed. In some embodiments, this process could reduce user input regarding cells and allow specific cell lines engineered for certain biological application to be provided to users.

Figure 3C:
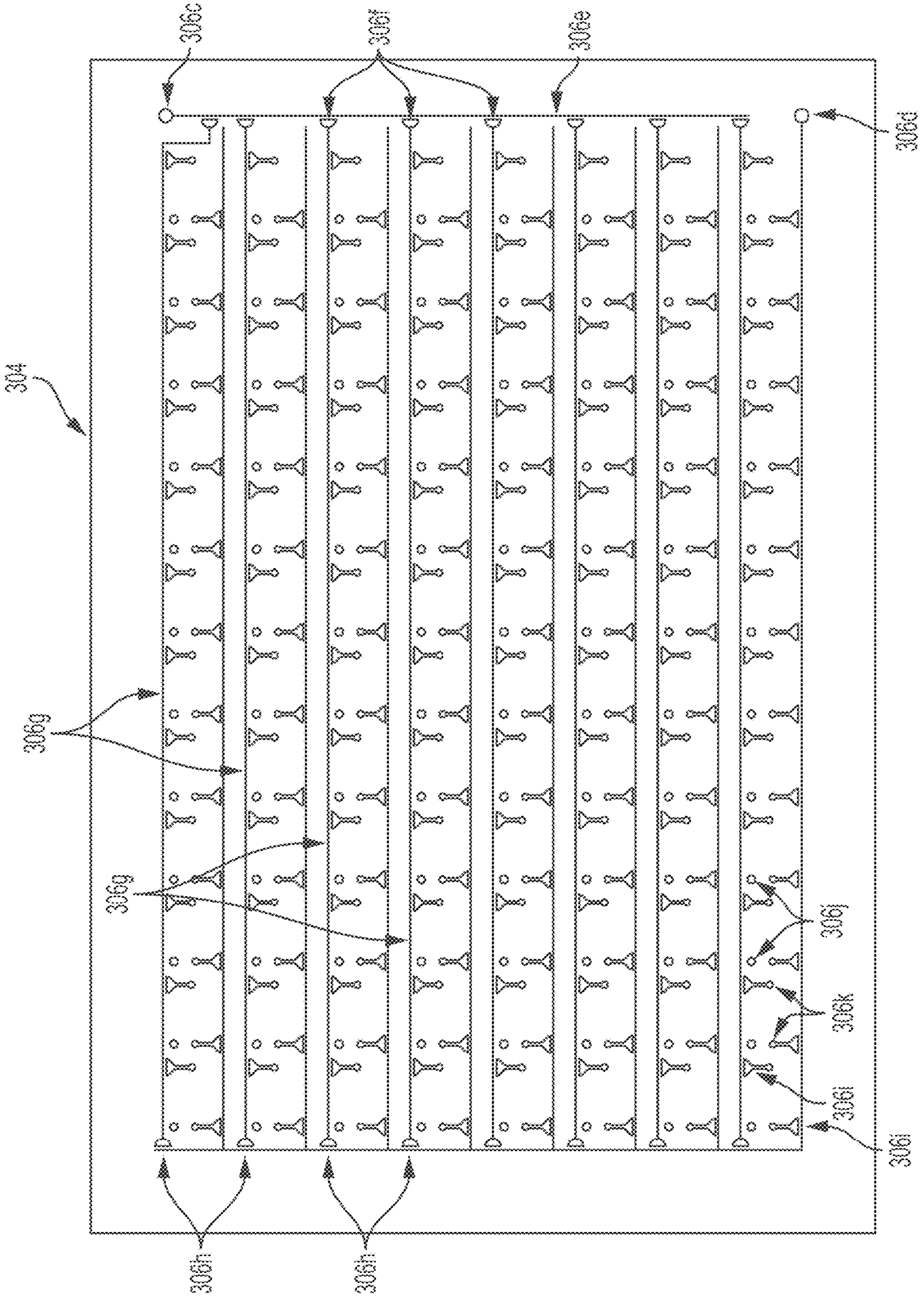
FIG. 3C depicts a fluid routing layer of a microfluidics layer of a multiwell plate device, in accordance with some embodiments.

FIG. 3C shows an isolated view of fluid routing layer 304, in accordance with some embodiments. In some embodiments, fluid routing layer 304 may be formed as a sub-layer of a layer that includes both a fluidic routing sub-layer (and/or a fluid routing side) and a micro-degasser layer (and/or a micro-degasser side). In some embodiments, fluid routing layer 304 may be formed as a sub-layer of a layer that also includes a degasser layer such as degasser layer 303*b*, discussed below with reference to FIG. 3G. In combined configurations, fluid routing features may face toward a pneumatic membrane layer, while degassing features may face in the opposite direction toward a degassing membrane. In some embodiments, fluid routing layer 304 may be fabricated by being milled, injection molded, and/or etched.

In some embodiments, fluid routing layer 304 may comprise a plurality of microfluidic channels configured to permit the flow of cell suspensions, reagents, and/or other fluids to and/or from the wells of well layer 302. In some embodiments, the microfluidic channels of fluid routing layer 304 may be in fluid communication with one or more of the wells of well layer 302, and may be configured to allow the flow of fluid to be individually addressed to any one of the wells in well layer 302 (as will be discussed in further detail below).

Fluid routing layer 304 may comprise fluid inlet 306*c*, which may connect to and receive fluid from a docking station, such as docking station 102, manifold connector 1200, and/or individual fluid connectors such as, but not limited to, pipette tips, tubing, reservoirs, and/or other outside sources of fluid.

Fluid routing layer 304 may comprise fluid outlet 306*d*, which may be fluidly connected to an output reservoir or other downstream fluid destination. In some embodiments, fluid outlet 306*d* may be connected to docking station 102, manifold connector 1200, and/or other fluid connectors.

Fluid routing layer 304 may comprise fluid inlet channel 306*e*, which may fluidly connect inlet 306*c* to a plurality of row channels (e.g., channels 306*g*) to allow flow of fluid (e.g., reagents, cell suspension, drugs) from inlet 306*c* to one or more of the row channels.

Fluid routing layer 304 may comprise row selection valves 306*f*, which may be configured to selectively open and close to allow and disallow flow of fluid from inlet channel 306*e* to a corresponding row channel (e.g., channels 306*g*). In some embodiments, row selection valves 306*f* may be configured as one of two or more bus valves that is configured to be opened and/or closed simultaneously with one or more other bus valves by a single pneumatic control action; for example, row channel inlet bus valves and row channel outlet bus valves may be opened and closed together with one another. In some embodiments, row-selection valves 306*f* may be configured to be pneumatically actuated by a movement of a pneumatic membrane of microfluidics layer 300, as discussed elsewhere herein.

Fluid routing layer 304 may comprise row channels 306*g*, which may be fluid channels corresponding to a respective row of wells and configured to select the first order of specificity towards addressing individual valves. Individual row valves (e.g., row-selection valves 306*f*) may select the row to which and/or from which fluid may be delivered.

Fluid routing layer 304 may comprise flush valves 306*h*, which may be configured to selectively open and close to allow and disallow flow of fluid from a corresponding row channel (e.g., channels 306*g*) into an outlet channel.

Fluid routing layer 304 may comprise well-selection valves 306*i*, which may be configured to selectively open and close to allow and disallow flow of fluid from row channels (e.g., channels 306*g*) into an individual corresponding well and/or to allow flow of fluid out of an individual well into a row outlet channel and toward an outlet (e.g., outlet 306*d*). In some embodiments, well-selection valves 306*i* may be configured as pairs or sets of two or more bus valves that are configured to be opened and/or closed simultaneously by a single pneumatic control action; for example, well inlet bus valves and well outlet bus valves may be opened and closed together with one another. In some embodiments, well-selection valves 306*i* may be configured to be pneumatically actuated by a movement of a pneumatic membrane of microfluidics layer 300, as discussed elsewhere herein.

Fluid routing layer 304 may comprise via-holes 306*j*, which may be configured to pneumatically connect a degasser structure (e.g., in degasser layer 303*b*) on one side of fluid routing layer 304 to a degasser control layer (e.g., layer 314) on an opposite side of fluid routing layer 304.

Fluid routing layer 304 may comprise well inlets/outlets 306*k*, which may comprise via-holes fluidly connecting the channels of fluid routing layer 304 to wells of well layer 302.

In some embodiments, features 306*c-i* may be micro-engraved, injection molded, and/or etched into a surface of fluid routing layer 304, facing pneumatic membrane 306.

In some embodiments, fluid routing layer 304 may have a thickness of less than 1 mm, less than 0.75 mm, less than 0.5 mm, or less than 0.25 mm. In some embodiments, fluid routing layer 304 may have a thickness of greater than 1 mm, greater than 0.75 mm, greater than 0.5 mm, or greater than 0.25 mm. In some embodiments, fluid routing layer 304 may have an etch depth of less than 50 μm, less than 40 μm, or less than 30 μm. In some embodiments, fluid routing layer 304 may have an etch depth of greater than 50 μm, greater than 40 μm, or greater than 30 μm.

In some embodiments, microfluidic channels of fluid routing layer 304 may have a width or diameter of less than 1 mm, less than 0.5 mm, less than 0.4 mm, less than 0.3 mm, less than 0.2 mm, or less than 0.1 mm. In some embodiments, microfluidic channels of fluid routing layer 304 may have a width or diameter of greater than 1 mm, less than 0.5 mm, less than 0.4 mm, less than 0.3 mm, less than 0.2 mm, or less than 0.1 mm.

Figure 3D:
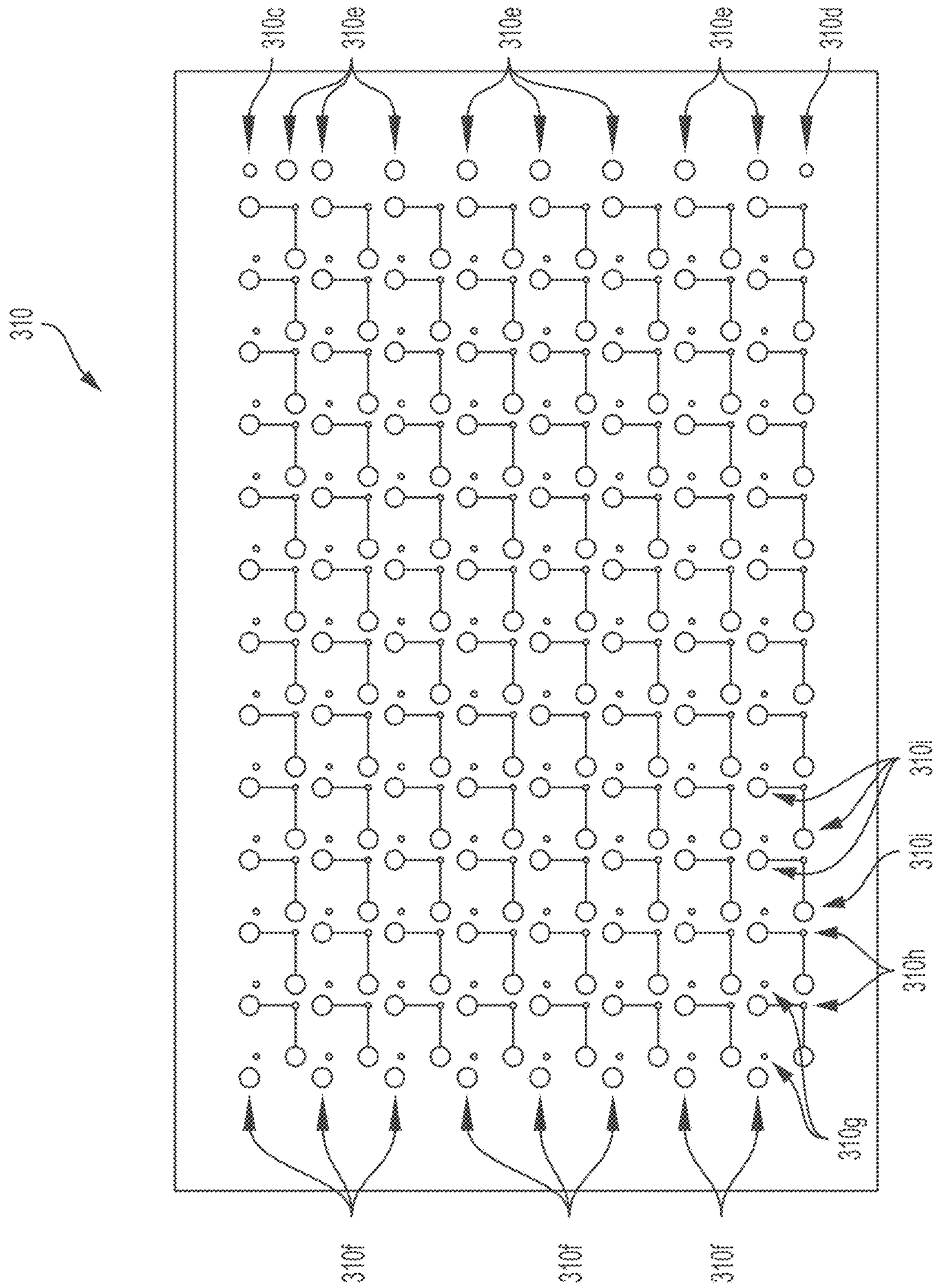
FIG. 3D depicts a pneumatic well-selection layer of a microfluidics layer of a multiwell plate device, in accordance with some embodiments.
Figure 3E:
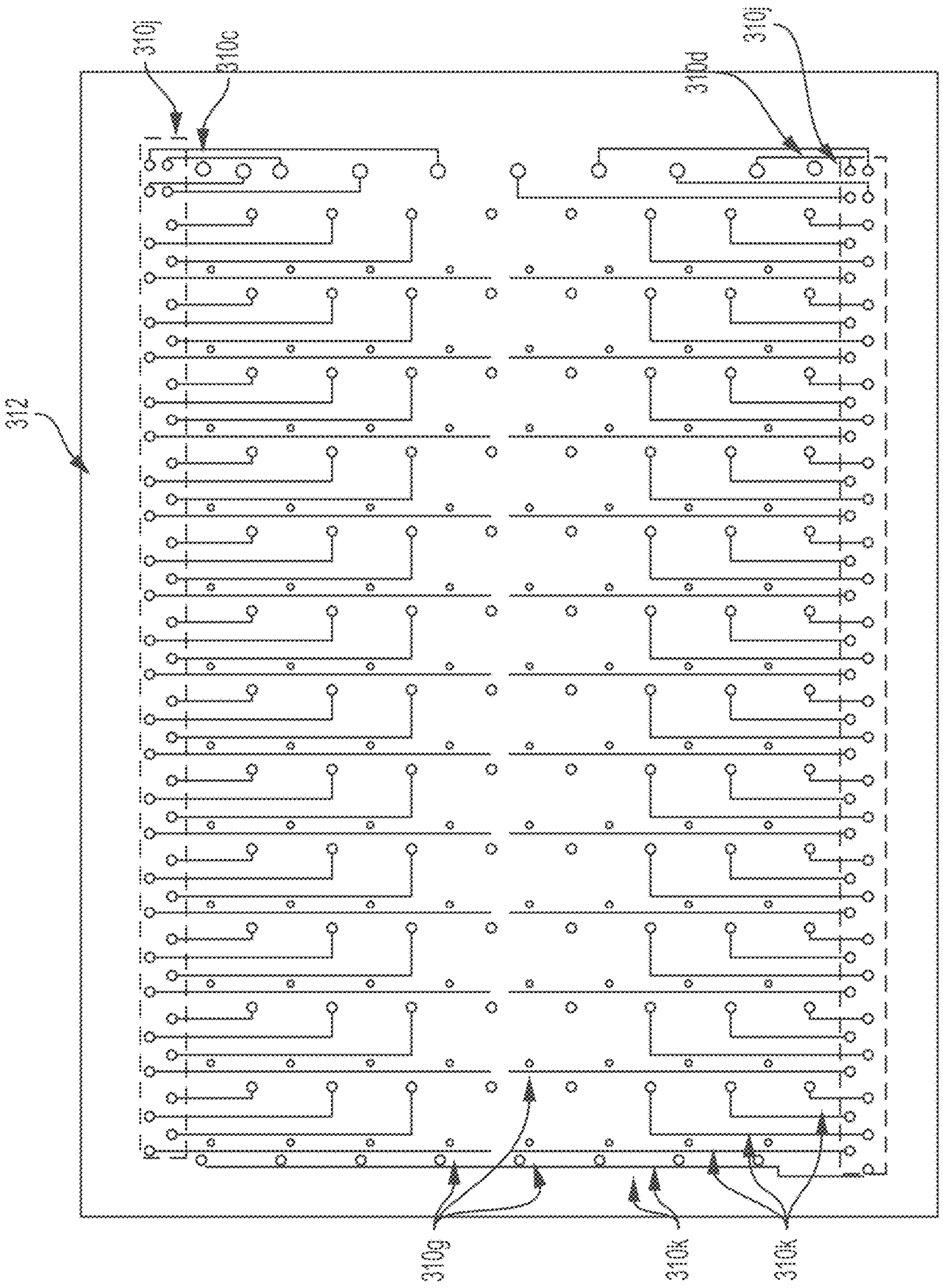
FIG. 3E depicts a pneumatic channel layer of a microfluidics layer of a multiwell plate device, in accordance with some embodiments.

FIGS. 3D and 3E each show a portion of pneumatic layer 308. In some embodiments, pneumatic layer 308 comprises two sublayers: pneumatic well-selection layer 310 and pneumatic control layer 312. In some embodiments, well-selection layer 310 may be referred to as forming one “side” (e.g., a bottom side) of pneumatic layer 308, while pneumatic control layer 312 may be referred to as forming another “side” (e.g., a top side) or pneumatic layer 308. Thus, FIG. 3D shows pneumatic well-selection layer 310, in accordance with some embodiments; and FIG. 3E shows pneumatic control layer 312, in accordance with some embodiments. In some embodiments, pneumatic well-selection layer 310 and pneumatic control layer 312 may be bonded, embosses, milled, and/or injection molded to one another and may be connected via one or more via-holes. In some embodiments, pneumatic well-selection layer 310 may be adjacent to pneumatic membrane layer 306, while pneumatic control layer 312 may be on the other side of pneumatic well-selection layer 310 from pneumatic membrane layer 306.

As shown in FIG. 3D, pneumatic control layer 310 may be used to actuate pneumatic membrane 306; changes of pneumatic pressure may deflect pneumatic membrane 306 within pneumatic bus valve area (deflection chamber) 310*i* for a respective well-specific fluidic valve in fluid routing layer 304, thus allowing fluid to be transported into and/or out of the well in well layer 302.

Pneumatic control layer 310 may comprise inlet 310*c*, which may be a via hole configured to connect to and receive fluid from a docking station, such as docking station 102, manifold connector 1200, and/or individual fluid connectors such as, but not limited to, pipette tips, tubing, reservoirs, and/or other outside sources of fluid.

Pneumatic control layer 310 may comprise fluid outlet 310*d*, which may be fluidly connected to an output reservoir or other downstream fluid destination. In some embodiments, fluid outlet 310*d* may be connected to docking station 102, manifold connector 1200, and/or other fluid connectors.

In some embodiments, one or both of inlet 310*c* and fluid outlet 310*d* may be via holes that connect respectively to corresponding inlets and/or outlets in other layers discussed herein.

Pneumatic control layer 310 may comprise pneumatic deflection chambers 310*e*, which may be chambers configured to apply pressure and/or vacuum to a pneumatic membrane (e.g., pneumatic membrane layer 306) in order to cause the membrane to deflect and to open or close a fluid valve (e.g., lifting gate valve, doormat valve, etc.). Pneumatic deflection chambers 310*e* may correspond to respective row selection valves 306*f* (discussed with respect to fluid routing layer 304) and may be configured to control actuation of those valves 306*f*.

Pneumatic control layer 310 may comprise pneumatic deflection chambers 310*f*, which may be pneumatic deflection chambers corresponding to respective flush valves 306*h* (discussed with respect to fluid routing layer 304) and may be configured to control actuation of those valves 306*h*.

Pneumatic control layer 310 may comprise via-holes 310*g*, which may be configured to pneumatically connect a degasser structure (e.g., in degasser layer 303*b*) on one side of fluid routing layer 304 to a degasser control layer (e.g., layer 314) on an opposite side of fluid routing layer 304. In some embodiments, the pneumatic connections may be formed through respective via-holes 306*j* (discussed with respect to fluid routing layer 304).

Pneumatic control layer 310 may comprise pneumatic via hole connector 310*h*, which may be configured to be pneumatically connected to pneumatic deflection chambers 310*i*, discussed below.

Pneumatic control layer 310 may comprise deflection chambers 310*i*, which may be deflection chambers corresponding to respective well-selection valves 306*i* (discussed with respect to fluid routing layer 304) and may be configured to control actuation of those valves 306*i*.

In some embodiments, pneumatic control layer 310 may be fabricated such features on one or both sides may be milled, injection molded, and/or etched into the layer.

In some embodiments, one or both sub-layers of pneumatic layer 308 maybe formed by a soft photolithography process, injection molding, and/or hard embossing.

In some embodiments, in order to allow for each well to be addressed individually, each well may be gated by two bus valves that may be controlled by a single input line from pneumatic control layer 312.

In some embodiments, pneumatic control layer 312 is connected to pneumatic connection ports/manifold in system 100 through pneumatic port connectors 314*a*. A system unit controller may operate internal solenoid valves and/or a pneumatic manifold unit 1100 in either vacuum or pressure state, thus filling pneumatic lines in pneumatic control layer 312 with either vacuum or pressure. The pressure state may then translate to the membrane on well selection layer 310 through individual pneumatic channels and via holes to the well selection layer 310. Applied vacuum may deflect pneumatic membrane layer 306 and open bus-valves in the fluid routing layer 304. This may allow fluid to be routed into the individual wells connected to those valves and allow fluid to be delivered into through the actuation of a micropump, diaphragm pump, or piezo-electrical pump which may in some embodiments be disposed in microfluidic layer 300 and may in some embodiments be disposed outside microfluidic layer 300.

As shown in FIG. 3E, pneumatic routing layer 312 may comprise inlet 310*c* and outlet 310*d*, as discussed above with respect to pneumatic well-selection layer 310. Pneumatic routing layer 312 may also comprise via-holes 310*g*, as discussed above with respect to pneumatic well-selection layer 310.

Pneumatic routing layer 312 may comprise pneumatic connection ports 310*j*, which may be configured to be respectively pneumatically connected to primary pneumatic connection ports, such as primary pneumatic connection ports 314*a*, discussed below with respect to sealing layer 316. Thus, pneumatic connection ports 310*j* may provide a pneumatic connection from pneumatic routing layer 312 to a source of pressure and/or vacuum outside microfluidic layer 300.

Pneumatic routing layer 312 may comprise pneumatic routing channels 310*k*, which may be individual pneumatic routing channels configured to connect pneumatic connection ports 310*j* to pneumatic deflection chambers 310*e*, 310*f* and/or 310*i*, as shown.

Figure 3F:
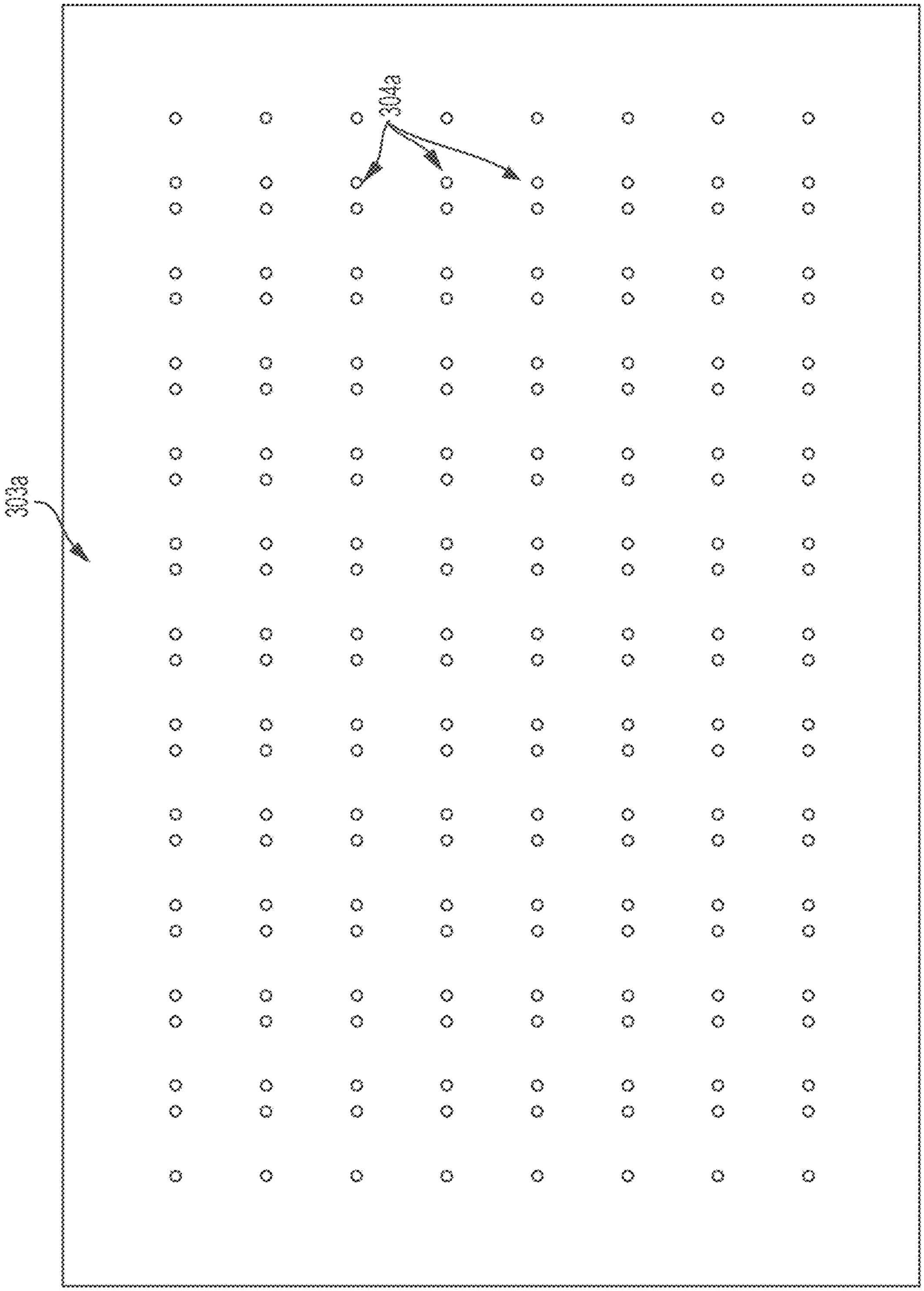
FIG. 3F depicts a degasser membrane layer of a microfluidics layer of a multiwell plate device, in accordance with some embodiments.

FIG. 3F depicts a degasser membrane layer 303*a* of a microfluidics layer of a multiwell plate device, in accordance with some embodiments. In some embodiments, degasser membrane layer 303*a* may be disposed between well-selection layer 302 and degasser layer 303*b* (discussed below). In some embodiments, degasser membrane layer 303*a* may comprise a gas-permeable membrane such as PDMS, and may be configured to allow air bubbles (and/or other gas bubbles) to escape from wells in well layer 302 under vacuum force applied by degasser layer 303*b* on the other side of degasser membrane layer 303*a*.

In some embodiments, degasser membrane layer 303*a* may have a thickness of less than 10 μm, 25 μm, 50 μm, 100 μm, 250 μm, or 500 μm. In some embodiments, degasser membrane layer 303*a* may have a thickness of greater than 10 μm, 25 μm, 50 μm, 100 μm, 250 μm, or 500 μm.

Degasser membrane layer 303*a* may comprise via-holes 304*a*, which may be via-holes configured to fluidly connect channels in fluid routing layer 304 to respective wells in well layer 302.

Figure 3G:
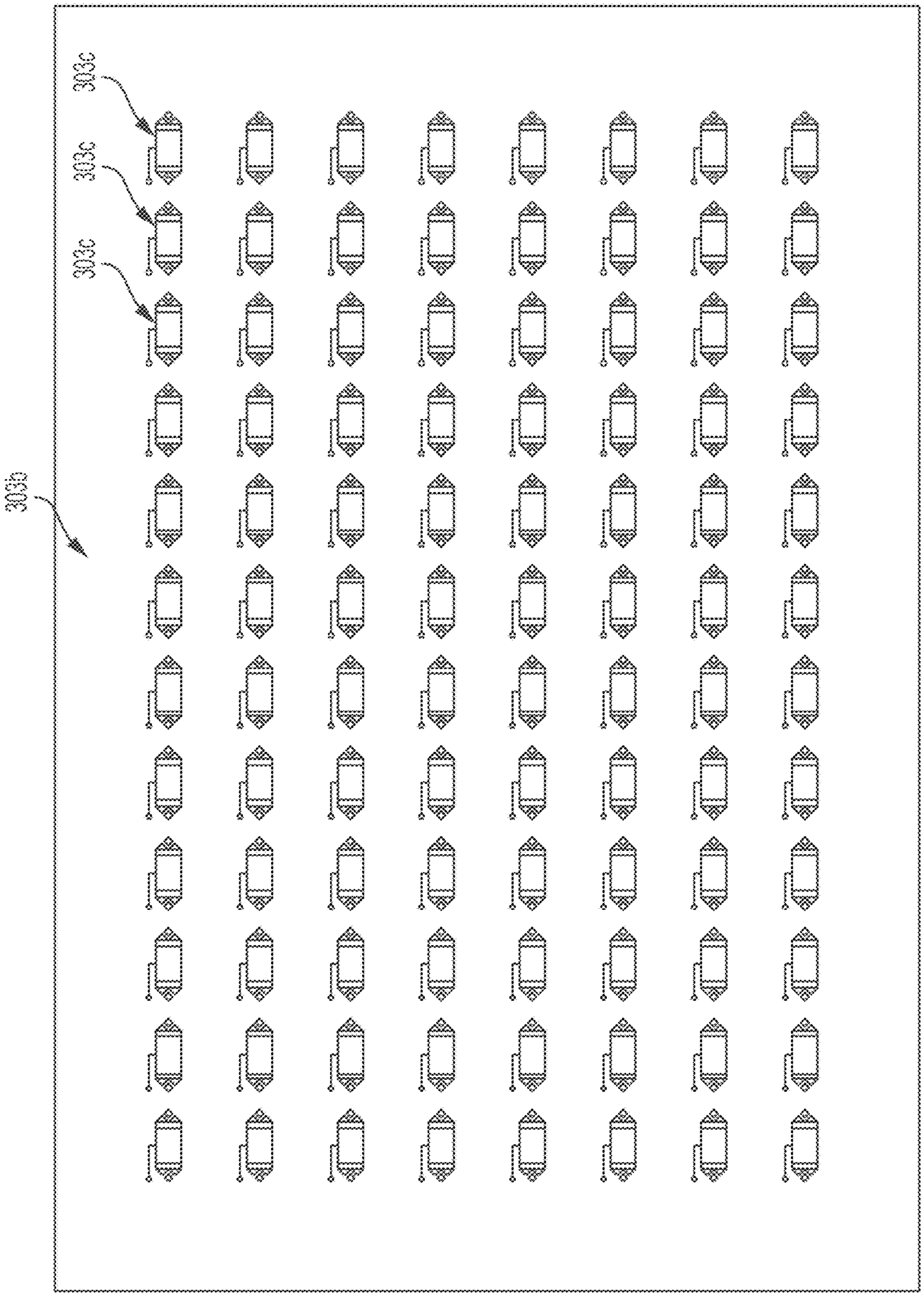
FIG. 3G depicts a degasser layer of a microfluidics layer of a multiwell plate device, in accordance with some embodiments.

FIG. 3G depicts a degasser layer 303*b* of a microfluidics layer of a multiwell plate device, in accordance with some embodiments. In some embodiments, degasser layer 303*b* may be disposed between degasser membrane layer 303*a* and fluid routing layer 304.

In some embodiments, degasser layer 303*b* may be formed as a sub-layer of a layer that includes both a fluidic routing sub-layer (and/or a fluid routing side) and a micro-degasser layer (amd/or a micro-degasser side). In some embodiments, degasser layer 303*b* may be formed as a sub-layer of a layer that also includes a fluid routing layer such as fluid routing layer 304. In combined configurations, fluid routing features may face toward a pneumatic membrane layer, while degassing features may face in the opposite direction toward a degassing membrane. In some embodiments, degasser layer 303*b* may be fabricated by being milled, injection molded, and/or etched.

In some embodiments, degasser layer 303*b* may comprise a plurality of localized degassers 303*c*, which in some embodiments may be secondary degassers provided in addition to a primary, global degasser. While a primary degasser may degas a common input channel, each one of the plurality of localized, secondary degassers 303*c* in degasser layer 303*b* may be located above (and across degasser membrane layer 303*a*) a respective well in well layer 302, and may be configured to degas a specific well.

In some embodiments, each of the secondary degassers 303*c* may comprise one or more via-holes configured to pneumatically connect to a degasser control layer 314, such that vacuum may be applied from degasser control layer 314 to degasser layer 303*b*. The via hole(s) may be connected by one or more channels or other pneumatic routing structures to a series of pillars or other support elements configured to support the vacuum applied to degasser membrane 303*a* such that it does not deflect into the microdegasser.

Degasser layer 303*b* may additionally comprise a plurality of well inlets/outlets, which may take the form of via holes formed in degasser layer 303*b* configured to fluidly connect well inlets/outlets as discussed above with reference to fluid routing layer 304 to well layer 302.

Figure 3H:
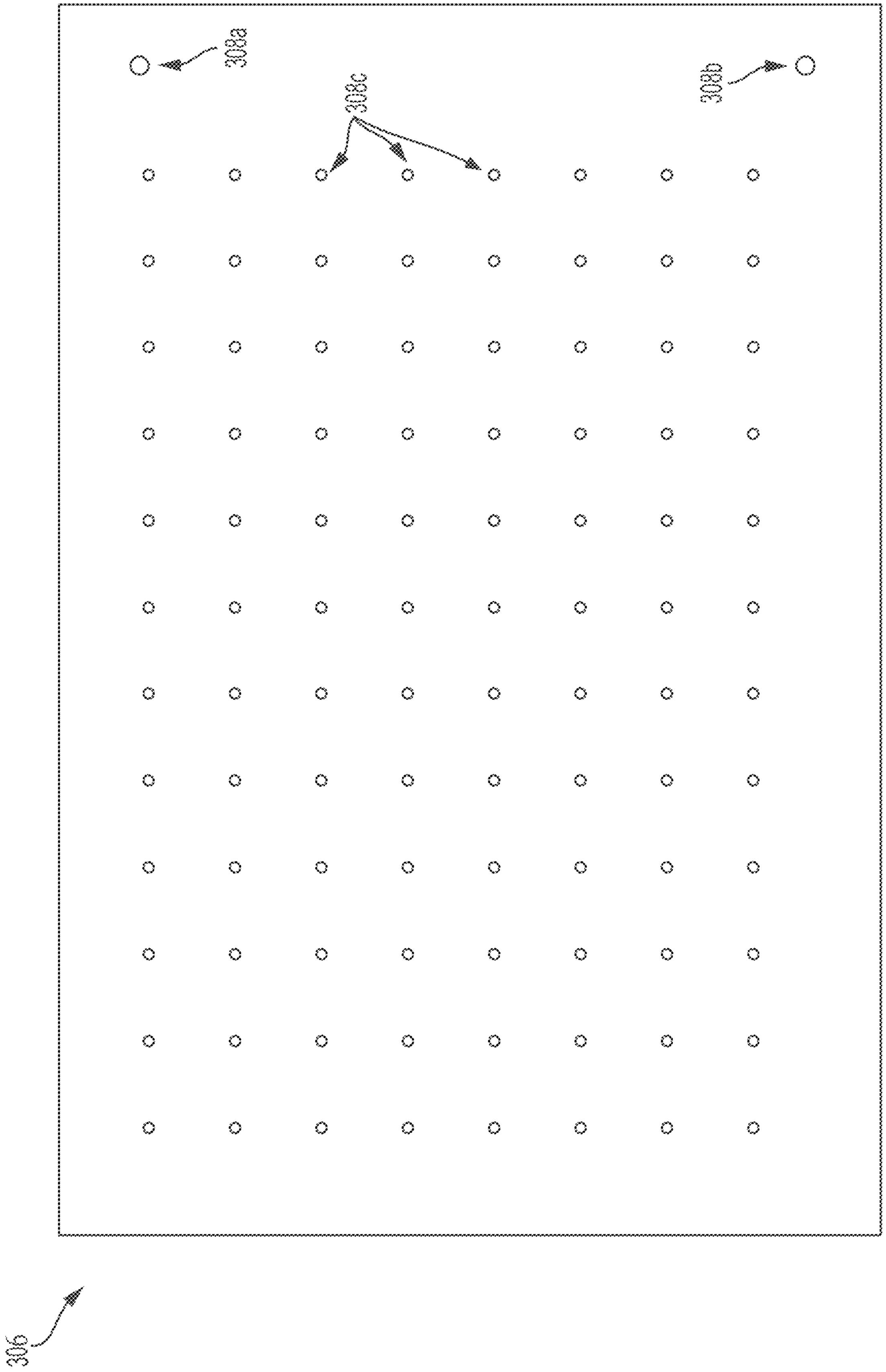
FIG. 3H depicts a pneumatic membrane layer of a microfluidics layer of a multiwell plate device, in accordance with some embodiments.

FIG. 3H depicts pneumatic membrane layer 306 of a microfluidics layer of a multiwell plate device, in accordance with some embodiments.

Pneumatic membrane layer 306 may comprise inlet 308*a*, which may be a via hole configured to connect to and receive fluid from a docking station, such as docking station 102, manifold connector 1200, and/or individual fluid connectors such as, but not limited to, pipette tips, tubing, reservoirs, and/or other outside sources of fluid.

Pneumatic membrane layer 306 may comprise fluid outlet 308*b*, which may be fluidly connected to an output reservoir or other downstream fluid destination. In some embodiments, fluid outlet 308*b* may be connected to docking station 102, manifold connector 1200, and/or other fluid connectors.

In some embodiments, one or both of inlet 308*a* and fluid outlet 308*b* may be via holes that connect respectively to corresponding inlets and/or outlets in other layers discussed herein.

Pneumatic membrane layer 306 may comprise pneumatic via-holes 308*c*, which may be configured to pneumatically connect a degasser structure (e.g., in degasser layer 303*b*) on one side of pneumatic membrane layer 306 to a degasser control layer (e.g., layer 314) on an opposite side of pneumatic membrane layer 306.

Figure 3I:
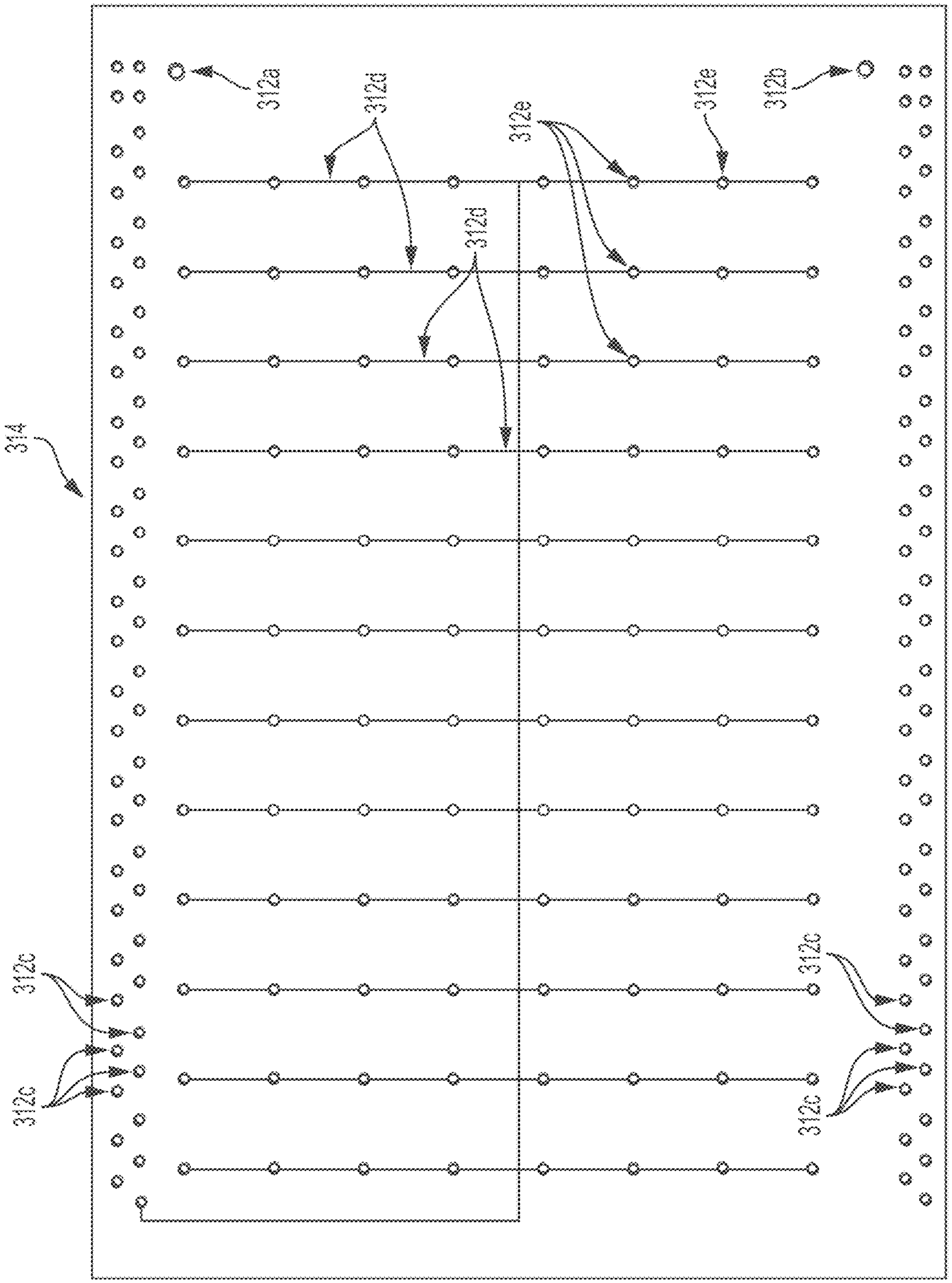
FIG. 3I depicts a degasser control layer of a microfluidics layer of a multiwell plate device, in accordance with some embodiments.

FIG. 3I depicts a degasser control layer 314 of a microfluidics layer of a multiwell plate device, in accordance with some embodiments. In some embodiments, degasser control layer 314 may be disposed between pneumatic control layer 312 and a sealing layer 316 (discussed below in FIG. 3J). In some embodiments, degasser control layer 314 may comprise one or more pneumatic routing channels configured to route vacuum to one or more via-holes to be conveyed to well-specific micro-degassers of a degasser layer such as degasser layer 303*b*. In some embodiments, a single vacuum inlet may be sufficient to apply constant negative vacuum pressure to be conveyed to the micro-degasser structures in degasser layer 303*b*.

In some embodiments, one or more features of degasser control layer 314 may be formed on a side of degasser control layer 314 facing toward a degasser layer such as degasser layer 303*b*.

Degasser control layer 314 may comprise inlet 312*a*, which may be a via hole configured to connect to and receive fluid from a docking station, such as docking station 102, manifold connector 1200, and/or individual fluid connectors such as, but not limited to, pipette tips, tubing, reservoirs, and/or other outside sources of fluid.

Degasser control layer 314 may comprise fluid outlet 312*b*, which may be fluidly connected to an output reservoir or other downstream fluid destination. In some embodiments, fluid outlet 312*b* may be connected to docking station 102, manifold connector 1200, and/or other fluid connectors.

In some embodiments, one or both of inlet 312*a* and fluid outlet 312*b* may be via holes that connect respectively to corresponding inlets and/or outlets in other layers discussed herein.

Degasser control layer 314 may comprise pneumatic via-hole connection ports 312*c*, which may be configured to be respectively pneumatically connected to primary pneumatic connection ports, such as primary pneumatic connection ports 314*a*, discussed below with respect to sealing layer 316. Thus, pneumatic connection ports 312*c* may provide a pneumatic connection from degasser control layer 314 to a source of pressure and/or vacuum outside microfluidic layer 300.

Degasser control layer 314 may comprise pneumatic routing channels 312*d*, which may be configured to pneumatically connect connection ports 312*c* to pneumatic via-holes 312*d*, discussed below.

Degasser control layer 314 may comprise pneumatic via-holes 312*e*, which may be pneumatically connected to connection ports 312*c* via routing channels 312*d* and may be configured to transmit vacuum force to one or more micro-degasser structures of degasser layer 303*b*. In some embodiments, pneumatic via-holes 312*e* may transmit vacuum force to one or more micro-degasser structures of degasser layer 303*b* via one or more of holes 310*g* and 306*j*, as discussed above.

Figure 3J:
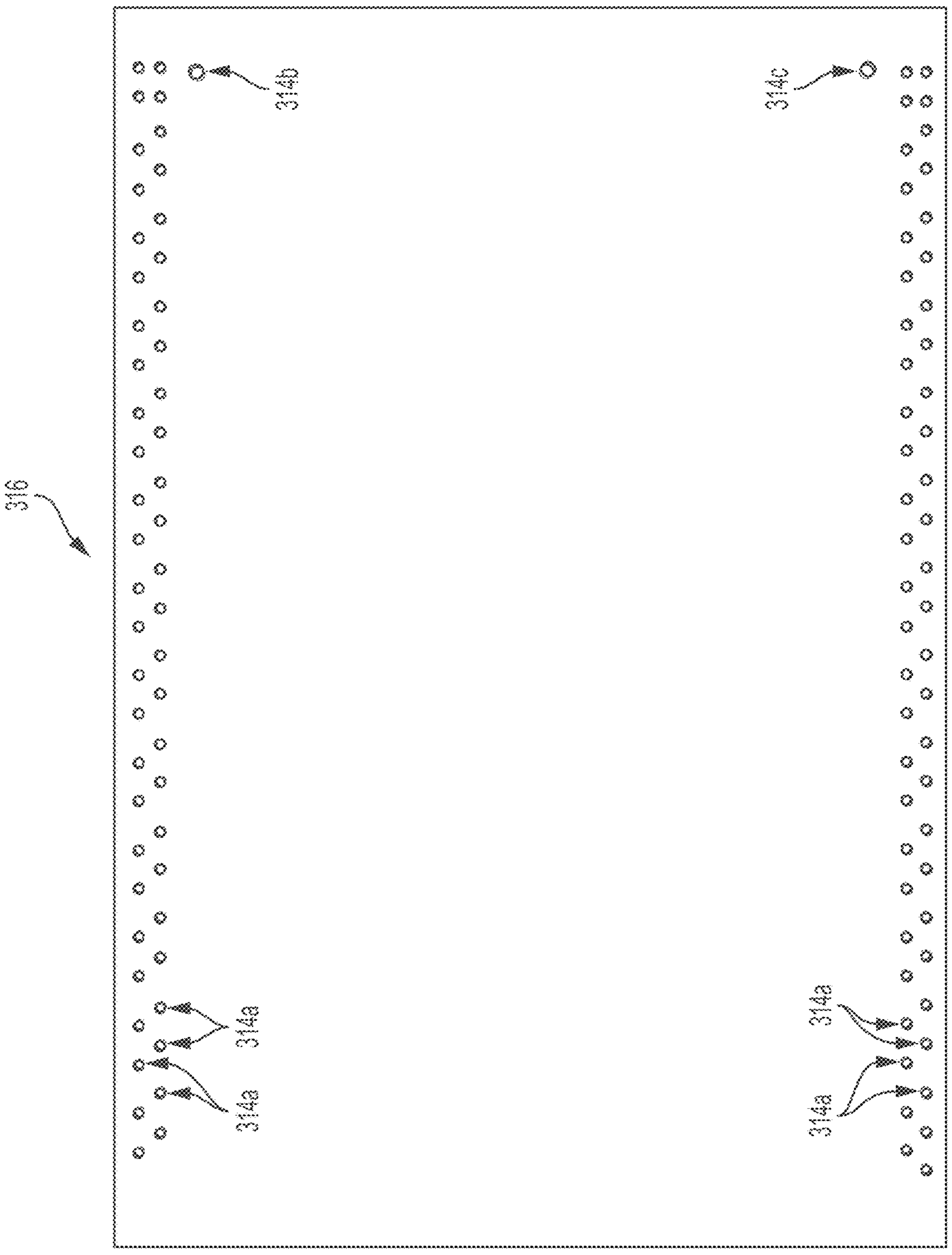
FIG. 3J depicts a sealing layer of a microfluidics layer of a multiwell plate device, in accordance with some embodiments.

FIG. 3J depicts a sealing layer 316 of a microfluidics layer of a multiwell plate device, in accordance with some embodiments. In some embodiments, sealing layer 316 may be disposed on an opposite side of degasser control layer 314 as pneumatic control layer 312. In some embodiments, sealing layer 316 may be referred to as a lid layer. Sealing layer 316 may be configured to seal and close pneumatic features of degasser control layer 314 to ensure proper functioning of microfluidics layer 300.

In some embodiments, sealing layer 316 may comprise primary pneumatic connection ports 314*a*, which may be configured to provide pneumatic connections between external equipment and pneumatic channels and chambers and other structures inside microfluidics layer 300. Connection ports 314*a* may be configured to pneumatically couple to one or more sources of vacuum (and/or positive pressure), such as a manifold connector, one or more tubes, or the like.

In some embodiments, connection ports 314*a* may couple to a portion or component of a docking station such as docking station 102.

Sealing layer 316 may comprise inlet 314*b*, which may be a via hole configured to connect to and receive fluid from a docking station, such as docking station 102, manifold connector 1200, and/or individual fluid connectors such as, but not limited to, pipette tips, tubing, reservoirs, and/or other outside sources of fluid. In some embodiments, inlet 314*b* may connect directly to any one of the sources mentioned above, and may convey the flow of fluid to other corresponding inlet holes in other layers of microfluidics layer 300 discussed above.

Sealing layer 316 may comprise fluid outlet 314*c*, which may be fluidly connected to an output reservoir or other downstream fluid destination. In some embodiments, fluid outlet 314*c* may be connected to docking station 102, manifold connector 1200, and/or other fluid connectors. In some embodiments, fluid outlet 314*b* may connect directly to any one of the downstream fluid destinations mentioned above, and may receive the flow of fluid from other corresponding outlet holes in other layers of microfluidics layer 300 discussed above.

In some embodiments, one or both of inlet 314*b* and fluid outlet 314*c* may be via holes that connect respectively to corresponding inlets and/or outlets in other layers discussed herein.

Figure 4A:
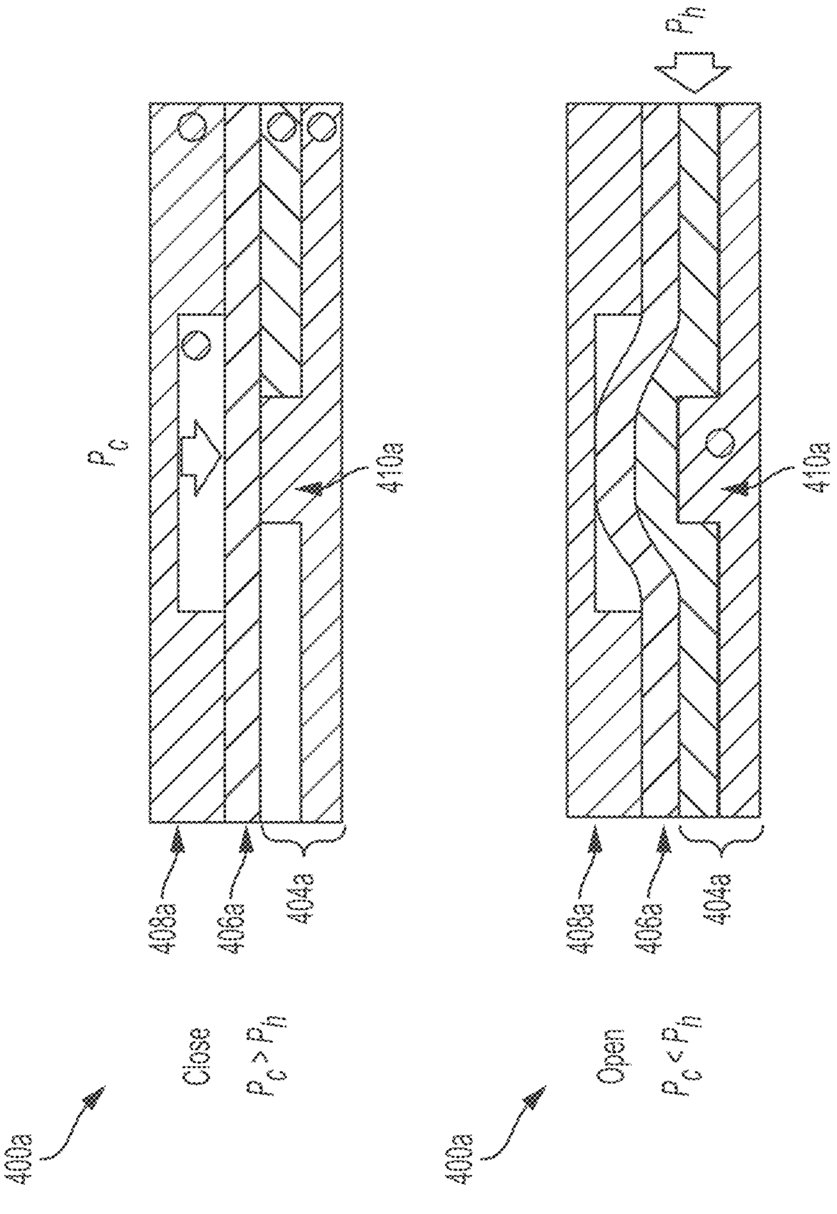
FIGS. 4A & 4B each depict two cross-sectional views of respective microfluidics layers including a pneumatic valve, in accordance with some embodiments.
Figure 4B:
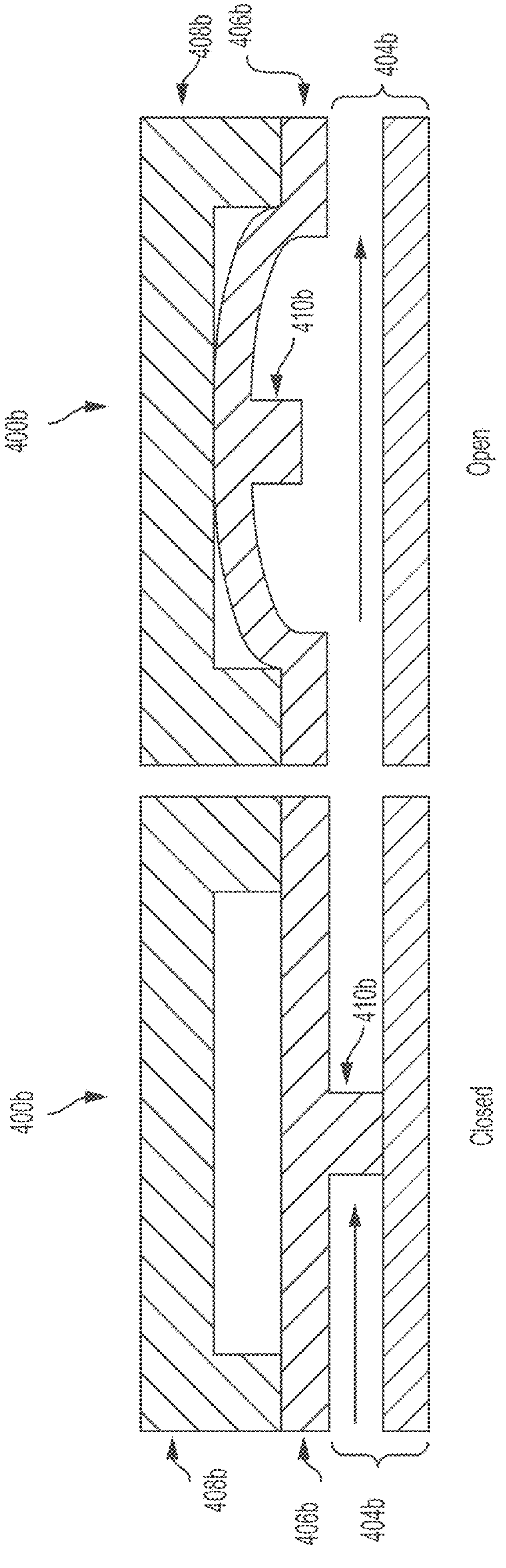
Figure 5:
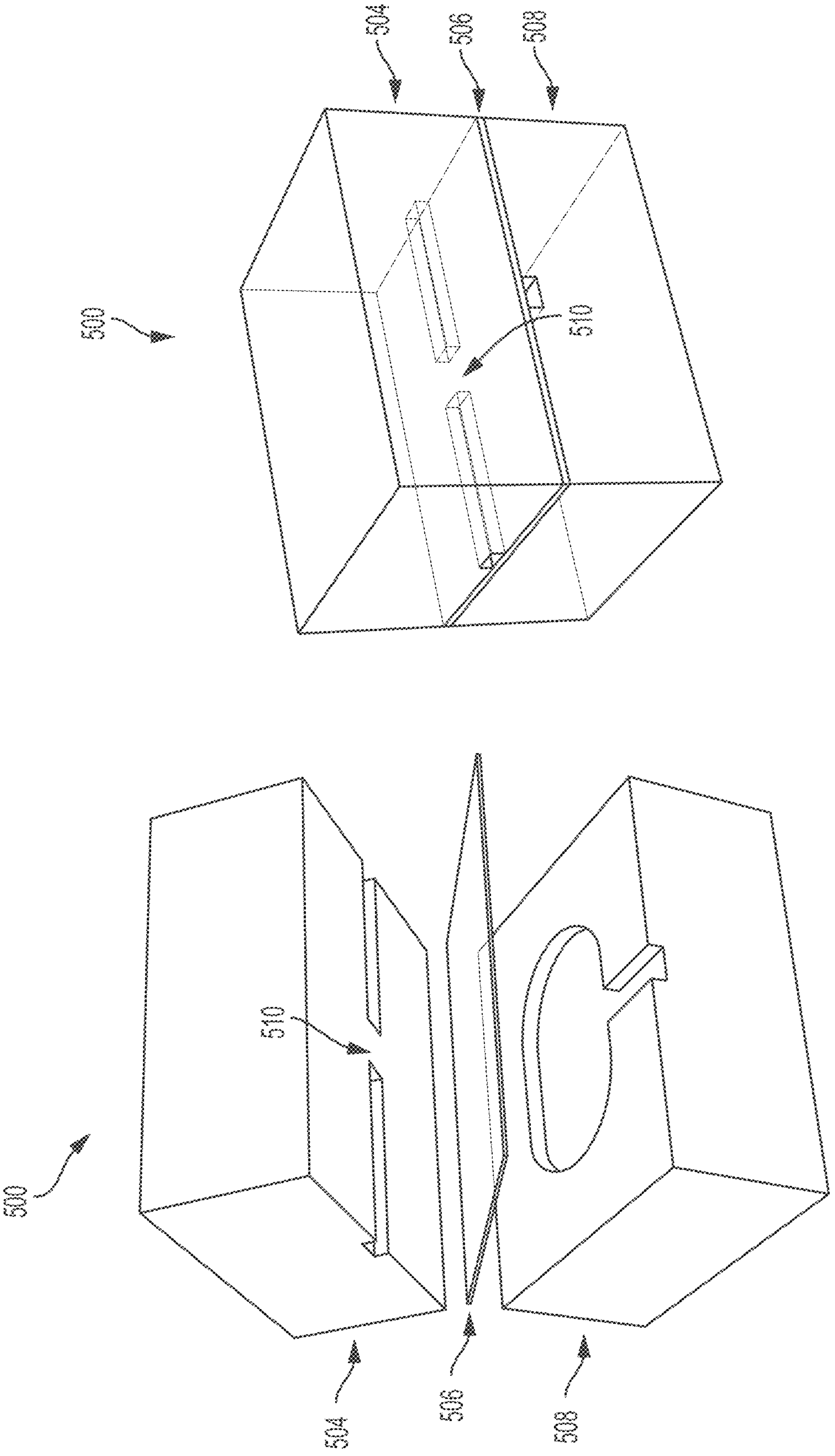
FIG. 5 depicts two cross-sectional views of a respective microfluidics layer including a pneumatic valve, in accordance with some embodiments.

FIGS. 4A, 4B, and 5 each depict two cross-sectional views of respective microfluidics layers including a pneumatic valve, in accordance with some embodiments. FIG. 4A shows two views (top: closed; bottom: open) of an embodiment wherein a pneumatic valve is formed by a gate protruding from a surface of a channel formed in a fluid routing layer. FIG. 4B shows two views (left: closed; right: open) of an embodiment wherein a pneumatic valve is formed by a gate protruding from a surface of a membrane that defines at least one wall of a fluid channel. FIG. 5 shows two views (left: exploded; right: non-exploded) of an embodiment wherein a pneumatic valve is formed by a gate protruding from a surface of a channel formed in a fluid routing layer (similar to the embodiment in FIG. 4A).

As shown in FIG. 4A, microfluidics layer 400*a* may comprise fluid routing layer 404*a*, pneumatic membrane layer 406*a*, pneumatic layer 408*a*, and gate 410*a*. In some embodiments, microfluidics layer 400*a*, fluid routing layer 404*a*, pneumatic membrane layer 406*a*, and pneumatic layer 408*a* may share one or more characteristics in common with the corresponding elements discussed above in with reference to FIG. 3A (e.g., microfluidics layer 300, fluid routing layer 304, pneumatic membrane layer 306, and pneumatic layer 308, respectively).

As shown in FIGS. 4A, fluid routing layer 404*a* may define one or more microfluidic channels through which fluid may flow, and the microfluidic channels may be sealed on one side (e.g., on the top side) by pneumatic membrane layer 406*a*. Pneumatic membrane layer 406*a* may be flexible such that it may be caused to selectively deform into a displacement chamber (e.g., a hollow cavity) formed in pneumatic layer 408*a*, which may be on an opposite side of pneumatic membrane layer 406*a* from fluid routing layer 404*a*.

In the upper diagram of FIG. 4A, the (pneumatic) force exerted on pneumatic membrane layer 406*a* by the pressure (e.g., air pressure) inside the displacement chamber of pneumatic layer 408*a* is greater than the (pneumatic) force exerted on pneumatic membrane layer 406*a* by the pressure (e.g., fluid pressure) from the fluid in the channel of fluid routing layer 404*a*; accordingly, the force exerted on pneumatic membrane layer 406*a* by the pressure (e.g., air pressure) inside the displacement chamber of pneumatic layer 408*a* is sufficient to force pneumatic membrane layer 406*a* toward and against gate 410*a*, thereby closing the valve by creating a seal and preventing flow of fluid (from right to left, in the embodiment shown) through the channel in fluid routing layer 404*a*.

In the lower diagram of FIG. 4A, the force exerted on pneumatic membrane layer 406*a* by the pressure (e.g., air pressure) inside the displacement chamber of pneumatic layer 408*a* is less than the force exerted on pneumatic membrane layer 406*a* by the pressure (e.g., fluid pressure) from the fluid in the channel of fluid routing layer 404*a*; accordingly, the force exerted on pneumatic membrane layer 406*a* by the pressure (e.g., air pressure) inside the displacement chamber of pneumatic layer 408*a* is insufficient to force pneumatic membrane layer 406*a* toward and against gate 410*a*; instead, the force exerted on pneumatic membrane layer 406*a* by the pressure (e.g., fluid pressure) from the fluid in the channel of fluid routing layer 404*a* is sufficient to force pneumatic membrane layer 406*a* away from gate 410*a*, thereby opening the valve by allowing flow of fluid (from right to left, in the embodiment shown) through the channel in fluid routing layer 404*a*.

It should be noted that, in some embodiments, applied vacuum to the displacement chamber lifts and holds pneumatic membrane layer 406*a* away from the gate and thus opens the fluid channel. In some embodiments, through micropump actuation of the fluid, the fluid pressure within the channel may be increased. However, it may not be possible to create a fluid flow without applying a vacuum since otherwise the fluid pressure may be equal to atmospheric pressure and the gate may remain closed. Thus, in some embodiments, applying vacuum may be necessary to allow the gate to be opened.

Thus, by causing the pressure (e.g., air pressure) inside the displacement chamber in pneumatic layer 408*a* to increase or decrease, the valve in FIG. 4A may be selectively opened and closed to selectively allow and disallow flow of fluid through the channel in fluid routing layer 404*a*.

FIG. 4B shows microfluidics layer 400*b*, which may comprise fluid routing layer 404*b*, pneumatic membrane layer 406*b*, pneumatic layer 408*b*, and gate 410*b*. In some embodiments, microfluidics layer 400*b* and its components may share one or more characteristics in common with microfluidics layer 400*a* discussed above with reference to FIG. 4A. In some embodiments, microfluidics layer 400*b* may differ from microfluidics layer 400*a* in that gate 410*b* may be formed as a part of or may be attached to pneumatic membrane layer 406*b*, rather than being formed as a part of or attached to fluid routing layer 404*b*. Thus, pressure changes in the displacement chamber in pneumatic layer 408*b* may pneumatic membrane layer 406*b* to selectively move up and down in order to open the valve by causing gate 410*b* to form a seal by being pressed against a wall of the channel in fluid channel layer 404 (as shown in the diagram at left in FIG. 4B), or alternately to open the valve by causing gate 410*b* to move away from a wall of the channel in fluid channel layer 404 (as shown in the diagram at right in FIG. 4B). This type of valve, which may be called a lifting gate valve, can be used in a configuration/embodiment of fluid routing layer 304 in which the microfluidic wells are incorporated within the same to allow the use of a very thin substrate layer 302 in order to facilitate high resolution imaging capabilities.

Thus, by causing the pressure (e.g., air pressure) inside the displacement chamber in pneumatic layer 408*b* to increase or decrease, the valve in FIG. 4B may be selectively opened and closed to selectively allow and disallow flow of fluid through the channel in fluid routing layer 404*b*.

FIG. 5 depicts two cross-sectional views of a respective microfluidics layer including a pneumatic valve, in accordance with some embodiments. FIG. 5 shows microfluidics layer 500, which may comprise fluid routing layer 504, pneumatic membrane layer 506, pneumatic layer 508, and gate 510. In some embodiments, microfluidics layer 500 and its components may share one or more characteristics in common with microfluidics layer 400*a* discussed above with reference to FIG. 4A. The diagram at left in FIG. 5 shows an exploded view of microfluidics layer 500, while the diagram at right in FIG. 5 shows a non-exploded, partially transparent view of microfluidics layer 500. By causing the pressure (e.g., air pressure) inside the displacement chamber in pneumatic layer 508 to increase or decrease, the valve in FIG. 5 may be selectively opened and closed to selectively allow and disallow flow of fluid through the channel in fluid routing layer 504; this principle may similarly apply to the valves shown in FIGS. 4A and 4B.

In the valves of FIGS. 4A, 4B, and/or 5, if no pressure is applied to a deflection chamber, then the valve may default to a closed position. This may allow for detachment of a device including one of the valves from pneumatic connections (e.g., for transfer to another location or another piece of equipment), without opening valves and allowing fluid to freely flow in the device.

In some embodiments, microfluidics layers, including microfluidics layers 202, 300, 400*a*, 400*b*, and/or 500, of multiwell plate devices may be made in accordance with all or part of one or more known fabrication processes for PDMS chips, including for example known replica molding processes.

Figure 6A:
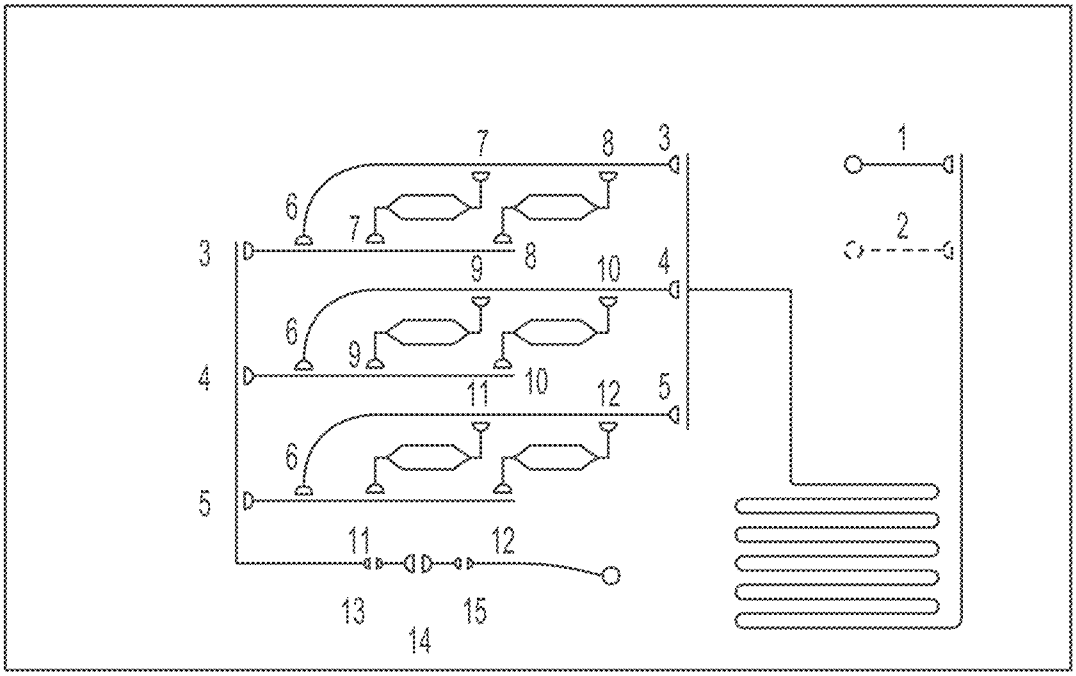
FIGS. 6A-6V depict a schematic view of a fluid flowing through a microfluidics layer of a multiwell plate device having individually-addressable wells, in accordance with some embodiments.
Figure 6B:
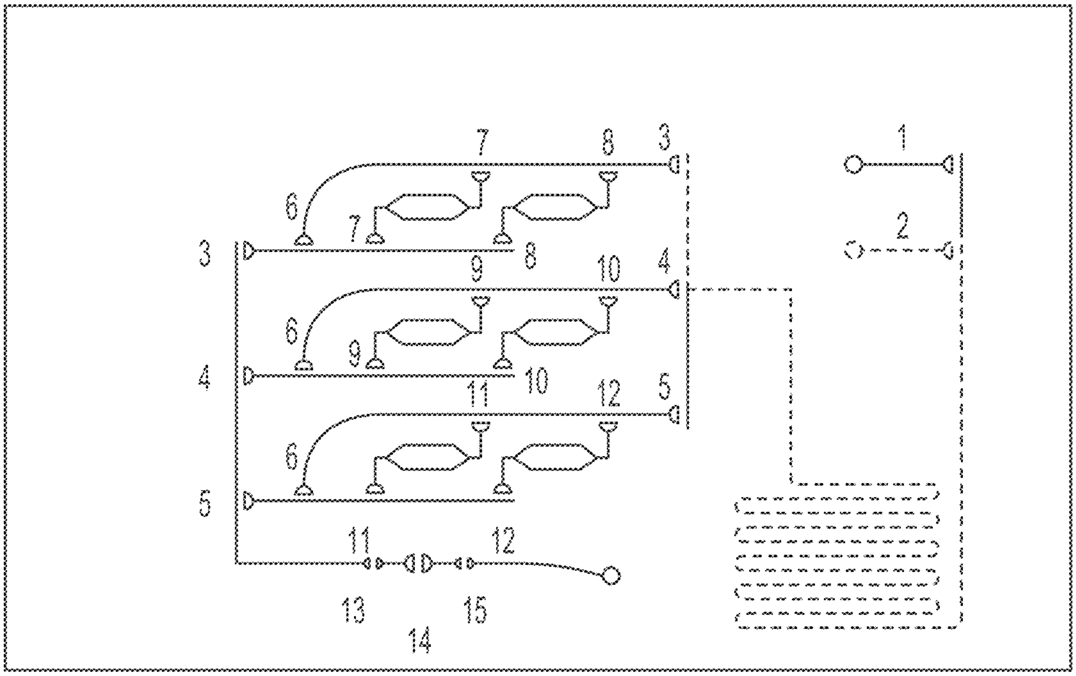
FIG. 6W depicts a graphical representation of the operation of various components or features of a multiwell system over time, in accordance with some embodiments.
Figure 6C:
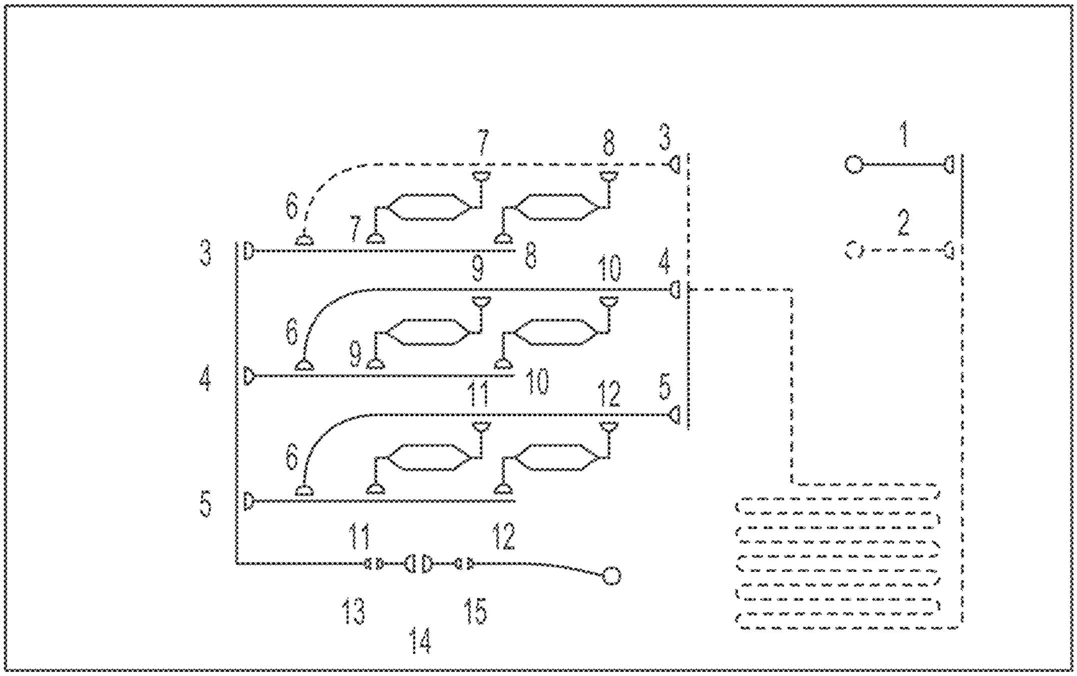
Figure 6D:
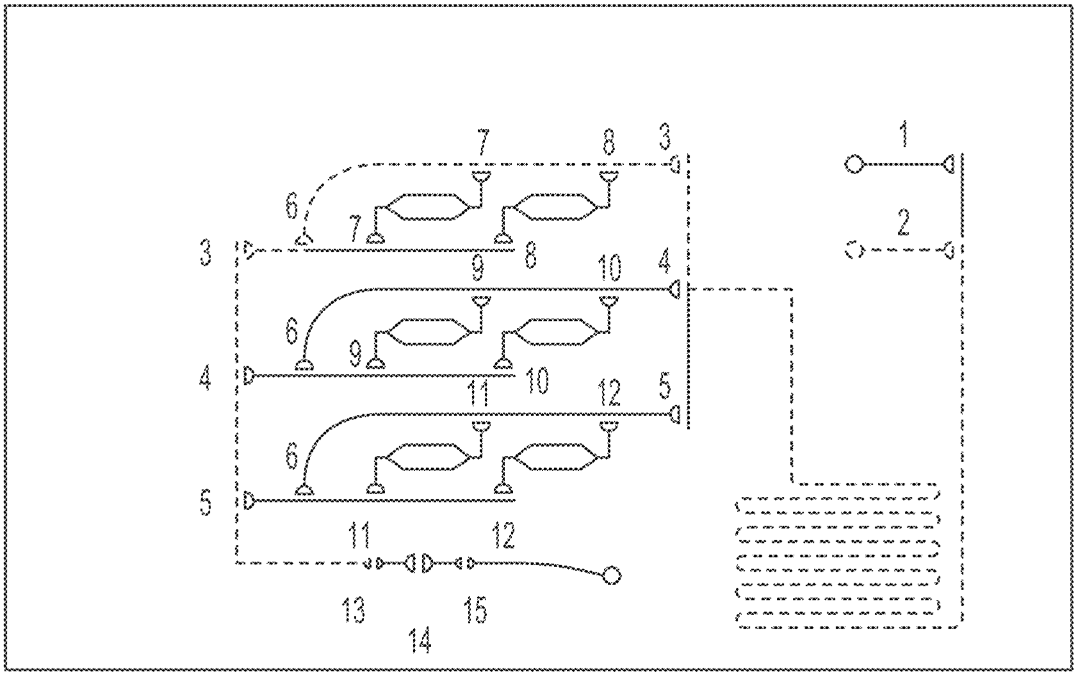
Figure 6E:
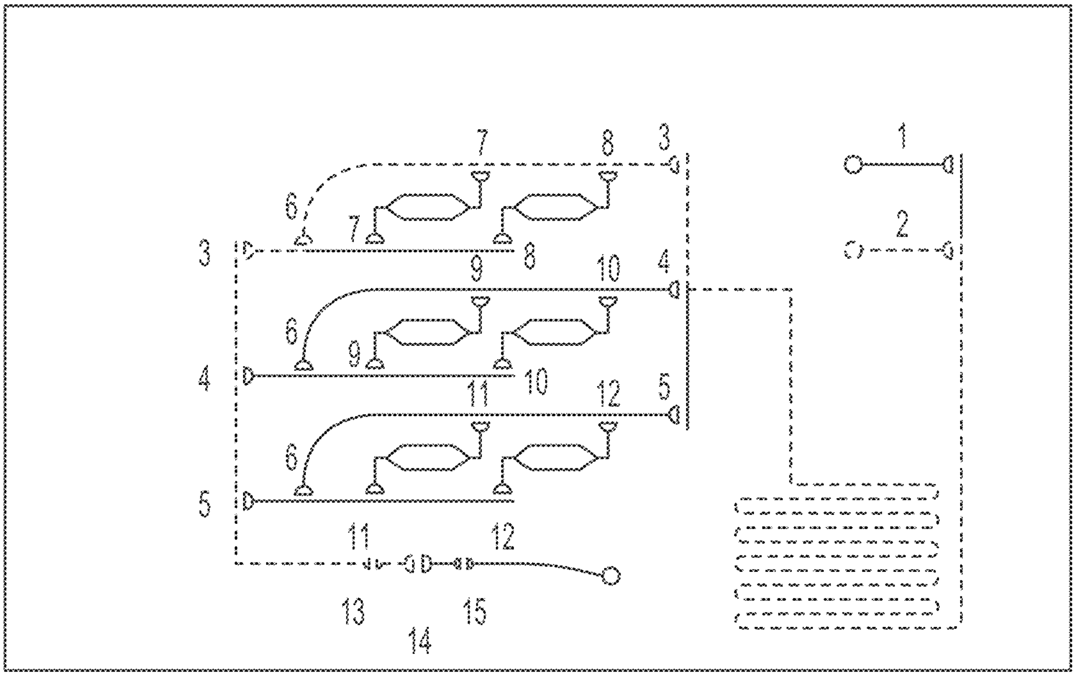
Figure 6F:
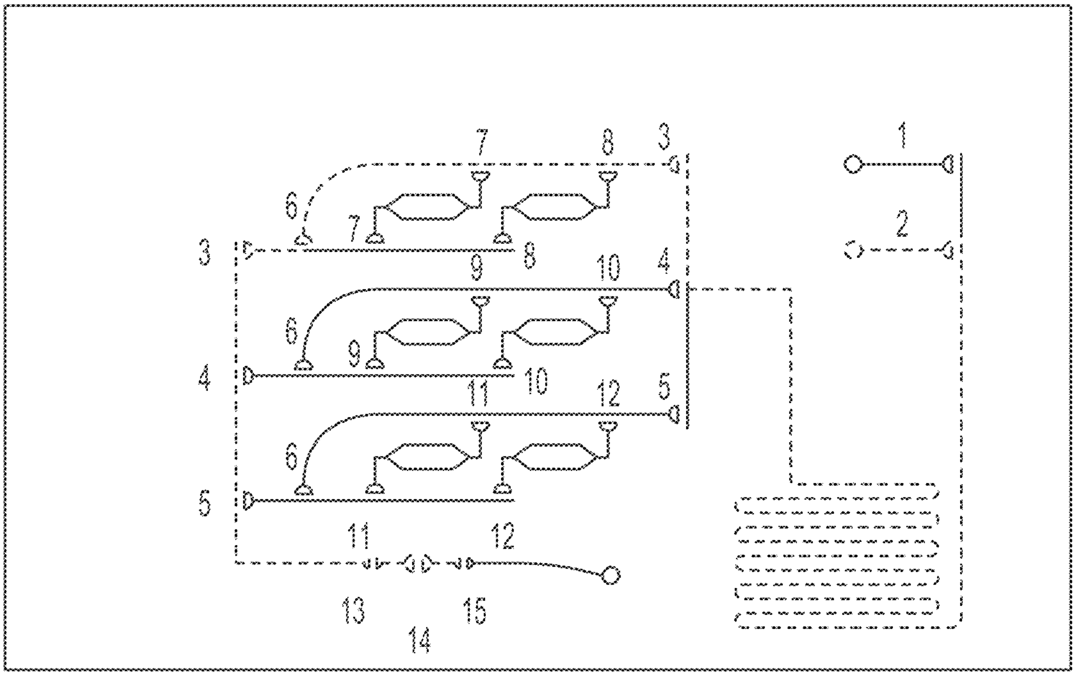
Figure 6G:
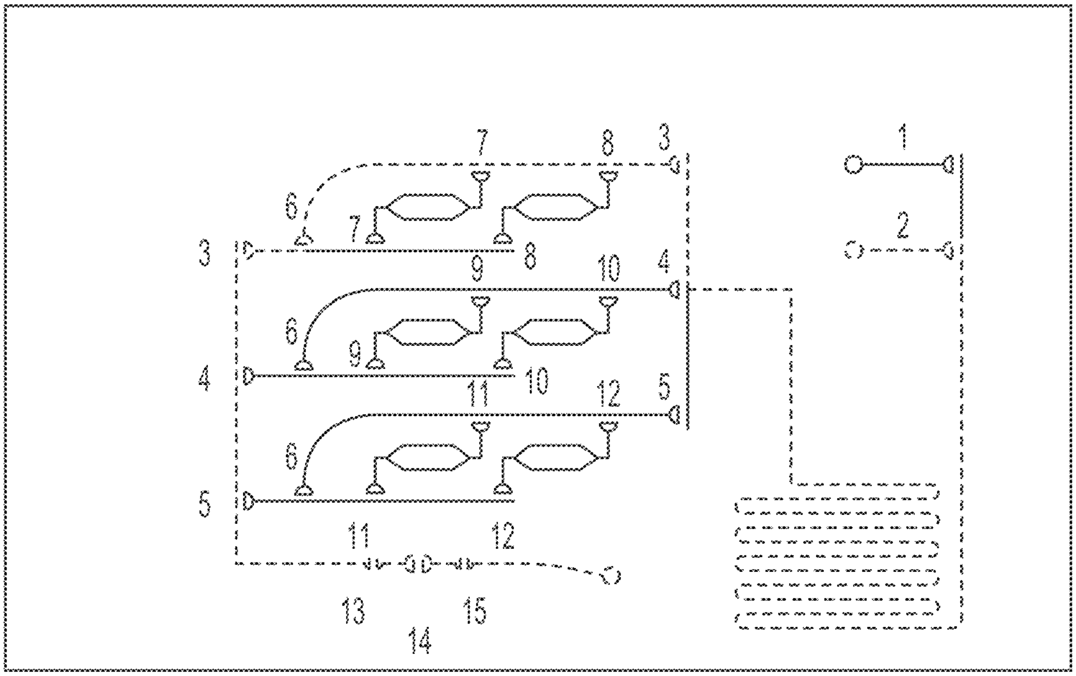
Figure 6H:
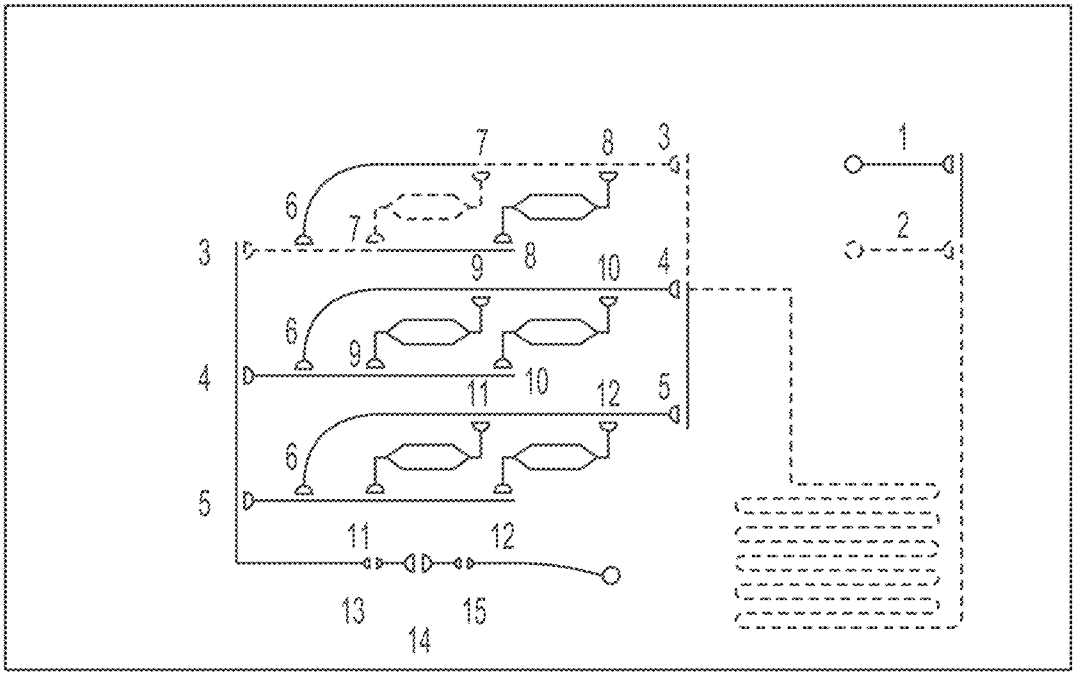
Figure 6I:
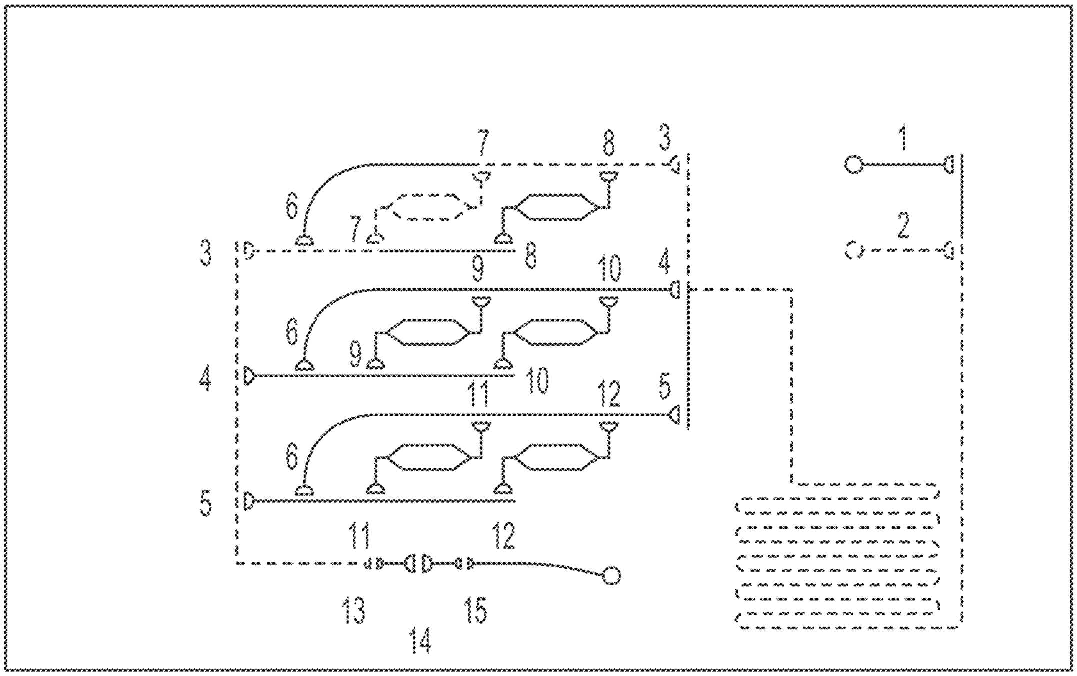
Figure 6J:
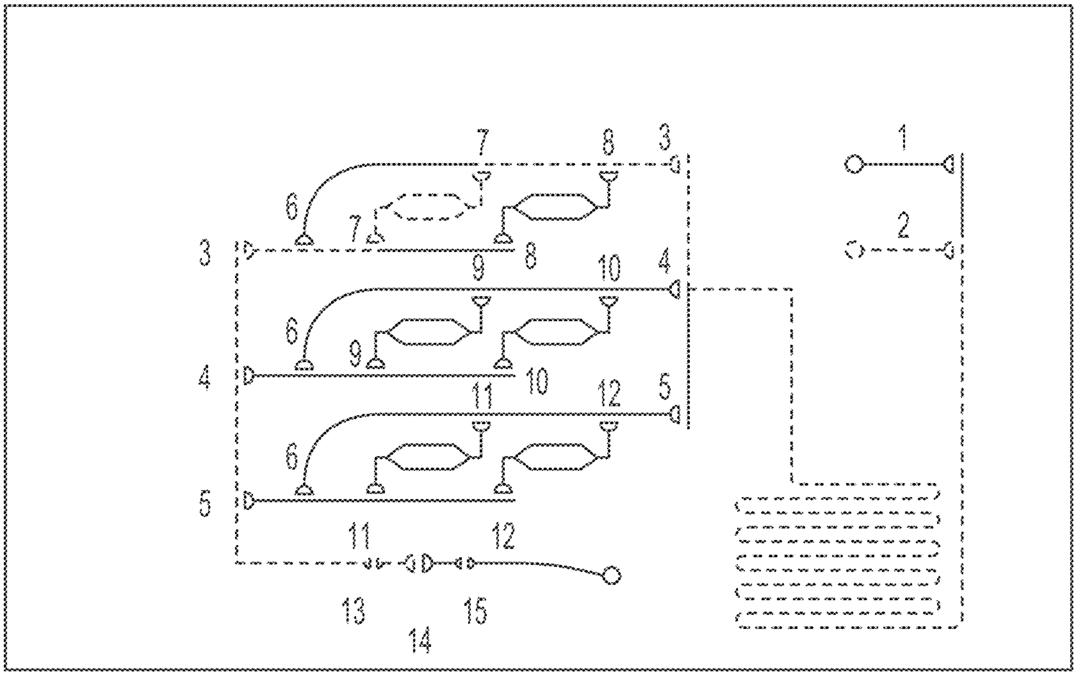
Figure 6K:
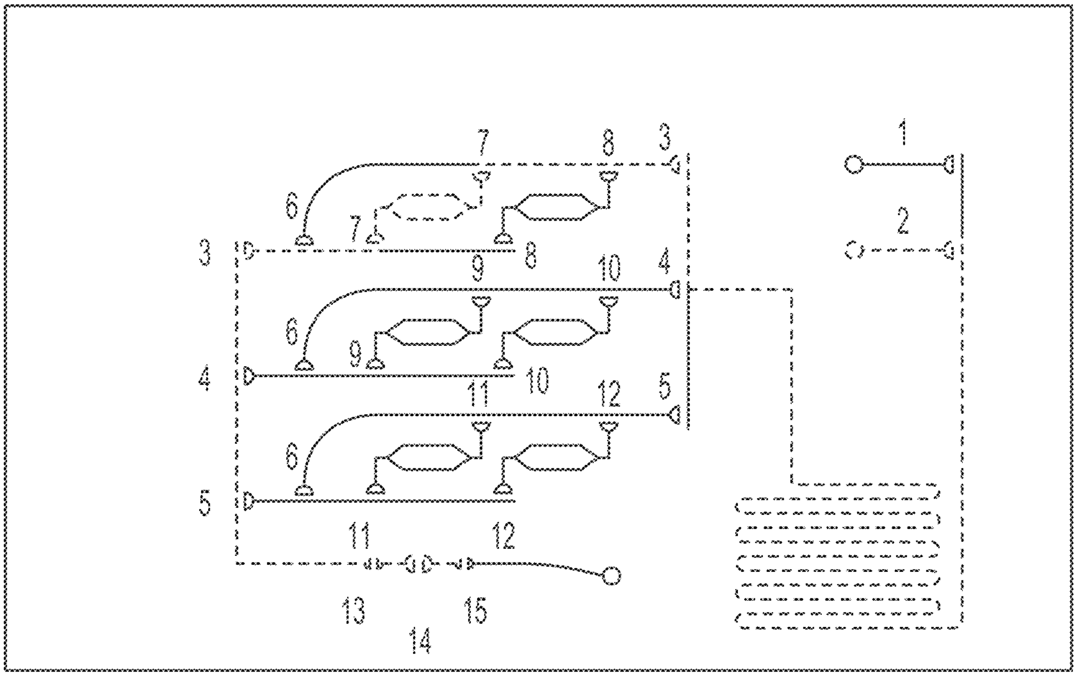
Figure 6L:
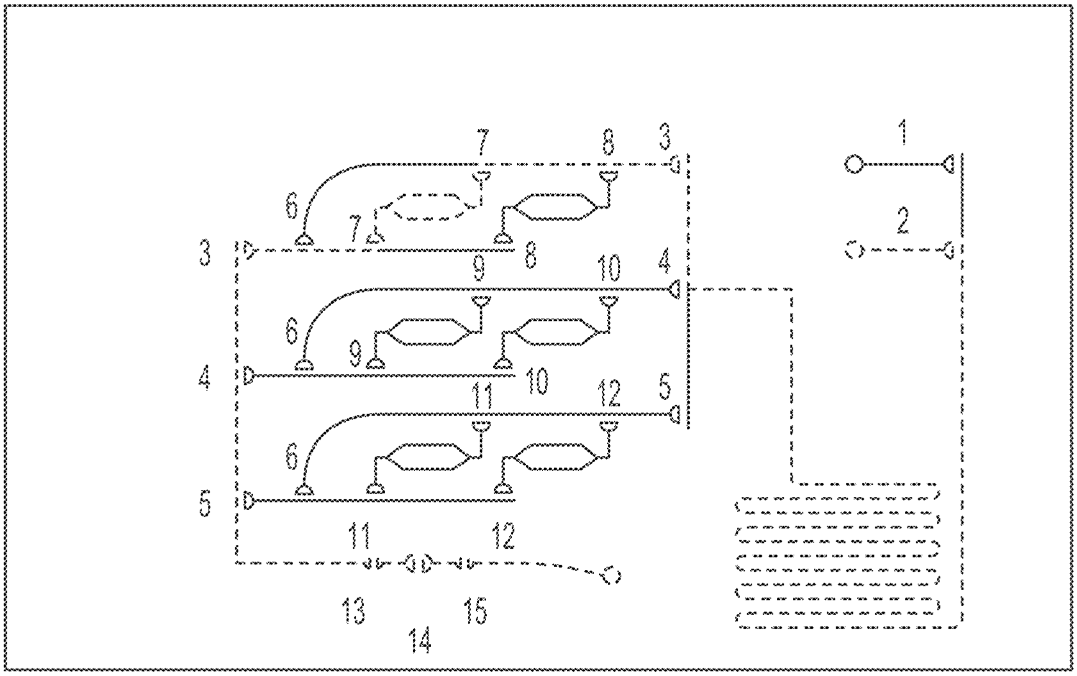
Figure 6M:
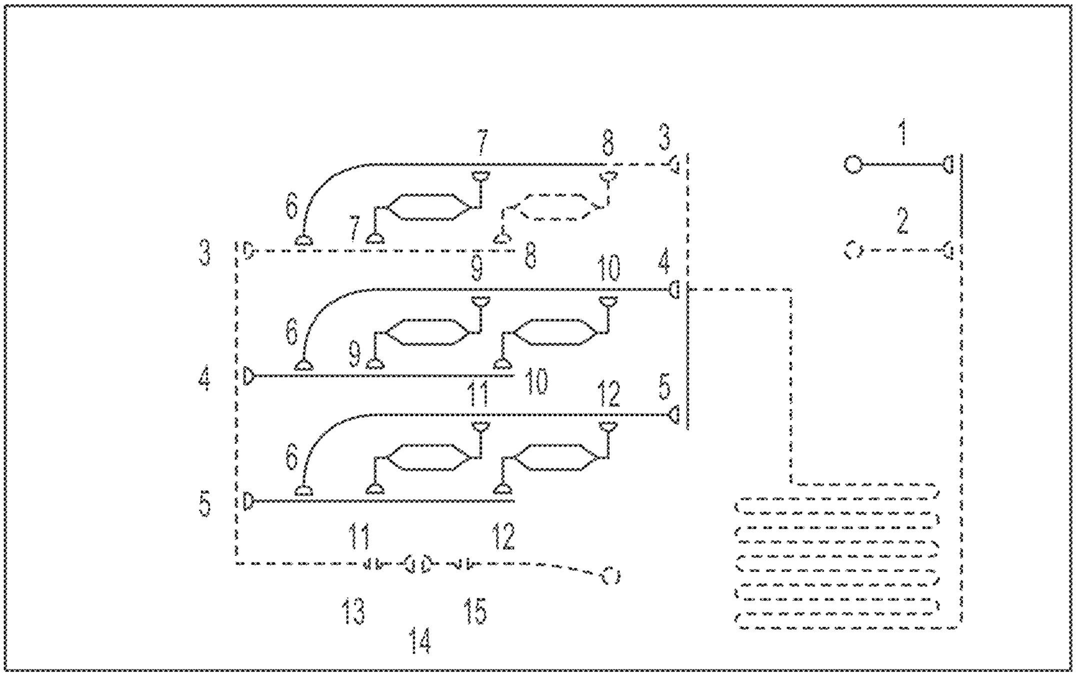
Figure 6N:
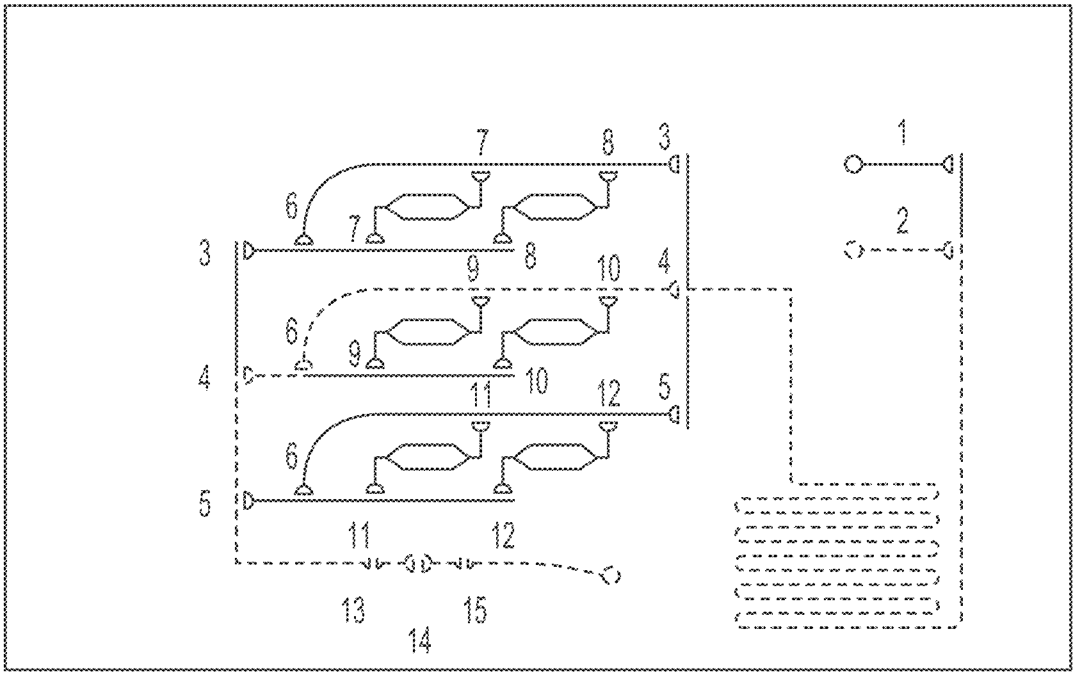
Figure 6O:
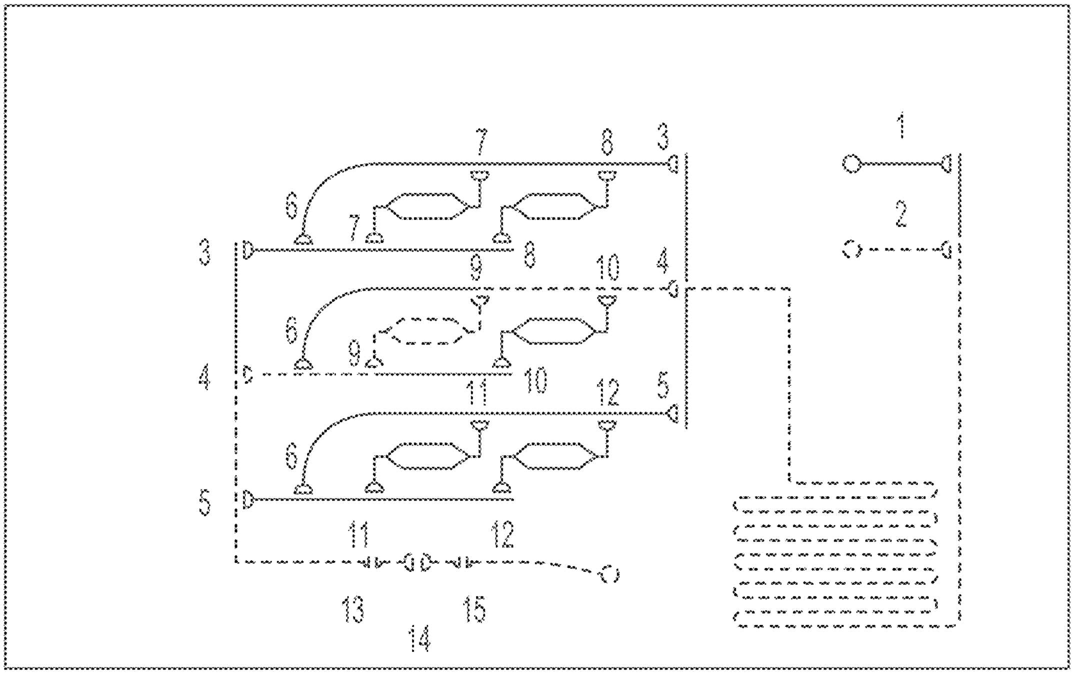
Figure 6P:
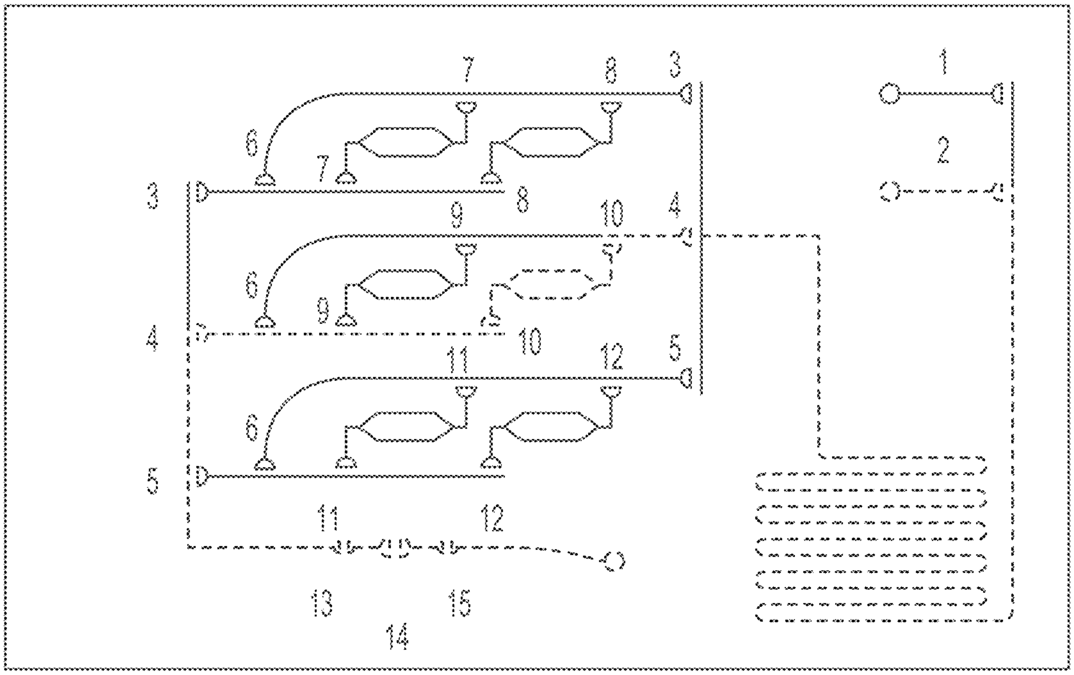
Figure 6Q:
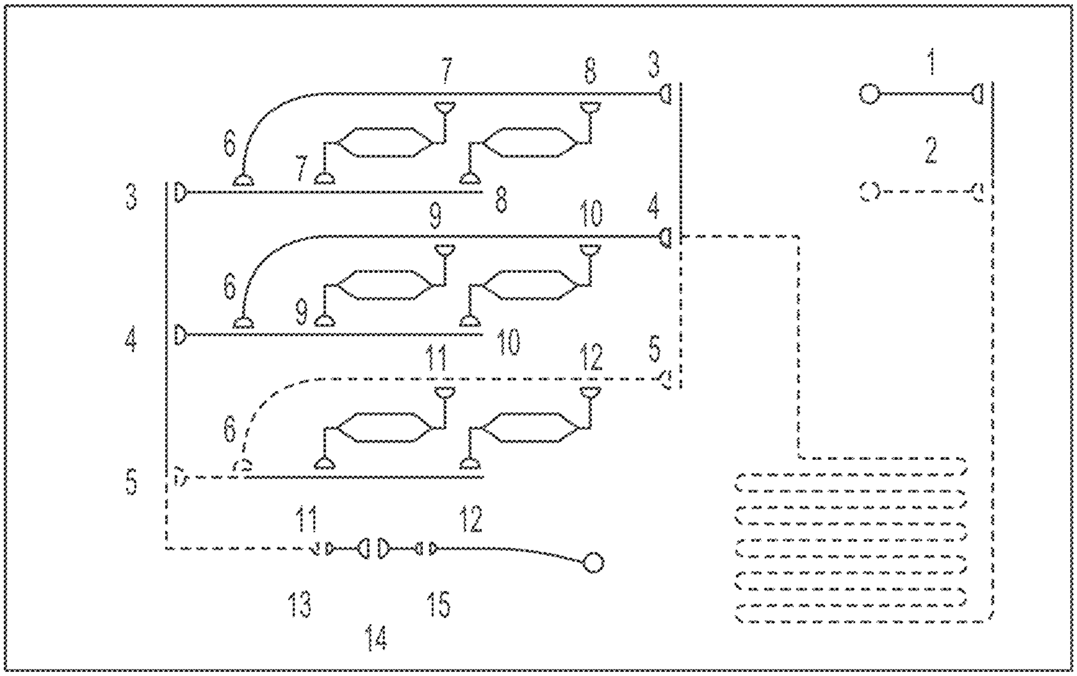
Figure 6R:
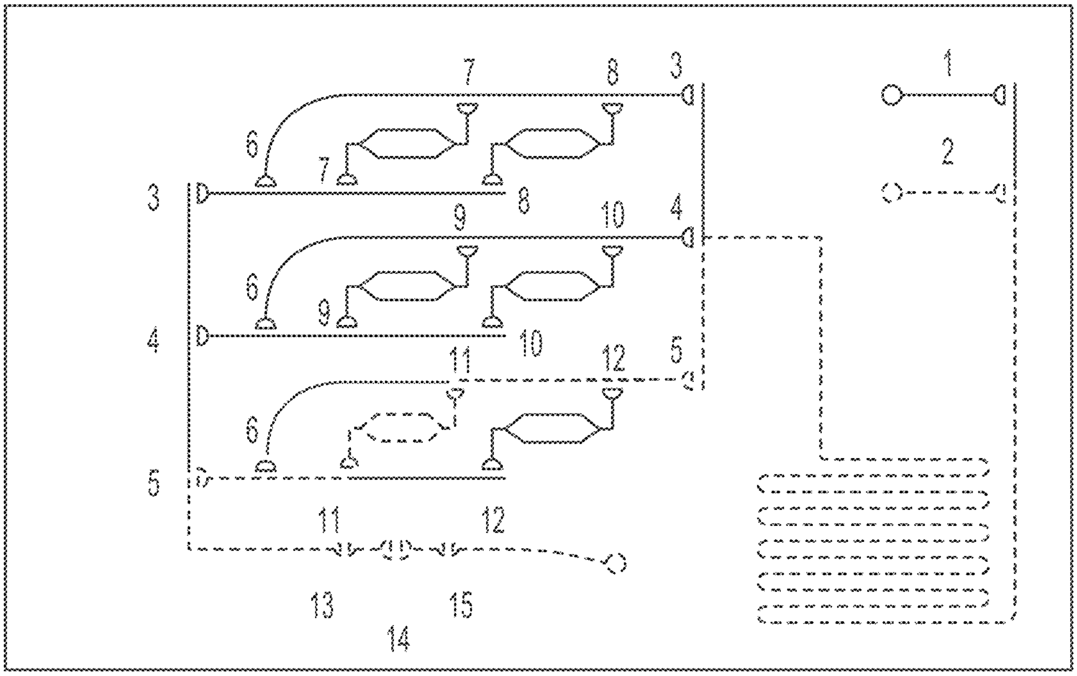
Figure 6S:
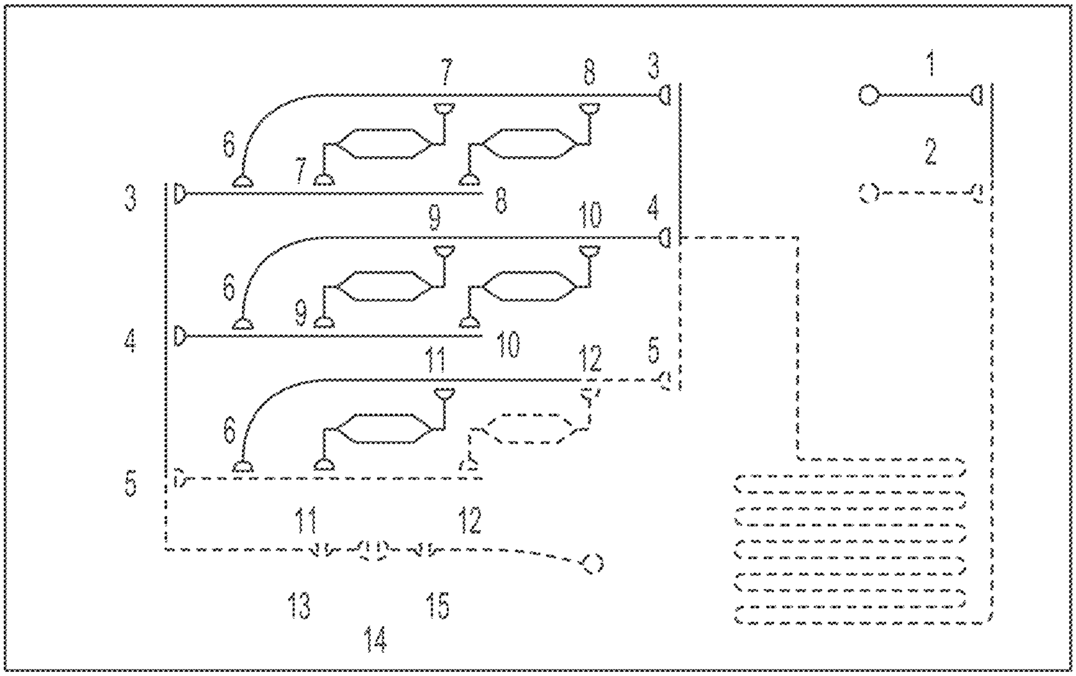
Figure 6T:
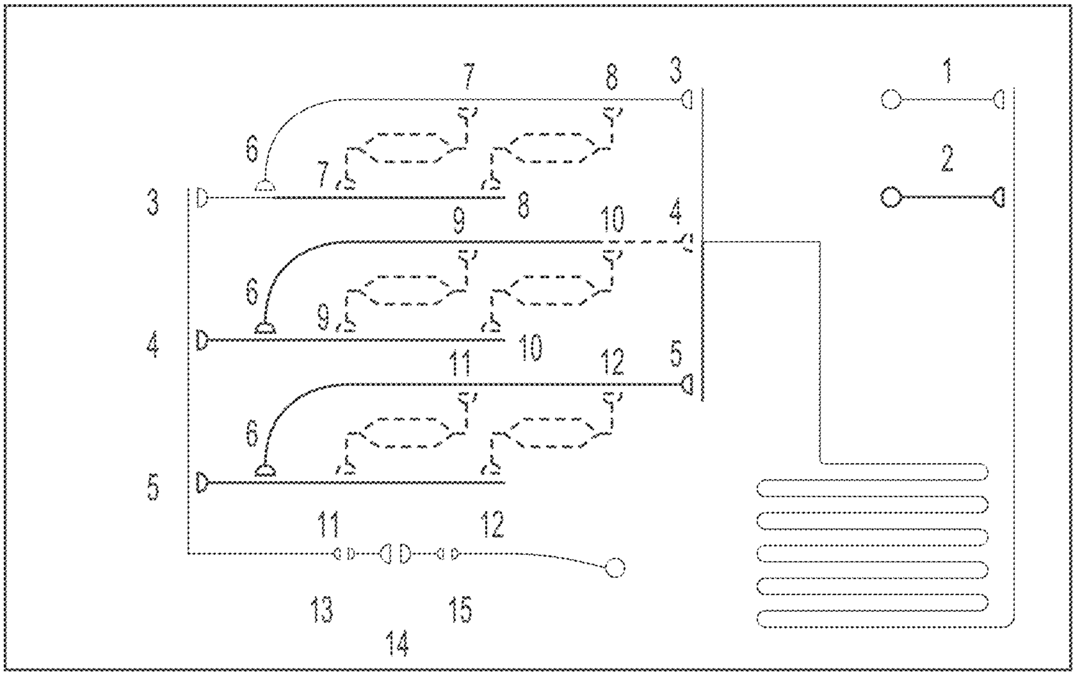
Figure 6U:
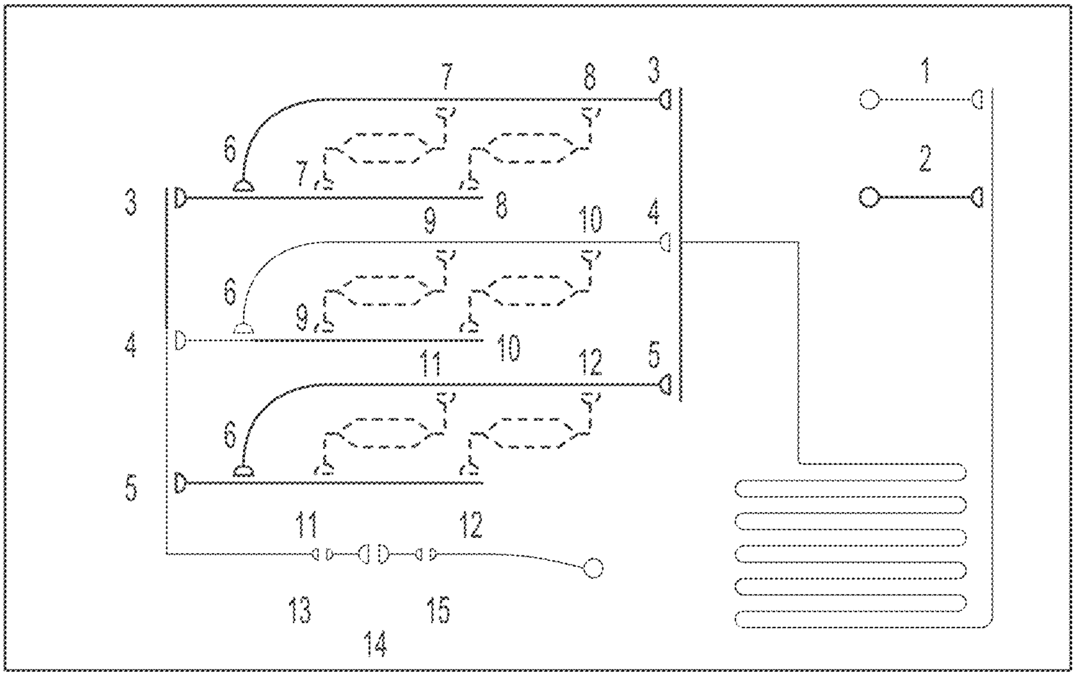
Figure 6V:
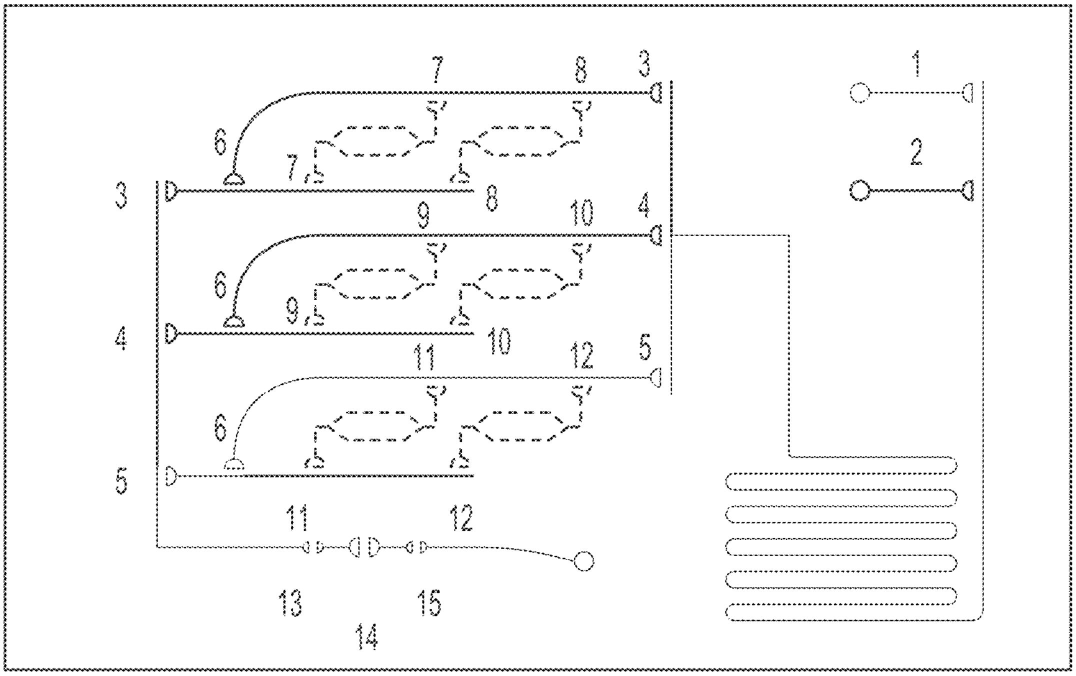

FIGS. 6A-6V depict schematic views of a fluid (e.g., cell suspension) flowing through a microfluidics layer of a multiwell plate device having individually-addressable wells, in accordance with some embodiments. In some embodiments, FIGS. 6A-6V may depict an automated cell loading protocol and rinsing of a chip. Each of FIGS. 6A-6V shows the state of the flow of fluid through the multiwell plate device at a different chronological point in time. In FIGS. 6A-6V, the schematic views show that the multiwell plate depicted comprises six hexagonal wells connected by microfluidic channels; each of the wells has an inlet channel and an outlet channel. Flow through the microfluidic channels is controlled by a plurality of numbered valves, represented by triangles in the schematics of FIGS. 6A-6V, and the channels lead from two fluid inputs near valves 1 and 2 to a single output near valve 15. The chronological process shown in FIGS. 6A-6V depicts how each of the wells in a multiwell device may be individually addressed to control the flow of fluid to any specific desired one of the wells. Taken together, FIGS. 6A-6V may depict a process for automated cell seeding and subsequent media perfusion to clear the channels of excess cell suspension, in accordance with some embodiments.

In each of FIGS. 6A-6V, valves 13, 14, and 15 may constitute a micropump that creates a vacuum force to pull fluid from the inlets near valves 1 and 2 through one or more of the intermediate microchannels toward the outlet near valve 15.

In FIG. 6A, valve 2 may be opened to allow the flow of fluid from the inlet to the right of valve 2, as shown by the dashed line representing the channel. In some embodiments, the inlet next to valve 2 may be configured to provide cell suspension, while the inlet next to valve 1 may be configured to media exchange fluid. In some embodiments, the two inlets may be configured to provide flow of any two different fluids. In some embodiments, more than two inlets may exist, and each may be configured to provide different fluids. In some embodiments, the same fluid may be provided by two or more fluids.

In FIG. 6B, valve 3 may be opened to select the upper row of two wells and to fill the channel between the inlet nearest valve 2 and the upper row with cell suspension. (As used with reference to FIGS. 6A-6V the "upper" row refers to the row shown at nearest the top of the illustration, as oriented by the direction of the text of the reference numerals. Similarly, the "lower" row will refer to the row nearest the bottom of the illustration.) In some embodiments, valve 3 may remain open until all fluid operations in the first row have been done, and then it may be closed and valve 4 may open the next row.

In FIG. 6C, valve 6 may be opened to perfuse the any one or more of the rows by allowing the flow of cell suspension, media, and/or reagents along the channel above the wells in any one or more of the rows. In some embodiments, valve 6 may open each valve with the same number. However, since only the first row is opened by valve 3, fluid may only be transported through the upper row. In some embodiments, selecting valve 4 in combination may allow fluid only to be transported through row 2, and so forth.

In FIG. 6D, the cell suspension may flow from row 1 through the leftmost bus valve of valve 3, down toward valve 13. In some embodiments, valve 3 comprises two bus-valves that may both open (and/or close) simultaneously. Note that certain valves in FIGS. 6A-6V are numbered so as to indicate that two different bus-valves correspond to the same valve number. In these cases, both bus valves may be configured to be opened and/or closed simultaneously with one another, such as by being actuated by a single pneumatic action. In some embodiments, configuring more than one bus valve to be actuated by a single pneumatic action as part of a single overall valve may save space on pneumatic connections, and for example may allow a row to be selected (e.g., by having its upstream and downstream bus valves simultaneously opened or simultaneously closed) via a single pneumatic input.

In FIG. 6E-6G, valves 13, 14, and 15 are opened in sequence, such that the cell suspension flows through them toward the outlet near valve 15. As mentioned above, valves 13, 14, and 15 may constitute a micropump that creates a vacuum force within the fluidic channel to pull fluid from the inlets near valves 1 and 2 through one or more of the intermediate microchannels toward outlet 15. The operation of valves 13-15 as a micropump will be discussed below in greater detail with respect to FIG. 7. In some embodiments, several pump-strokes of the micropump may be required in order to fill channels and ensure equal cell distribution.

In FIG. 6H, after the channel above the upper row has been perfused, valve 7 may be opened to cause cell suspension to flow from the channel above the uppermost row into the well corresponding to valve 7, and out of the well and into the microchannel below the uppermost row of wells and toward the leftmost bus valve of valve 3, which may have remained open since the step shown in FIG. 6B. Note that, in FIG. 6H, the area between the upper side of well 7 and valve 6 is no longer shown in dashed lines. This is not intended to indicate that the area is no longer filled with fluid; rather, it is intended merely to highlight the areas newly shown in dashed lines, where fluid flow is new. In some embodiments, the areas previously shown in dashed lines may still be fully filled with fluid. The same convention is applied throughout several of the following figures included in FIGS. 6H-6V.

In FIG. 6I, the cell suspension may flow from the well corresponding to valve 7 through the leftmost bus valve of valve 3, down toward valve 13.

In FIG. 6J-6L, valves 13, 14, and 15 are opened in sequence, such that the cell suspension, media, and/or reagents flows through them toward the outlet near valve 15.

In FIG. 6M, after the well corresponding to valve 7 has been filled with cell suspension, media, and/or reagents, then valve 8 may be opened to begin filling the well associated with valve 8, to cause cell suspension, media, and/or reagents to flow from the channel above the uppermost row into the well corresponding to valve 8, and out of the well and into the microchannel below the uppermost row of wells and toward the leftmost bus valve of valve 3, which may have remained open since the step shown in FIG. 6B. In some embodiments, valve 7 may be closed. In some embodiments, a multiwell device may be configured such that all previous wells are closed before a new well is opened to be filled with fluid and/or cell suspension, media, and/or reagents.

In FIG. 6N, after all of the wells in the uppermost row have been filled, wells in the middle row may be filled. As shown in FIG. 6N, valve 4 may be opened to select the middle row of wells and to perfuse the middle row by allowing the flow of cell suspension along the channel above the wells in the middle row.

In FIG. 6O, after the channel above the middle row has been perfused, valve 9 may be opened to cause cell suspension to flow from the channel above the middle row into the well corresponding to valve 9, and out of the well and into the microchannel below the middle row of wells and toward the leftmost bus valve of valve 4, which may have remained open since the step shown in FIG. 6N.

In FIG. 6P, after the well corresponding to valve 9 has been filled with cell suspension, media, and/or reagents, then valve 10 may be opened to begin filling the well associated with valve 10, to cause cell suspension, media, and/or reagents to flow from the channel above the middle row into the well corresponding to valve 10, and out of the well and into the microchannel below the middle row of wells and toward the leftmost bus valve of valve 4, which may have remained open since the step shown in FIG. 6N. In some embodiments, valve 9 may be closed.

In FIG. 6Q, after all of the wells in the middle row have been filled, wells in the lower row may be filled. As shown in FIG. 6Q, valve 5 may be opened to select the lower row of wells and to perfuse the lower row by allowing the flow of cell suspension, media, and/or reagents along the channel above the wells in the lower row.

In FIG. 6R, after the channel above the lower row has been perfused, valve 11 may be opened to cause cell suspension, media, and/or reagents to flow from the channel above the lower row into the well corresponding to valve 11, and out of the well and into the microchannel below the lower row of wells and toward the leftmost bus valve of valve 5, which may have remained open since the step shown in FIG. 6Q.

In FIG. 6S, after the well corresponding to valve 11 has been filled with cell suspension, then valve 12 may be opened to begin filling the well associated with valve 12, to cause cell suspension, media, and/or reagents to flow from the channel above the lower row into the well corresponding to valve 12, and out of the well and into the microchannel below the lower row of wells and toward the leftmost bus valve of valve 5, which may have remained open since the step shown in FIG. 6Q. In some embodiments, valve 11 may be closed.

In FIG. 6T, after each of the wells (or all of the desired wells) in the plate have been addressed to be filled with cell suspension, media, and/or reagents, valve 2 may be closed and valve 1 may be opened. Accordingly, the inlet corresponding to valve 2 may be blocked such that cell suspension, media, and/or reagents may no longer flow into the microchannels, while the inlet next to valve 1 may be fluidly connected to the microchannels by the opening of valve 1 such that fluid media may flow from inlet 1 through the microchannels. In some embodiments, media determined in accordance with the cell suspension used may be selected, and the media may be used to rinse the microchannels.

As shown in FIGS. 6T-6V, the rinsing media may first flow through the channels of the uppermost row, then through the channels of the middle row, then through the channels of the lowermost row. In order to enable this flow process, valve 3 may first be opened; then valve 3 may be closed and valve 4 may be opened; then valve 4 may be closed and valve 5 may be opened. In FIGS. 6T-6V, flow of rinsing media through the various channels is shown by the use of thinner lines.

After each of the above steps in which one or more valve is opened or closed, the system may be configure to pause for a predefined period of time and/or to execute a predefined number of pump-strokes via a micropump. In some embodiments, different rows, channels, and/or wells may be known to take a longer amount of time or a greater number of strokes to fill/perfuse/evacuate/rinse, so the system may pause for different amounts of time and/or execute different predefined numbers of pump strokes at different steps of the above process. In some embodiments, one or more sensors of the system may be used to determine whether the desired perfusion, well-filling, evacuation, and/or rinsing has occurred, and the sensors may be used to trigger the system to advance to the next step, for example by opening or closing a next valve.

In some embodiments, after the rows are rinsed, the system may pause for a predefined period of time (see FIG. 6W below) defined by a user input and/or a characterized cell line adhesion profile. After expiration of the predefined adhesion time, the system may change the protocol to automated cell culture and may perfuse the wells in predefined intervals.

In some embodiments of the layout shown in FIGS. 6A-6V, channel width to the right (e.g., upstream) of the channels above the rows of wells may be 500 μm, while channel width to the left (e.g., downstream) of the beginning of the channels above the rows of wells may be 250 μm. In some embodiments, different channel widths may have different flow speed at the same micropump actuation cycle.

In some embodiments, the layout and change in channel width shown in FIGS. 6A-6V may allow incoming media to be reduced in flow speed so that it can stabilize in temperature and so that any unintentionally introduced air-bubbles can be captured in a degasser in a layer above the fluid routing layer at a location above the serpentine portion of the microfluidic channel. In some embodiments, a micro-degasser may be incorporated in a fluid control layer. In some embodiments, the degasser may comprise a grid disposed in a pneumatic layer over a fluid routing layer included in the layout depicted in FIGS. 6A-6V. By applying a vacuum to the grid (e.g., a constant vacuum), gas bubbles may be extracted from the serpentine channel beneath the grid.

Heated and air-bubble free media may then be dispersed into the individual row channels, where the media may then introduced into the individual wells. In some embodiments, one or more additional degassers (e.g., secondary degassers) may further be included such that gas bubbles may be extracted at the location of one or more individual wells, or at the location of one or more inlets to one or more individual wells.

Figure 6W:
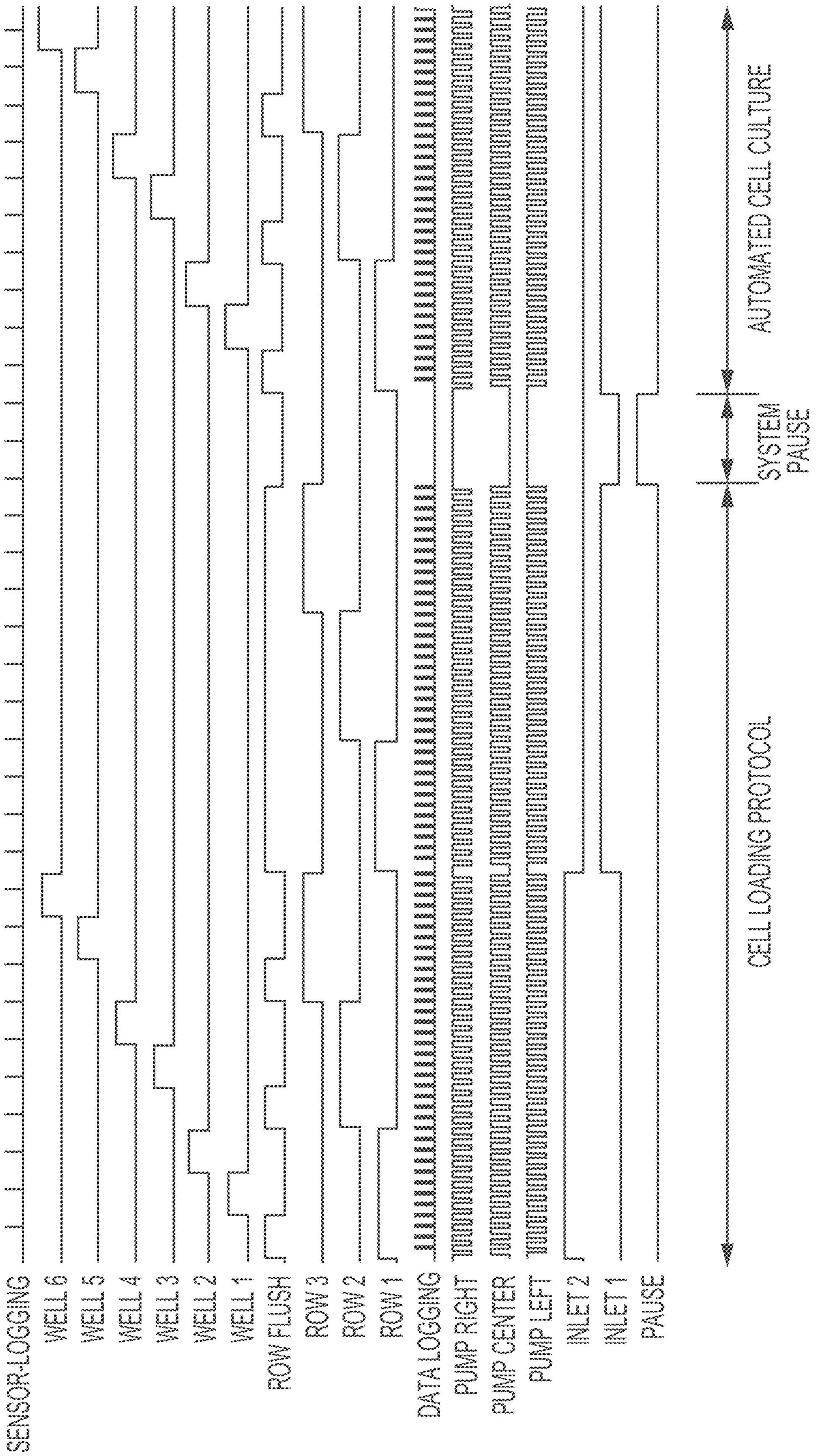

FIG. 6W depicts a graphical representation of the operation of various components or features of a multiwell system over time. In some embodiments, the multiwell system operated in accordance with FIG. 6W may be the multiwell system schematically depicted in FIGS. 6A-6V. FIG. 6W shows a chronological representation of 18 components or features of a multiwell device over time. The 18 horizontal lines in FIG. 6W each represent the state of a respective component over time during operation of the device, where the step-function changes in each line represents an event or occurrence or change in state of the respective component or feature. The operation of each of the 18 components or features is shown in chronological synchronization.

The first (top-most) line in FIG. 6W represents operation of a sensor logging function of the multiwell device and/or docking station 100 and or portable manifold connector 1200. At each of the spikes in the line, the system may log, record, store, and/or transmit information regarding one or more sensors associated with the device at those times.

The second line in FIG. 6W represents operation of a valve associated with well 6; in some embodiments, this may represent valve 12 as discussed above with respect to FIGS. 6A-6V. Where the line is shown in a raised position, the valve may be in an open position during those times.

The third line in FIG. 6W represents operation of a valve associated with well 5; in some embodiments, this may represent valve 11 as discussed above with respect to FIGS. 6A-6V. Where the line is shown in a raised position, the valve may be in an open position during those times.

The fourth line in FIG. 6W represents operation of a valve associated with well 4; in some embodiments, this may represent valve 10 as discussed above with respect to FIGS. 6A-6V. Where the line is shown in a raised position, the valve may be in an open position during those times.

The fifth line in FIG. 6W represents operation of a valve associated with well 3; in some embodiments, this may represent valve 9 as discussed above with respect to FIGS. 6A-6V. Where the line is shown in a raised position, the valve may be in an open position during those times.

The sixth line in FIG. 6W represents operation of a valve associated with well 2; in some embodiments, this may represent valve 8 as discussed above with respect to FIGS. 6A-6V. Where the line is shown in a raised position, the valve may be in an open position during those times.

The seventh line in FIG. 6W represents operation of a valve associated with well 1; in some embodiments, this may represent valve 7 as discussed above with respect to FIGS. 6A-6V. Where the line is shown in a raised position, the valve may be in an open position during those times.

The eighth line in FIG. 6W represents operation of a row flush function. Where the line is shown in a raised position, the system may be performing a row flush function during those times. In some embodiments, row flushing may comprise causing a corresponding row valve to remain is opened while the well valves in that row remain closed. Opening the flush valve may thus allow the channel to be rinsed and cleaned of cell suspension, media, and/or reagent that was previously introduced into the channel before. In some embodiments, channels may be rinsed prior to addressing individual wells, in order to deliver fresh and untainted media to the wells.

The ninth line in FIG. 6W represents operation of valves associated with row 3; in some embodiments, this may represent valve 5 as discussed above with respect to FIGS. 6A-6V. Where the line is shown in a raised position, the valve may be in an open position during those times.

The tenth line in FIG. 6W represents operation of valves associated with row 2; in some embodiments, this may represent valve 4 as discussed above with respect to FIGS. 6A-6V. Where the line is shown in a raised position, the valve may be in an open position during those times.

The 11th line in FIG. 6W represents operation of valves associated with row 1; in some embodiments, this may represent valve 3 as discussed above with respect to FIGS. 6A-6V. Where the line is shown in a raised position, the valve may be in an open position during those times.

The 12th line in FIG. 6W represents operation of a data logging function of the multiwell device. At each of the spikes in the line, the system may log, record, store, and/or transmit information regarding associated with the device at those times.

The 13th, 14th, and 15th lines in FIG. 6W represents operation of a right, center, and left valve, respectively, where the three valves together form a micro-pump, as discussed in further detail below with respect to FIG. 7. Where each of the lines is shown in a raised position, the respective valve may be in an open position during those times.

The 16th line in FIG. 6W represents operation of a valve associated with inlet 2; in some embodiments, this may represent valve 2 as discussed above with respect to FIGS. 6A-6V. Where the line is shown in a raised position, the valve may be in an open position during those times.

The 17th line in FIG. 6W represents operation of a valve associated with inlet 1; in some embodiments, this may represent valve 1 as discussed above with respect to FIGS. 6A-6V. Where the line is shown in a raised position, the valve may be in an open position during those times.

The 18th bottom-most line in FIG. 6W represents a pause function of a multiwell device. Where the line is shown in a raised position, the valve device may be in a pause state during those times.

As shown by the annotation at the bottom of the figure, FIG. 6W represents a cell loading protocol stage, followed by a system pause stage, followed by an automated cell culture stage for media exchange within the individual wells that have been seeded with cells in the first stage.

In some embodiments, microfluidic-enabled devices and/or systems disclosed herein may be configured to perform automated addition of one or more compounds to cells. In some embodiments, operation of drug or reagent delivery may be similar to the protocol explained above in FIGS. 6A-6W for cell loading and/or media exchange. In some embodiments, for drug or reagent delivery, an appropriate input port besides a media and/or cell loading port may be selected. In some embodiments, dilution and gradient generation may be achieved by targeted well addressing and/or dilution through active microfluidic mixing in channels with media.

In some embodiments, microfluidic-enabled devices and/or systems disclosed herein may be configured to perform automated exchange of cell culture media.

In some embodiments, microfluidic-enabled devices and/or systems disclosed herein may be configured to perform automated trypsinization of cultured cells. In some embodiments, for example, the addition of trypsin may cause cells in a multiwell device to detach and then wash out from the device on media exchange.

Figure 7:
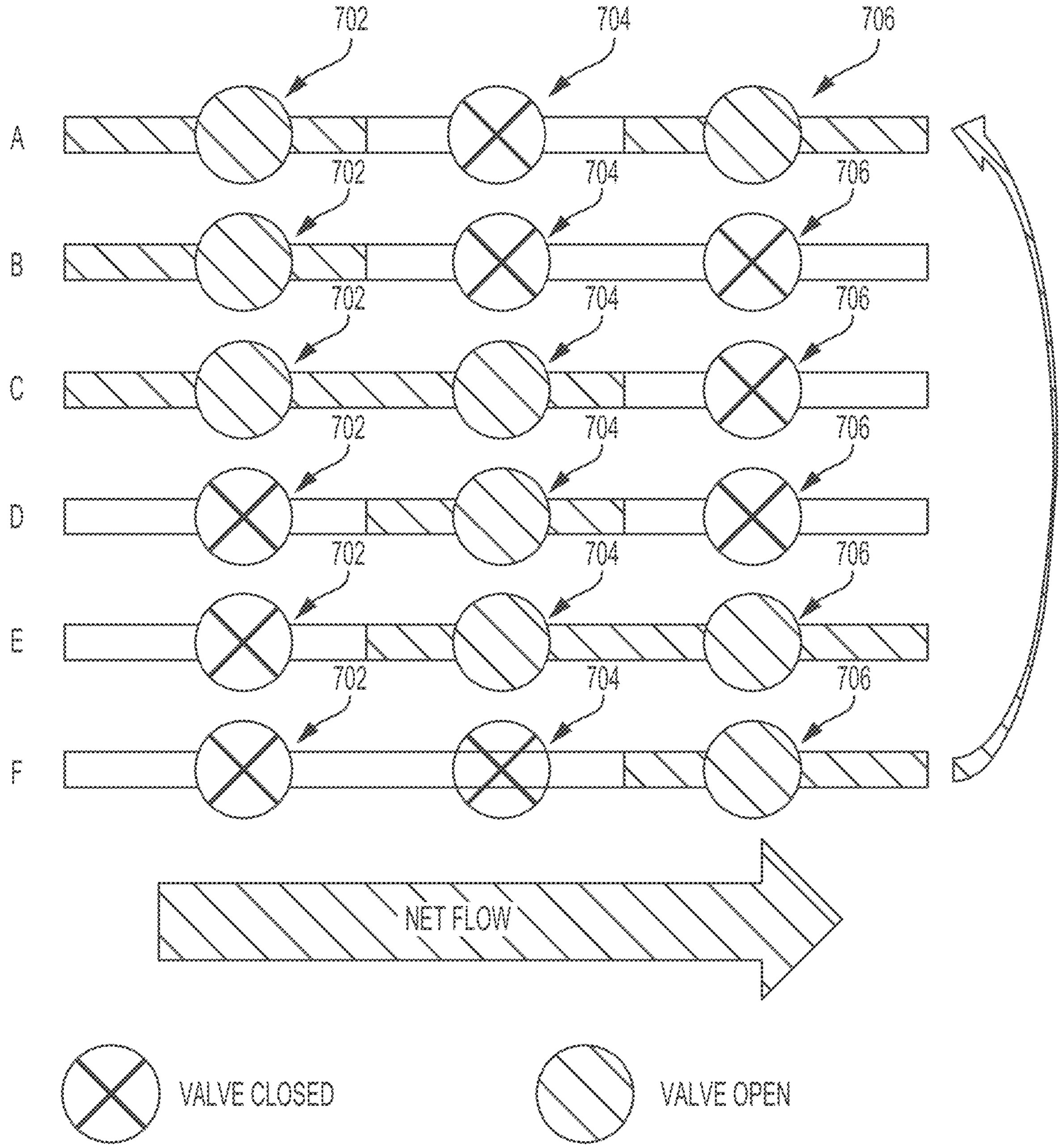
FIG. 7 schematically depicts six different stages of micropump operation using a three-valve structure, in accordance with some embodiments.

FIG. 7 schematically depicts six different stages of micro-pump operation using a three-valve structure, in accordance with some embodiments. In some embodiments, the micro-pump comprises valves 702, 704, and 706, with the flow of fluid from left to right in the figure, flowing from valve 702 to valve 706. In some embodiments, valves 702, 704, and 706 may correspond respectively to valves 13, 14, and 15 as discussed above with respect to FIGS. 6A-6V. In some embodiments, valves 702, 704, and 706 may share some or all characteristics in common with any one or more other valves discussed herein.

In FIG. 7, six stages labeled A-F are shown from top to bottom in the figure, with the stages progressing chronologically from A to F.

In stage A, valve 702 is open, valve 404 is closed, and valve 706 is open.

In stage B, valve 702 is open, valve 404 is closed, and valve 706 is closed.

In stage C, valve 702 is open, valve 404 is open, and valve 706 is closed.

In stage D, valve 702 is closed, valve 404 is open, and valve 706 is closed.

In stage E, valve 702 is closed, valve 404 is open, and valve 706 is open.

In stage F, valve 702 is closed, valve 404 is closed, and valve 706 is open.

In some embodiments, the six chronological stages shown in FIG. 7 may together constitute a single pump-stroke of the micro-valve formed by valves 702, 704, and 706. Multiwell microfluidic systems discussed herein may, in some embodiments, comprise one or more micro-pumps configured to automatically execute one or more pump-strokes of multi-valve micro-pumps such as the one shown in FIG. 7.

In some embodiments, fluid actuation in microfluidics may be achieved by placing three bus valves in sequence and facilitating a cyclic actuation, as shown in one example by the six chronological stages shown in FIG. 7.

In some embodiments, three parameters may influence fluid flow using micro pumps: (1) geometry of the bus-valves; (2) applied pressure/vacuum to the pneumatics; and (3) step-time/actuation interval.

Regarding geometry of the bus-valves (e.g., size and diameter of the individual valves), smaller valve diameters may have a short actuation time (the time the applied vacuum requires in order to deflect the membrane over/with the gate), and larger valves may require longer actuation time for the membrane to deflect.

Regarding applied pressure/vacuum to the pneumatics, vacuum and pressure settings may be modulated to increase or decrease flow rates as the pneumatic strength directly controls the deflection of the membrane.

Regarding step-time/actuation interval, higher step-times may allow more time for the membrane to deflect, thus creating a larger volume displacement, while lower step-times may allow less time for the membrane to deflect, thus creating a smaller volume displacement. Furthermore, the actuation time may also change the flow-speed pattern in the channels. Since a change in actuation time may result in different flow speeds of the fluid, this effect may be used to control the shear stress directed upon the biological sample by precisely adjusting flow rates. Higher flow rates may create higher shear stress conditions, while lower flow rates may reduce the shear stress. Control over shear stress may be an important factor, for example, for the differentiation of stem cells and or endothelial cells.

Figure 8A:
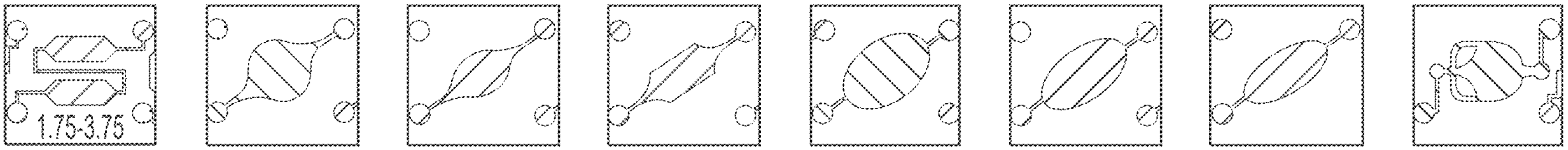
FIGS. 8A-8C different well geometries and tables depicting seeding densities for each of the well geometries, in accordance with some embodiments.
Figure 8B:
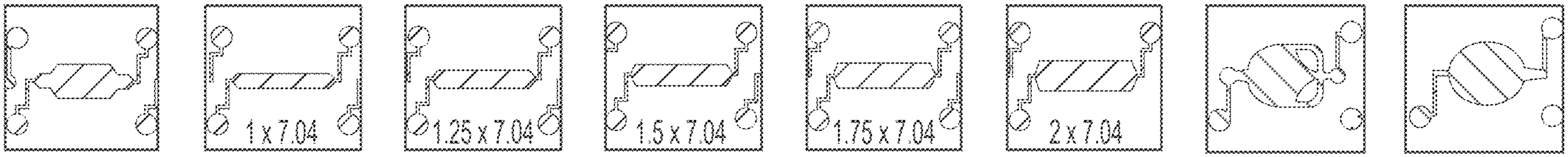
Figure 8C:
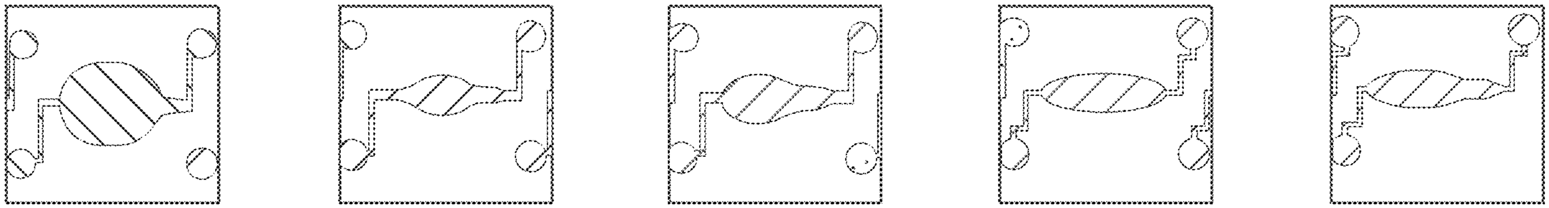

FIGS. 8A-8C depict different well geometries and tables depicting seeding densities for each of the well geometries, in accordance with some embodiments.

In the tables in FIGS. 8A-8C, the first column denotes a number corresponding to a well geometry, the shapes of which are shown across the tops of the figures. The second column denotes the area, in square millimeters, of the corresponding well geometry. The fourth column denotes a seeding density, in cells per well, cells having a diameter of 5 μm, for the corresponding well geometry. The fifth column denotes a seeding density, in cells per well, cells having a diameter of 10 μm, for the corresponding well geometry. The sixth column denotes a seeding density, in cells per well, cells having a diameter of 15 μm, for the corresponding well geometry. The seventh column denotes a seeding density, in cells per well, cells having a diameter of 20 μm, for the corresponding well geometry. The eighth column denotes a seeding density, in cells per well, cells having a diameter of 25 μm, for the corresponding well geometry.

As shown by the different hashing of the well geometries shown across the top of FIGS. 8A-8C, experimental data indicated that, in some embodiments, well geometries 1, 3, 4, 6, 7, 9, 10, 11, 12, 13, 14, 15, 18, 19, 20, and 21 were less likely to experience a buildup of air bubbles; while, in some embodiments, well geometries 2, 5, 8, 15, 16, and 17 were more likely to experience a buildup of air bubbles (or bubbles of other gas or gases). In some embodiments, other well geometries (not shown) were found to be even more likely to experience a buildup of air bubbles; in some embodiments, air bubbles may be more likely to build up in well geometries featuring internal pillars or micro-patterns inside the wells themselves.

In some embodiments, well geometries in which air bubbles are less likely to build up may be preferred. However, use of degassers, especially well-specific microdegassers as discussed herein, may sufficiently alleviate formation of air bubbles such that well geometries susceptible to build-up of air bubbles may be able to be depleted of air bubbles and may therefore be acceptable for various applications.

In some embodiments, in addition to or alternately to selecting and/or optimizing well geometries for minimization of air bubbles, well geometries may be selected and/or optimized for the minimization of "dead spaces" where fluid flow is slow or nonexistent. In some embodiments, elongated well geometries, such as geometry 20 in FIG. 8C, may more effectively minimize dead spaces than more circular geometries such as geometry 17 in FIG. 8C. In some embodiments, well geometries having multiple laterally-distributed inlets, such as geometry 15 in FIG. 8B, may more effectively minimize dead spaces that well geometries with fewer inlets, or with only one inlet.

Figure 9:
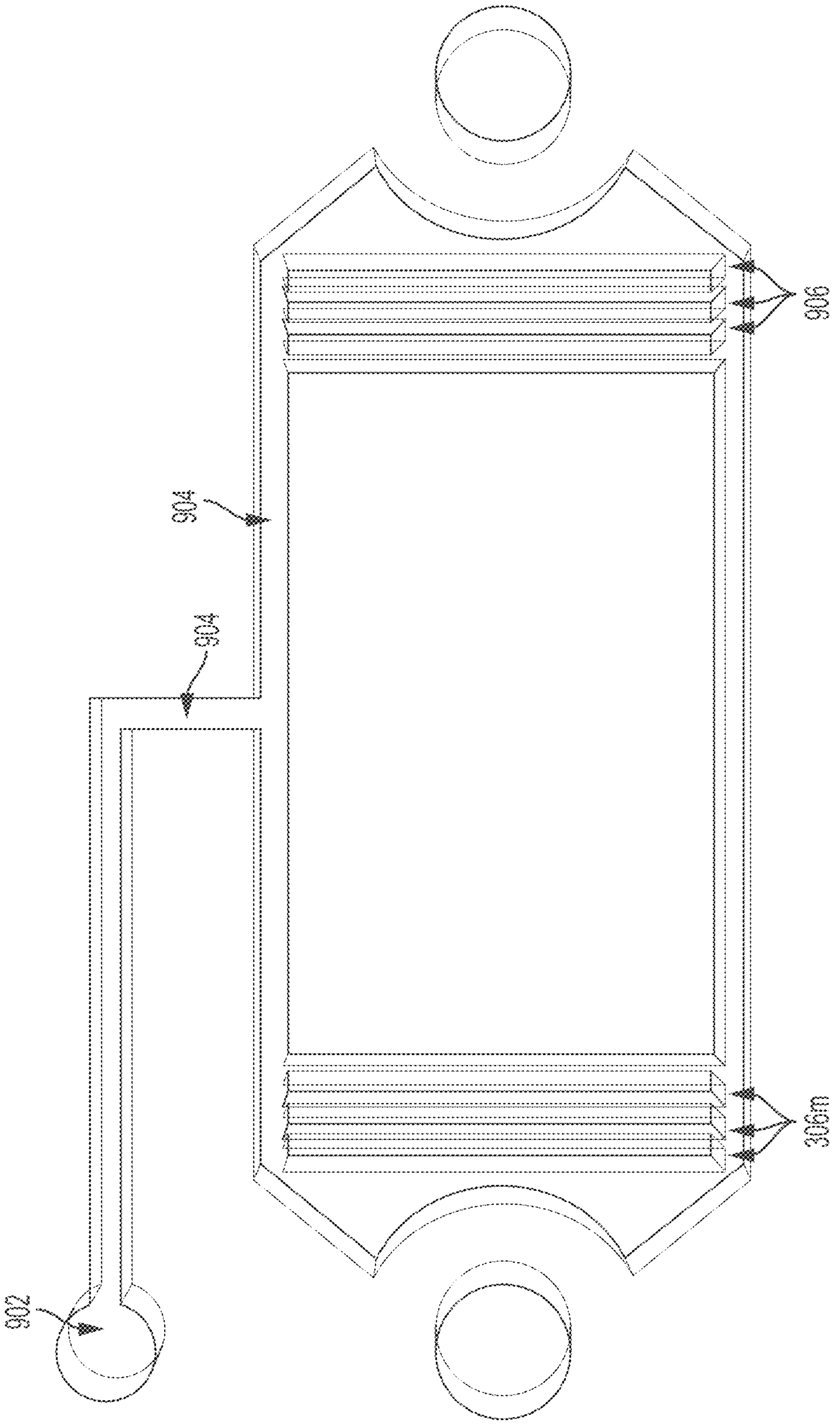
FIG. 9 shows a schematic view of a micro-degasser, in accordance with some embodiments.

FIG. 9 shows a schematic view of a micro-degasser 900, in accordance with some embodiments. In some embodiments, micro-degasser 900 may be included in a microfluidics layer of any of the multiwell devices described herein, and may be configured to remove gas bubbles from one or more microchannels and/or from one or more wells of the device. Micro-degasser 900 may operate in principle same or similar manner as described above regarding the degasser discussed with respect to FIGS. 6A-6V. However, while the degasser discussed above with respect to FIGS. 6A-6V may be a "global" degasser configured to degas a global fluid input line of a multiwell device, micro-degasser 900 may be configured with an adapted geometry for use with an individual well geometry. That is, micro-degasser 900 may be configured to degas a single well of a multiwell device, rather than a global input line corresponding to multiple wells of a multiwell device. The structural components of micro-degasser 900 may comprise a lattice/grid structure that may be the same or similar as a lattice/grid structure used in a primary (e.g., global) media degasser such as the one discussed above. In some embodiments, micro-degasser 900 may be connected in series with the vacuum inlet to the primary degasser. Additional pneumatic channels on top of pneumatic control layer 312 may be routed towards individual via holes that connect corresponding individual micro-degassers above respective wells. In some embodiments, micro-degassers may be located in the same layer as the primary degasser structure; in some embodiments, micro-degassers may be located in a separate layer and/or a separate module of a device from the primary degasser structure. Well-specific micro-degassers such as micro-degasser 900 may rely on the same gas-permeable membrane located between a well layer and fluid routing layer. Since primary degassers and micro degassers may be connected in series, once vacuum is applied to the pneumatic lines it may evacuate any air bubbles delivered to the individual well chambers.

As shown in FIG. 9, degasser 900 may comprise vacuum input hole 902, which may be configured to pneumatically connect to a source of vacuum (such as a pneumatic control layer, or any outside vacuum source). Degasser 900 may further comprise pneumatic channels 904, which may be pneumatic routing structures configured to pneumatically connect input hole 902 to the one or more pillars 906, which may be pillars or other support elements configured to prevent a gas-permeable membrane (through which air may escape from a well into the degasser under the applied vacuum force) from deflecting into the degasser itself.

Figure 10A:
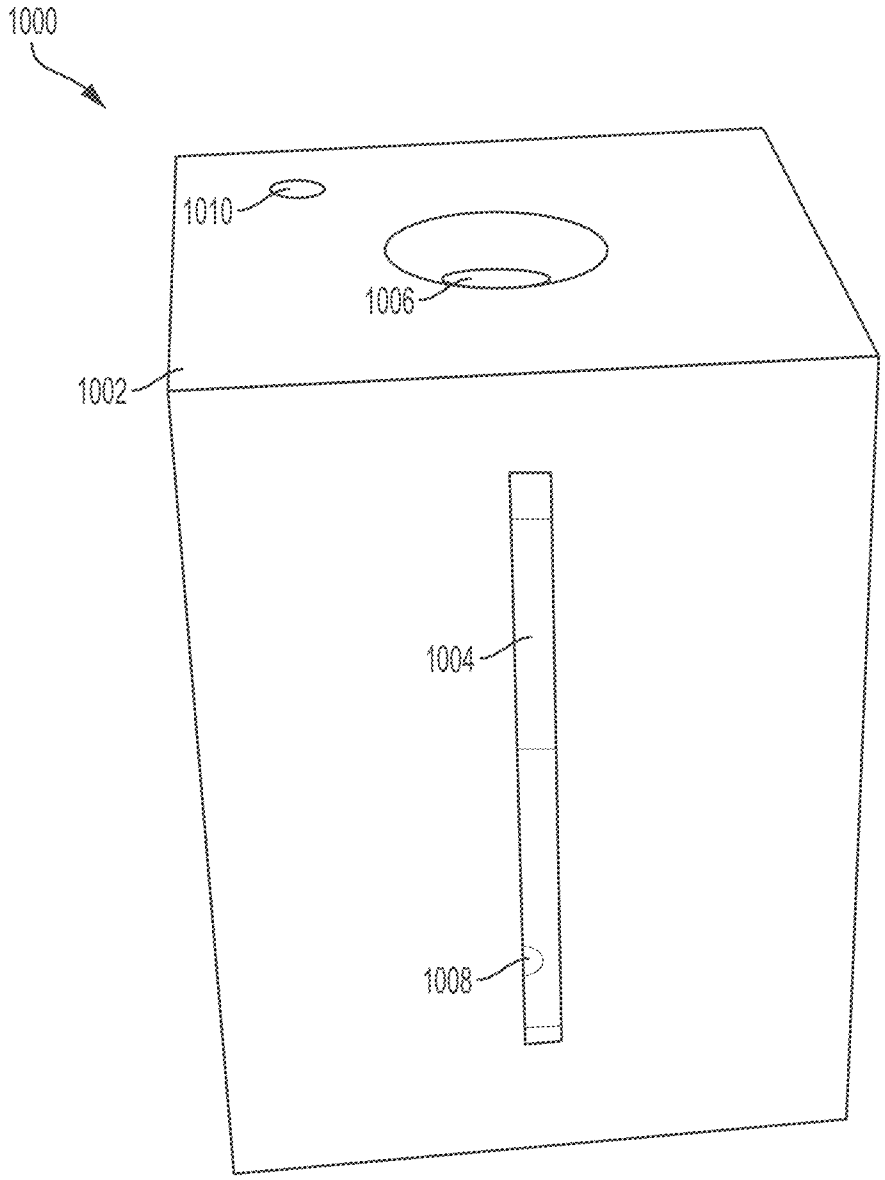
FIGS. 10A & 10B depict two views of a media cartridge for use in a cell culture system, in accordance with some embodiments.
Figure 10B:
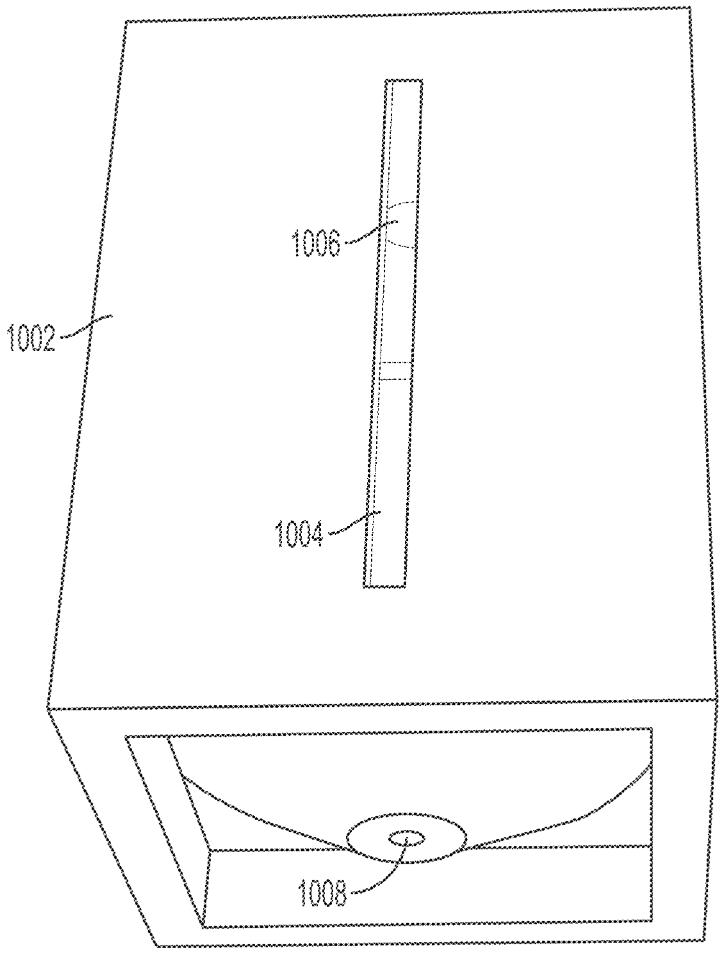

FIGS. 10A & 10B depict two views of a media cartridge 1000 for use in a cell culture system, in accordance with some embodiments. In some embodiments, media cartridge 1000 may share some or all characteristics in common with media cartridge 108 discussed above with respect to FIG. 1.

As shown in FIGS. 10A & 10B, media cartridge 1000 may comprise enclosure 1002, which may be any body structure such as a rigid outer housing configured to be handled by a user and to be inserted into a docking station or other receiving device.

Media cartridge 1000 may further comprise indicator 1004, which may be an indicator configured to indicate a level of fluid inside the cartridge. In some embodiments, indicator 1004 may be a transparent window configured to provide a view of the level of fluid inside cartridge 1000 for visual inspection by a user.

Media cartridge 1000 may further comprise input syringe rubber diaphragm seal 1006, which may be configured to provide a seal protecting an inlet to cartridge 1000. In some embodiments, seal 1006 may securely close cartridge 1000 from contaminants and environmental effects. Furthermore seal 1006 may allow the user to reuse the cartridge and sterilize/autoclave it. Refilling of the media may be done in sterile, tissue-culture conditions to avoid contamination. Using a syringe, a user may poke through seal 1006 and refill media. In some embodiments, a HEPA filter comprised in cartridge 1000 may allow for pressure equilibration since pulling media from the cartridge may create negative partial pressure and at some point may stop the operation of a micropump or decrease the efficiency of fluid transport.

Media cartridge 1000 may further comprise output connector rubber diaphragm seal 1008, which may be configured to provide a seal protecting an outlet from cartridge 1000. In some embodiments, seal 1008 may function in a same or similar manner as seal 1006. In some embodiments, a needle or similar component of a docking station may poke through seal 1008 to allows fluid to be transported out of cartridge 1000 and into the docking station or another component of the system.

Figure 11:
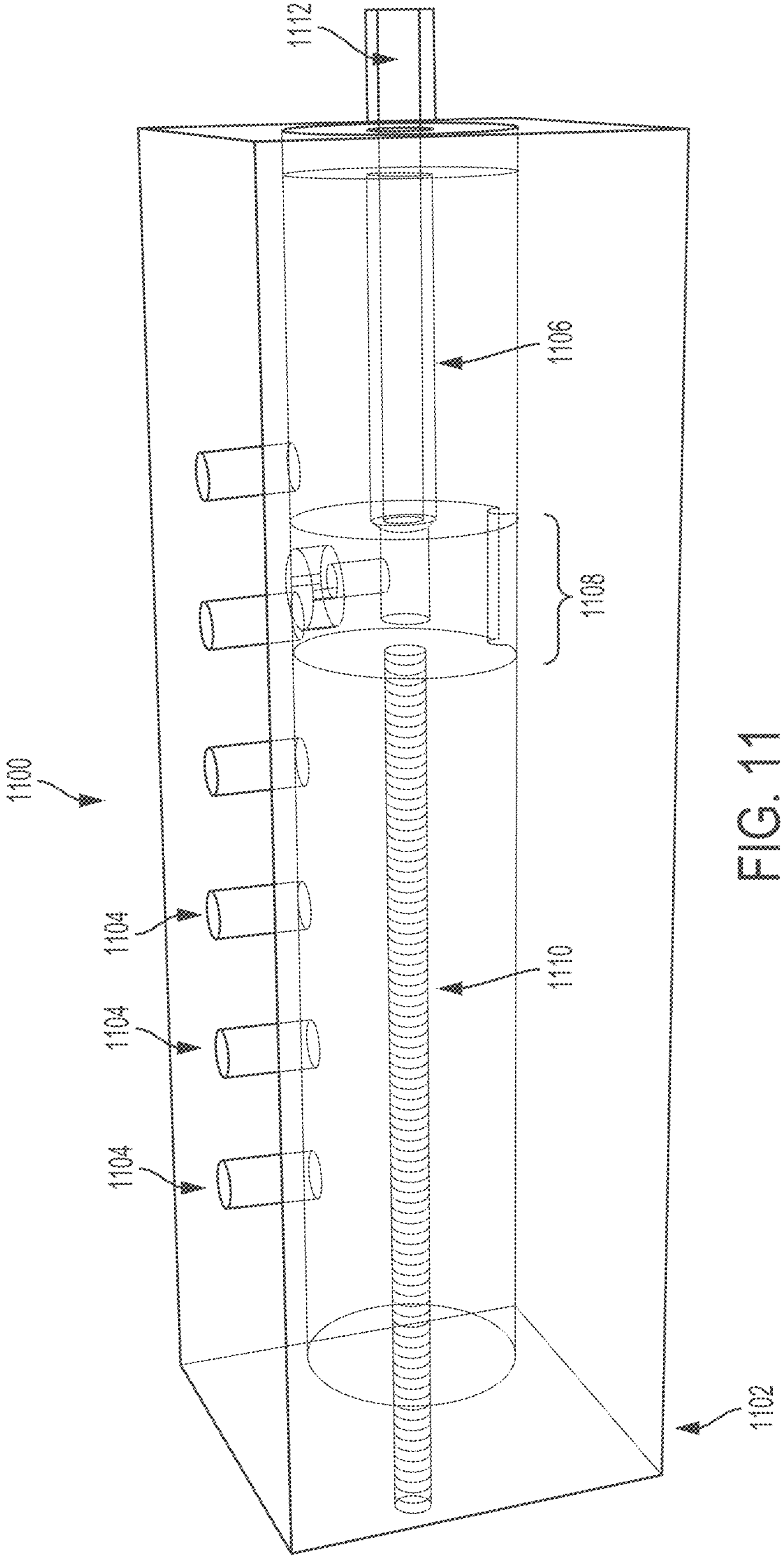
FIG. 11 depicts a pneumatic manifold for use in a cell culture system, in accordance with some embodiments.

FIG. 11 depicts a pneumatic manifold 1100 for use in a cell culture system, in accordance with some embodiments. In some embodiments, pneumatic manifold 1100 may share one or more characteristics in common with the pneumatic manifold discussed above with reference to FIG. 1, including that it may be configured for use with and/or incorporation in a docking station such as docking station 102. As discussed above, a pneumatic manifold may in some embodiments be used to selectively pneumatically couple a single source of vacuum/pressure with one or many pneumatic input lines of a multiwell device, in order to selectively actuate pneumatically-controlled elements of the device such as valves and/or pumps.

In some embodiments, such as those having fewer wells on a single plate (e.g., 6-well plates), one solenoid valve may be used per well. However, in some embodiments, a design with one solenoid valve per plate may not be cost-effective, spatially feasible, or convenient to manufacture for a plate having a higher number of wells (e.g., 96 wells or more). Thus, in some embodiments, the pneumatic layers discussed herein may be used in order to enable each of a large number of wells (e.g., 48 wells, 96 wells, or more) to be individually addressable by allowing for selective connection and disconnection of dozens or scores of pneumatic input lines from a single source of vacuum and/or pressure. In some embodiments, a pneumatic manifold may be driven by a stepper motor. The manifold may reduce the number of solenoid valves for individual well addressing of a 96-well plate from 96 (using a one-solenoid-valve-to-one-well ratio) to just one solenoid valve, thereby greatly reducing cost and manufacturing efficiency.

As shown in FIG. 11, pneumatic manifold 1100 may comprise enclosure 1102, output ports 1104, piston rail 1106, port selector 1108, piston screw 1110, and input port 1112.

As shown, enclosure 1102 may form a housing for one or more of the other components of pneumatic manifold 1100, and enclosure 1102 may comprise a plurality of output ports 1104. In some embodiments, each one of output ports 1104 may be configured to be pneumatically coupled to a pneumatic input port of a multiwell device, such that vacuum and/or pressure may be conveyed from manifold 1100 to a selected one of the input ports of the connected multiwell device.

Inside enclosure 1102, piston rail 1106 and piston screw 1110 may be configured to enable lateral movement of port selector 1108 along the length of manifold 1100. By moving laterally along the length of manifold 1100 via piston rail 1106 and piston screw 1110, port selector 1108 may selectively pneumatically couple and decouple with any one of output ports 1104. In some embodiments, the position of port selector 1108 may be driven by a stepper motor. Thus, by selectively pneumatically coupling with one of output ports 1104, port selector 1108 may couple the selected output port to input port 1112, such that pneumatic force may be conveyed from a pneumatic source connected to input port 1112 through manifold 1100 and to a connected multiwell device.

In some embodiments, operation of pneumatic manifold 1100 may be controlled by a stepper motor, and may be electronically controlled by one or more computerized control systems of an associated device or system, such as a control system of docking station 102 and/or system 100.

Figure 12:
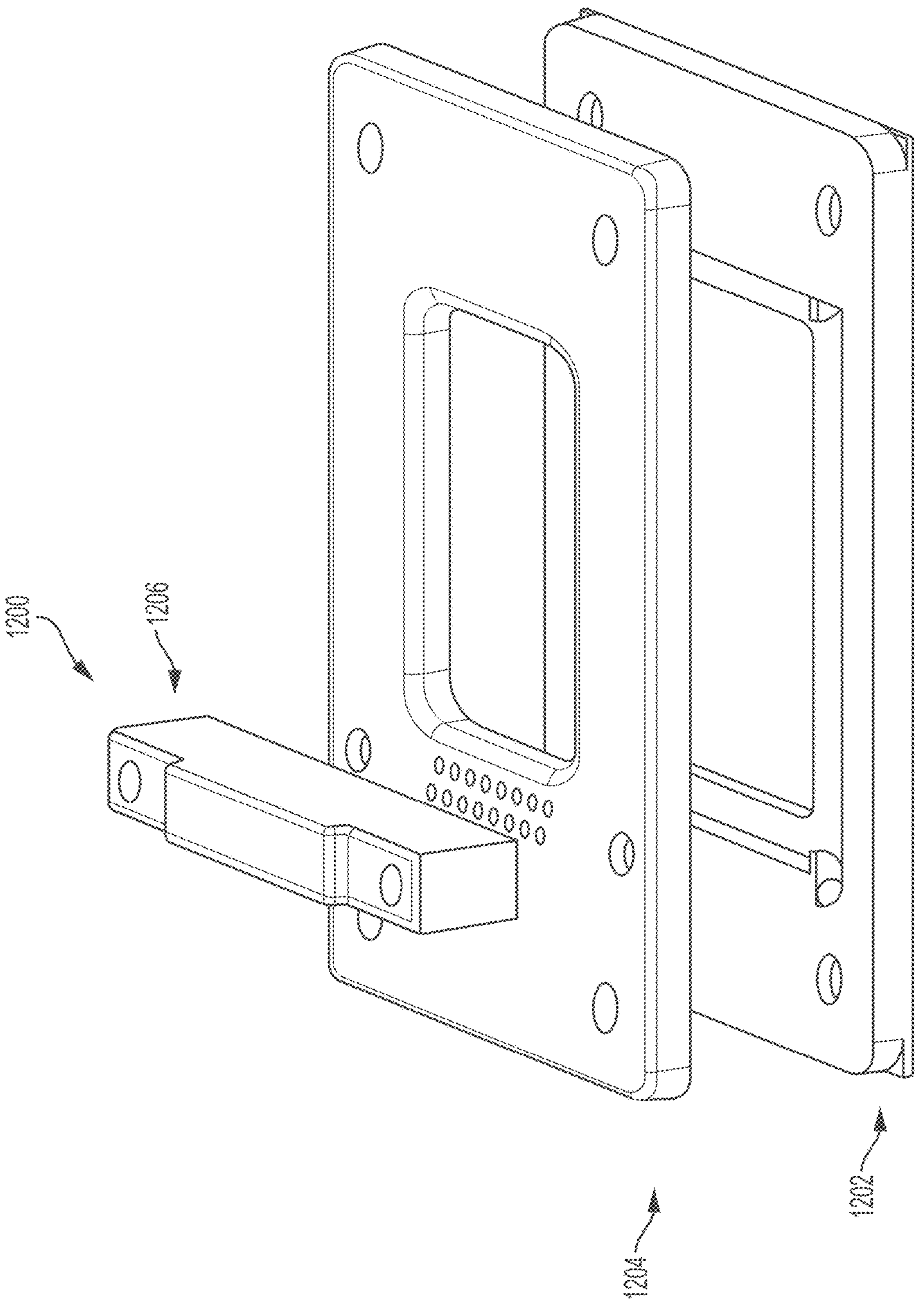
FIG. 12 depicts a manifold adapter for use in a cell culture system, in accordance with some embodiments.

FIG. 12 depicts a manifold adapter 1200 for use in a cell culture system, in accordance with some embodiment. In some embodiments, manifold adapter 1200 may be a portable device, and/or may allow for fast, reliable, and convenient connection of a microfluidic chip without the need for UV/$O_3$ bonding with a glass substrate. In some embodiments, manifold adapter 1200 may allow for pneumatic connection of a multiwell device to a pneumatic source of pressure and/or vacuum, in a similar manner as discussed above with respect to pneumatic manifold 1100. Where pneumatic manifold 1100 may facilitate selective pneumatic connection between input 1112 and one of outputs 1104 (for connection to a multiwell device), manifold adapter 1200 may facilitate pneumatic connection between a plurality of pneumatic inputs and a plurality of pneumatic outputs (for connection to a multiwell device).

As shown in FIG. 12, manifold adapter 1200 may comprise base portion 1202, which may be configured to receive a multiwell device and which may in some embodiments comprise one or more heating elements (e.g., an Indium Tin Oxide (ITO) heating element, or other suitable heating element) configured to regulate a temperature of the multiwell device when the multiwell device is inserted in the base portion.

Base portion 1202 may further comprise one or more electronic connection ports configured to send and/or receive electronic signals regarding monitoring and control of a multiwell device, and its functionalities, connected to adapter 1200. For example, the electronic connection ports of base portion 1202 may be configured to send and receive signals regarding monitoring and/or adjusting one or more characteristics of an environment inside a multiwell device, and/or may be configured to send and receive signals regarding electronic control of one or more valves controlling flow of fluid inside a multiwell device.

Manifold adapter 1200 may further comprise lid portion 1204, which may be configured to hold the multiwell device in place in base portion 1202, such as by fitting over top of the multiwell device and being secured in place by one or more clamps and/or screws.

Manifold adapter 1200 may further comprise pneumatic line connector 1206, which may be configured to pneumatically connect a source of vacuum and/or pressure to one or more pneumatic lines of a multiwell device. In some embodiments, pneumatic line connector 1206 may be configured such that a user may connect one or more pneumatic source lines to connector 1206 such that each of the lines may be connected to a corresponding pneumatic line of a multiwell device via a respective via-hole formed in the body of connector 1206. In some embodiments, connector 1206 may be secured to lid portion 1204 by one or more screws. In some embodiments, pneumatic line connector 1206 may be configured such that a user may disconnect connector 1206 from lid portion 1204, and the multiwell device inserted in adapter 1200 may then be in a sealed or closed condition and may, for example, be able to be physically moved or otherwise handled without being internally contaminated or otherwise compromised.

In some embodiments, manifold adapter 1200 may share some or all of the characteristics and capabilities of docking station 102 discussed above with reference to FIG. 1, including the capability to electronically, pneumatically, and/or fluidly connect to an inserted multiwell device such that one or more cell cultures, assays, and/or protocols may be carried out in the multiwell device while the multiwell device is connected. In some embodiments, manifold adapter 1200 may have a smaller physical form factor than docking station 102; in some embodiments docking station 102 may be configured for use in a benchtop or laboratory setting, while manifold adapter 1200 may be configured for use for microscopy and/or imaging application. (In some embodiments, one or more assays performed by a system disclosed herein may comprise microscopy measurements, such as live/dead staining of U2Os following a culture (see Example 1 below).)

In some embodiments, manifold adapter 1200 may comprise one or more computing elements configured to electronically communicate with a multiwell device inserted into manifold adapter 1200. In some embodiments, manifold adapter 1200 may connect to a multiwell device via wired electronic connections in a same or similar manner as docking station 102. In some embodiments, manifold adapter 1200 may be configured to communicate with one or more sensors and/or a sensor layer of a multiwell device inserted into manifold adapter 1200

In some embodiments, manifold adapter 1200 may comprise a sensor array configured to be attached to a multiwell device or to otherwise sense one or more characteristics of a microenvironment of a multiwell device and/or of an environment surrounding a multiwell device or surrounding manifold adapter 1200.

Figure 13:
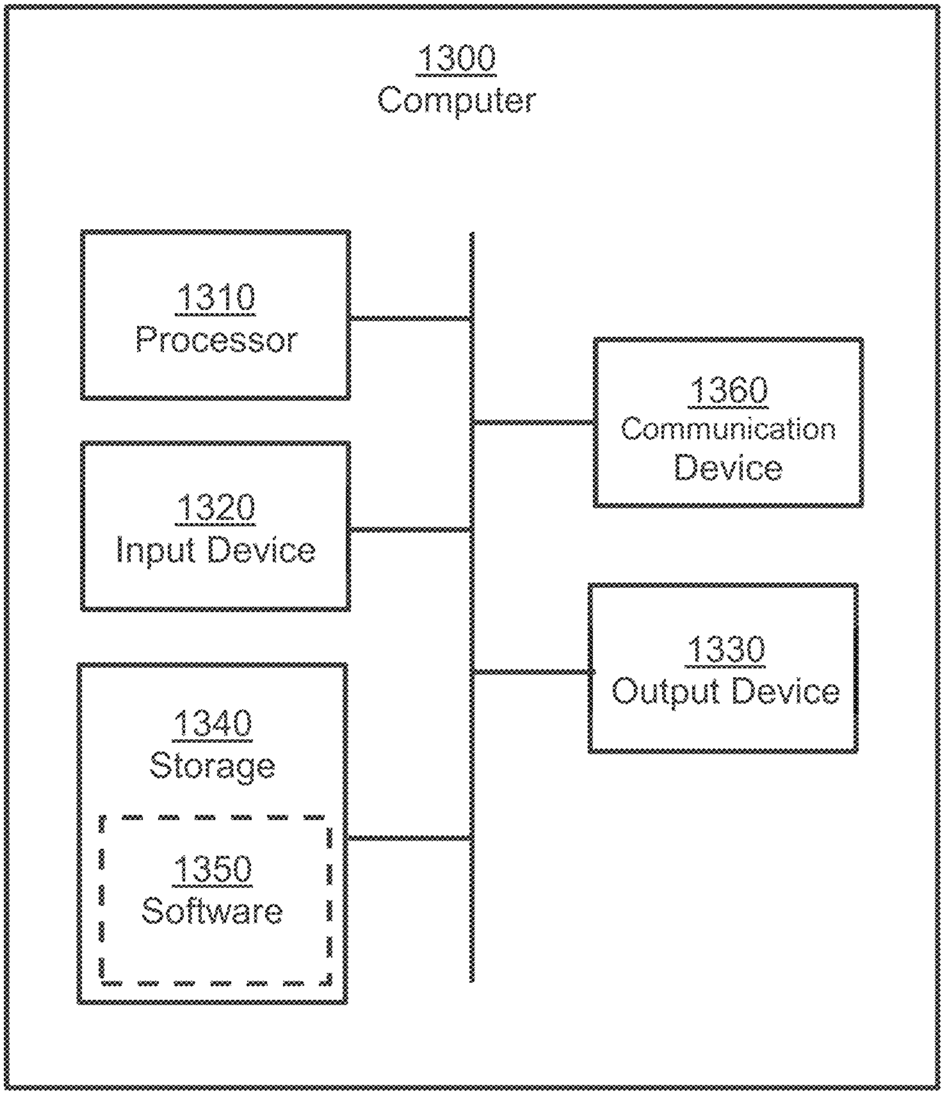
FIG. 13 depicts a computer, in accordance with some embodiments.

FIG. 13 depicts a computer, in accordance with some embodiments. Computer 1300 can be a component of a microfluidics-enabled system for performing live cell cultures, assays, and/or protocols, such as system 100 and/or any of its subcomponents described above with respect to FIG. 1. In some embodiments, computer 1300 is configured to execute a method for performing a live cell culture, assay, and/or protocol, such as any of the methods described herein. In some embodiments, computer 1300 may be configured to control, monitor, or otherwise send and/or receive electronic signals to and/or from any one or more of the microfluidics-enabled and/or multiwell systems and/or devices described herein. In some embodiments, computer 1300 may be a microprocessing device configured to be disposed on a substrate, layer, or chip included in or provided in association with any one or more of the systems, devices, modules, layers, and/or components described herein.

Computer 1300 can be a host computer connected to a network. Computer 1300 can be a client computer or a server. As shown in FIG. 13, computer 1300 can be any suitable type of microprocessor-based device, such as a personal computer; workstation; server; or handheld computing device, such as a phone or tablet. The computer can include, for example, one or more of processor 1310, input device 1320, output device 1330, storage 1340, and communication device 1360.

Input device 1320 can be any suitable device that provides input, such as a touch screen or monitor, keyboard, mouse, or voice-recognition device. Output device 1330 can be any suitable device that provides output, such as a touch screen, monitor, printer, disk drive, or speaker.

Storage 1340 can be any suitable device that provides storage, such as an electrical, magnetic, or optical memory, including a RAM, cache, hard drive, CD-ROM drive, tape drive, or removable storage disk. Communication device 1360 can include any suitable device capable of transmitting and receiving signals over a network, such as a network interface chip or card. The components of the computer can be connected in any suitable manner, such as via a physical bus or wirelessly. Storage 1340 can be a non-transitory computer-readable storage medium comprising one or more programs, which, when executed by one or more processors, such as processor 1310, cause the one or more processors to execute methods and/or techniques described herein, such as, but not limited to, all or part of any methods for controlling systems and/or equipment including multiwell devices for the automated performance of live cell cultures, assays, and other protocols.

Software 1350, which can be stored in storage 1340 and executed by processor 1310, can include, for example, the programming that embodies the functionality of the present disclosure (e.g., as embodied in the systems, computers, servers, and/or devices as described above). In some embodiments, software 1350 can be implemented and executed on a combination of servers such as application servers and database servers.

Software 1350 can also be stored and/or transported within any computer-readable storage medium for use by or in connection with an instruction execution system, apparatus, or device, such as those described above, that can fetch and execute instructions associated with the software from the instruction execution system, apparatus, or device. In the context of this disclosure, a computer-readable storage medium can be any medium, such as storage 1340, that can contain or store programming for use by or in connection with an instruction execution system, apparatus, or device.

Software 1350 can also be propagated within any transport medium for use by or in connection with an instruction execution system, apparatus, or device, such as those described above, that can fetch and execute instructions associated with the software from the instruction execution system, apparatus, or device. In the context of this disclosure, a transport medium can be any medium that can communicate, propagate, or transport programming for use by or in connection with an instruction execution system, apparatus, or device. The transport-readable medium can include, but is not limited to, an electronic, magnetic, optical, electromagnetic, or infrared wired or wireless propagation medium.

Computer 1300 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Computer 1300 can implement any operating system suitable for operating on the network. Software 1350 can be written in any suitable programming language, such as C, C++, Java, or Python. In various embodiments, application software embodying the functionality of the present disclosure can be deployed in different configurations, such as in a client/server arrangement or through a Web browser as a Web-based application or Web service, for example.

Described below are three Examples consistent with the systems, methods, techniques, and devices set out herein.

Example 1—Seeding and Culturing U2OS Cells for at Least 24 Hours

Materials and Reagents:

- Cleaning/sterilization solutions: 70% ethanol (EtOH), 1M sodium-hydroxide (NaOH), 1× phosphate-buffered saline (PBS);
- Cell culture reagents: Media-DMEM/F-12, GlutaMAX™ supplement (Giboco)+20 mM HEPES (4-(2-hydroxyethyl)-1-piperazineethanesulfonic acid)+1×Penicillin Streptomycin (Pen-Strep)+10% fetal bovine serum (FBS), TrypLE™ Express Enzyme (1×), phenol red Cell Preparation:

U2OS TOX$^{ORG}$ (P 40.19) cells were seeded in a standard 6 well (35 mm) multi well plate and cultured for 3-5 days prior transfer into the microfluidic chip. Cells were prepared in standard tissue culture environment and after seeding (2.5E5 cells/mL) in a standard 6 well plate, 2 ml of cell culture media was added into each well containing U2OS cells. The 6 well plate was then transferred into a tissue culture incubator (5% CO2). Media was exchanged every 48 hours to ensure proper cell culture conditions and nutrient supply. Visual inspection was used to determine a cell confluency. U2OS cells were then selected for microfluidic cell culture once confluency of the wells reached approximately 75-80% per well. The 6 well plate was then transferred to a biological safety hood, surface sterilization of the closed well plate and any equipment and components used was ensured by spraying a 70% EtOH solution over the surface for a contact time of at least 1 min before further handling.

In the meantime the media and other used reagents were warmed up to 37 C using a water-bath.

Dissociation of Cultured Cells:

To dissociate the cultured cells in the standard 6 well plate the media from the wells was aspirated using a sterile pipet and a liquid waste trap under the vacuum. After aspiration of the media the cell layer was rinsed with 3 mL of sterile 1×PBS solution, aspirated and 0.5 mL of TrypLE was added to the wells for 2 minutes 30 seconds.

Determination of the exact/best contact time of the dissociation reagent with the cells was determined in several iterations of post seeding and adhesion experiments in the assembled microfluidic chip. The disassociation/contact time has direct effect on the adhesion ability of the cells within the microfluidic chip; the adhesion to the glass substrate layer. Higher disassociation times result in longer adhesion times to the substrate layer of the microfluidic chip, since more surface proteins for adhesion are denatured and need to be rebuild.

After the 2 min 30 sec contact time with TripLE 3 mL of media was added to each well with the disassociation reagent to quench the effect of the reagent. The 6 well plate was manually agitated by vigorously rocking the well plate against the palm of the hand to dissociate the cells within the well.

The disassociated cell-media-reagent suspension was then transferred to a 15 mL falcon tube, transferred to a bench top centrifuge and centrifuged at 1200 rpm for 3 min. The supernatant TripLE/media solution was eluted from the 15 mL falcon tube within the biosafety cabinet, again any transfer in/out was associated with a surface sterilization of the equipment using a 70% EtOH solution.

The cell pellet was then resuspended with 0.5 mL of fresh media by careful agitation of the solution within the tube using a standard pipet. Thereafter the cell suspension is then transferred to a 1.5 mL Eppendorf tube.

The cell suspension is now prepared for seeding to the microfluidic chip. Prior seeding 10 μL of the cell suspension were used for cell counting. Target cell concentration for seeding into the microfluidic chip is about 1.0-4.0E6 cells/mL.

Microfluidic Chip Preparation/Cleaning:

Prior cell loading to the microfluidic chip the assembled chip was cleaned with several solvents to ensure full sterility of the microenvironment. At the same time as the cleaning protocol will rinse and clean the chip, the integrated indium-tin oxide (ITO) heating element will be connected to the systems' heating port connection and the element will heat the microfluidic chip to 37 C throughout the cleaning protocol.

To clean the chip four 15 mL falcon tubes are filled with 1) 70% ethanol, 2) 1M sodium-hydroxide (NaOH), 3) 1×PBS and 4) media for later automated cell culture.

Each falcon tube lid will be punctured with a 1.5 mm biopsy punch to insert the tubing as well as a secondary 1.5 mm hole in which a sterile, HEPA filtered, 200 μL pipet tip will be inserted. This filtered pipet tip will ensure sterility and pressure equilibration due to extracted media through the tubing through the micro pump operation.

To connect the reagents from the falcon tubes to the microfluidic chip a Tygon tubing (0.64 mm I.D./1.59 mm O.D.) was connected to both inlets and to the outlet of the microfluidic chip. The outlet tubing was then connected to a 50 mL empty falcon tube to collect the waste and reagents from the cleaning cycle. Tubing at inlet 1 as well as tubing connected to inlet 2 are connected to the 70% ethanol solution. (Note that the numbering conventions used in this example protocol the same as shown in FIG. 6W.) The individual falcon tubes with the cleaning solutions and the waste tube were placed in close proximity of the microfluidic chip in standard falcon tube holder.

Using the graphical user interface (GUI) the cleaning cycle was initiated using a similar protocol of the automated perfusion program that later will be configured for the automated media exchange during the long term cell culture experiments.

Prior using the automated protocol the connected tubing was filled with the ethanol solution using a direct system control setting by opening main inlet 1, row valve 2 and perfusion valve at 175 ms step-time and 500 pump-strokes. This facilitates that the tubing will be filled with the ethanol solution and the main perfusion channels of the chip are filled as well. After this step the same settings (with the only difference being inlet 2 instead of inlet 1) are used to rinse inlet 2 and corresponding tubing with the ethanol solution. Once this process has finished the tubing from inlet 2 is transferred to the 1M NaOH solution and the process is repeated. Thereafter the tubing from inlet 2 is transferred to the PBS solution and the process is repeated.

The main parameter to be configured in the interface for cleaning the chip with a automated cleaning protocol are 1) step-time of the micro-pump actuation, 2) number of repetitions/pump-strokes per a) rinsing the fluidic perfusion channels and b) perfusing/cleaning the individual addressable wells and 3) system pause between one cycle of operation (rinsing of each perfusion row and each individual well). The parameters used for the microfluidic chip cleaning protocol are 1) 175 ms step-time, 2) a) 15 pump-strokes per perfusion channel and b) 10×8 pump-strokes per individual addressable well and 3) 2 minute pause in-between each cycle of operation.

The system then starts automatically to cycle between the perfusion channels and the individual addressable wells and rinses these chip compartments with the to inlet 1 connected ethanol solution. The rinsed waste is collected in the 50 ml falcon tube connected to the outlet port.

After 15 minutes of cleaning with the ethanol solution the tubing from inlet 1 is then transferred from the ethanol falcon tube to the 1M NaOH solution during a system pause step. Now the system will continue the cleaning protocol but instead of pulling ethanol the 1M NaOH solution will be perfused into the chip and the individual chip compartments. This cleaning cycle will be left to operate for another 60 minutes with the same system configurations for perfusion. After 60 minutes of rinsing the system with 1M NaOH the tubing is then transferred from the 1M NaOH solution to the 1×PBS solution in the same fashion as the first change from 70% ethanol to 1M NaOH during a system pause between cleaning cycles.

After another 60 minutes of perfusion of the microfluidic chip with 1×PBS the inlet is then transferred to the falcon tube containing the media for the later automated cell culture experiment in the same fashion as the prior transfers from one falcon tube to the next.

A final cleaning cycle of 30 minutes using the media from inlet port 1 ensures that the micro-environment in the microfluidic chip is already adjusted to the later cell culture conditions.

At the same time the user can prepare the cell suspension used for the experiment as described above. Once the last cleaning step, rinsing the microfluidic chip with media, is completed the automated cleaning protocol is stopped. The connected media in inlet 1 will be left connected to the chip. Prior detachment of tubing in inlet 2 the tubing from that inlet is as well transferred to the media solution and a final perfusion of media through inlet 2 at 175 ms step-time and a perfusion of 150-250 pump-strokes is performed. Thereafter tubing from inlet 2 is detached and a sterile 200 μL pipet tip with HEPA filter is placed in the inlet port 2 to avoid contamination. The waste tube connected to the outlet will be removed and replaced with a new empty/sterile 50 mL falcon tube.

By now the ITO heating element will also have adjusted the temperature of the chip to 37 C (the temperature for individual cell lines and biological applications might vary and can be adjusted by the user in the system settings).

Cell Loading and Adhesion Time Setting:

While the system performs the microfluidic chip cleaning protocol the user can prepare the cell suspension used for seeding as discussed earlier.

The systems' GUI can now be reprogrammed for the automated cell culture experiment including automated seeding of cells to the individual addressable wells.

Main parameter required (parameters might differ from cell line to cell line and biological application and assay) for this protocol are 1) step-time for the micro-pump actuation, 2) number of repetitions/pump-strokes per a) rinsing the fluidic perfusion channels and b) perfusing the individual addressable wells, 3) number of pump-strokes for seeding cells into the individual addressable wells, 4) adhesion time for the cells in the wells after seeding and 5) system pause in-between perfusion interval of the individual wells determining the perfusion duty cycle. Once these parameters are set the user can proceed to add the cell suspension and start the automated cell culture protocol.

The used settings for culturing U2OS TOX$^{ORG}$ (P 40.19) cells are 1) 175 ms, 2a) 15 pump-strokes per perfusion channel, 2b) 3×8 pump strokes per individual addressable well, 3) 5 pump-strokes for seeding the cell suspension into the individual addressable wells, 4) 60 minutes adhesion time after cells have been loaded into the individual addressable wells and 5) 15 minutes pause in-between the individual perfusion cycles.

The user now uses a standard laboratory pipet and a 200 μL pipet tip with HEPA filter to extract 100 μL of the prepared cell suspension. The pipet tip is then inserted into inlet 2 where it replaces the empty pipet tip placed earlier to avoid contaminations on the microfluidic chip and detached from the pipet. The HEPA filter within the pipet tip ensures that the cell suspension is not exposed to environmental contaminations.

Now the automated cell culture and cell loading profile can be started by the user. A interactive interface checks the inserted parameters with the user and after confirmation the protocol is initiated. A short delay of 60 seconds allows the cell suspension to sediment slightly within the attached pipet tip.

The system now opens inlet valve 2, row valve 1 and the flush valve and pumps 50+15 pump-strokes of the cell suspension into the microfluidic chip to ensure that the cell suspension is inserted into the microfluidic chip. Once the perfusion channel 1 is filled the flush valve closes and well 1 valves open and a total of 5 pump-strokes (earlier defined by the user as described above in point 3) of the protocol settings) are delivered to well 1. Thereafter well 1 valves close and well 2 valves open and 5 pump-strokes are delivered to well 2. After the wells in row 1 are filled the row 1 valve closes and row valve 2 and the flush valve open. The perfusion channel in row 2 is now perfused with 15 pump-strokes after which the flush valve closes and well 3 valves open and 5 pump-strokes are delivered to well 3.

Thereafter well 3 valves close and well 4 valves open and 5 pump-strokes are delivered to well 4. After the wells in row 2 are filled the row 2 valve closes and row valve 3 and the flush valve open. The perfusion channel in row 3 is now perfused with 15 pump-strokes after which the flush valve closes and well 5 valves open and 5 pump-strokes are delivered to well 5.

Thereafter well 5 valves close and well 6 valves open and 5 pump-strokes are delivered to well 6.

Now each well in the chip has been filled with 5 pump-strokes of the cell suspension from inlet 2. Immediately after inlet 2 is closed.

The system now opens inlet valve 1, row valve 1 and the flush valve and pumps 75 pump-strokes of the connected media from inlet 1 into the microfluidic chip to rinse any remaining cell suspension still within the perfusion channel in row 1 out of the microfluidic system and into the waste.

After the perfusion channel in row 1 is rinsed the row 1 valve closes and row valve 2 opens (flush valve still open). The perfusion channel in row 2 is now perfused with 75 pump-strokes.

After the perfusion channel in row 2 is rinsed the row 2 valve closes and row valve 3 opens (flush valve still open). The perfusion channel in row 3 is now perfused with 75 pump-strokes.

During the cleaning of the perfusion channels all well valves remain closed. After this cleaning cycle of the perfusion channels in the rows, the system repeats the same perfusion channel cleaning process once more.

Once the cleaning of the second cycle of cleaning the perfusion channels is complete the system is initiating the cell adhesion pause for 60 minutes (specified by the user earlier in point 4) of the protocol settings) and closes inlet valve 1, row valve 3 and flush valve. In this time the cells will start to sediment within the wells and adhere to the substrate and start attaching.

Now the user can replace the remaining cell suspension within the pipet tip in inlet 2 with a sterile pipet tip with HEPA filter and dispose or reseed the remaining cell suspension in a standard well plate in the tissue culture and run it as a control experiment in the standard incubator conditions.

After the predetermined cell adhesion time the system reopens inlet valve 1, row valve 1 and flush valve and will exchange the media in the perfusion channel in row 1. Therefore, the system uses the by the user specified pump-strokes per perfusion channel in 2a) and exchanges the media in the perfusion channel by 15 pump-strokes.

Once the perfusion channel 1 is filled the flush valve closes and well 1 valves open and a total of 3×8 pump-strokes (earlier defined by the user as described above in point 2b) of the protocol settings) are delivered to well 1. Thereafter well 1 valves close and well 2 valves open and 3×8 pump-strokes are delivered to well 2. After the wells in row 1 are filled the row 1 valve closes and row valve 2 and the flush valve open. The perfusion channel in row 2 is now perfused with 15 pump-strokes after which the flush valve closes and well 3 valves open and 3×8 pump-strokes are delivered to well 3.

Thereafter well 3 valves close and well 4 valves open and 3×8 pump-strokes are delivered to well 4. After the wells in row 2 are filled the row 2 valve closes and row valve 3 and the flush valve open. The perfusion channel in row 3 is now perfused with 15 pump-strokes after which the flush valve closes and well 5 valves open and 3×8 pump-strokes are delivered to well 5. Thereafter well 5 valves close and well 6 valves open and 3×8 pump-strokes are delivered to well 6. Once the well 6 has been exchanged with fresh media the next system pause is initiated for 15 minutes (previously defined by the user in point 5). This completes the general operational procedure of media perfusion to the individual wells for an automated cell culture protocol.

Using the portable manifold connector, the user can position the microfluidic chip within and place the assembled setup on either a standard inverted microscope or automated plate reader system. This configuration allows for visual inspection during cell loading and the later automated cell culture of the wells. Furthermore, it allows for time-lapse recording of the microfluidic automated cell culture within the individual addressable wells. Using such a system configuration we were able to record images of cell adhesion and proliferation within the wells over the period of at least 72 hours.

Example 2—Long Term Cell Culture of U2OS in a Multiwell Device

Figure 14:
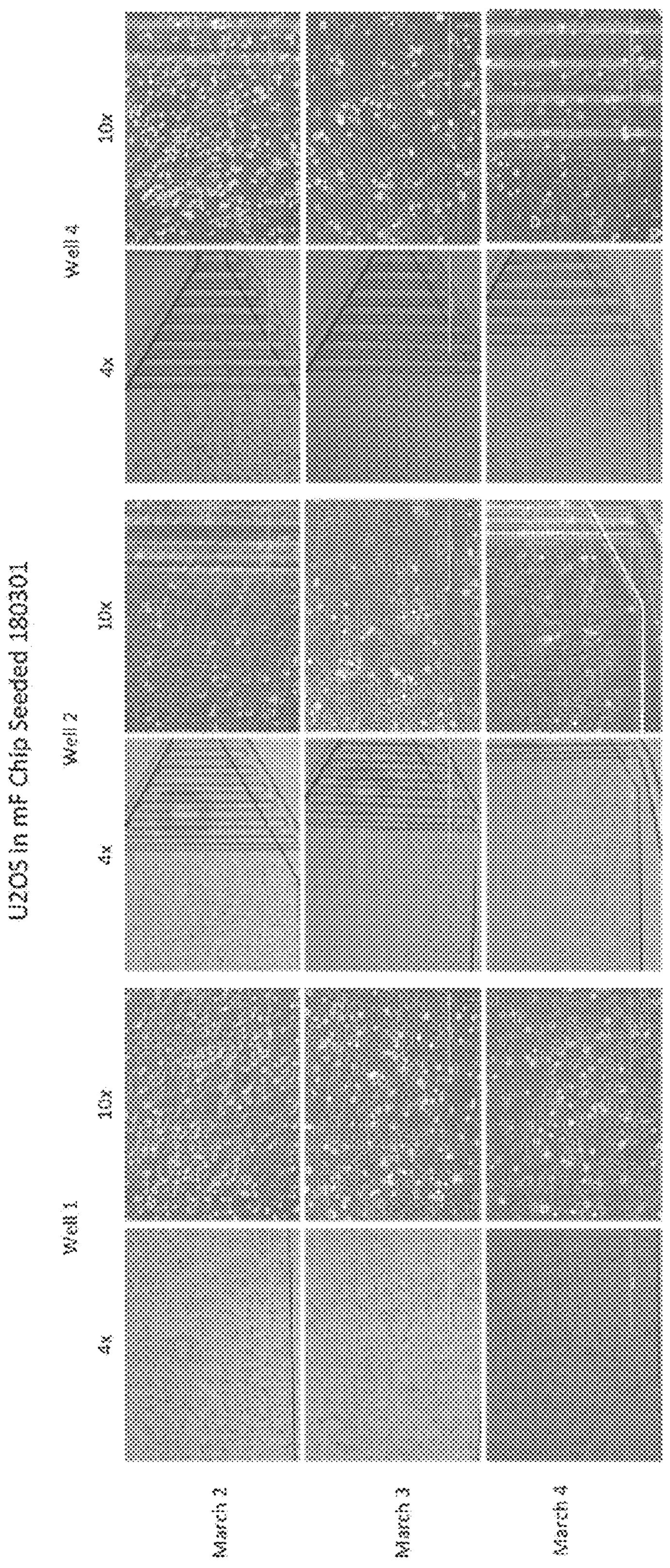
FIG. 14 depicts long term cell culture in a multiwell device, in accordance with some embodiments.

FIG. 14 depicts long term cell culture in a multiwell device, in accordance with some embodiments. Cells were seeded in a microfluidic chip and reached confluency the day after seeding in wells 1 and 2. Wells 1 and 2 were passaged using TrypLE after imaging on the day after seeding. Cultures were maintained with media exchanges every 15 minutes for 3×8 pump-strokes per well.

In some embodiments, the cell culture depicted in FIG. 14 may be consistent with all or part of the protocol set out above in Example 1.

Example 3—Cell Adhesion of U2OS in a Microfluidic Chip

Figure 15:
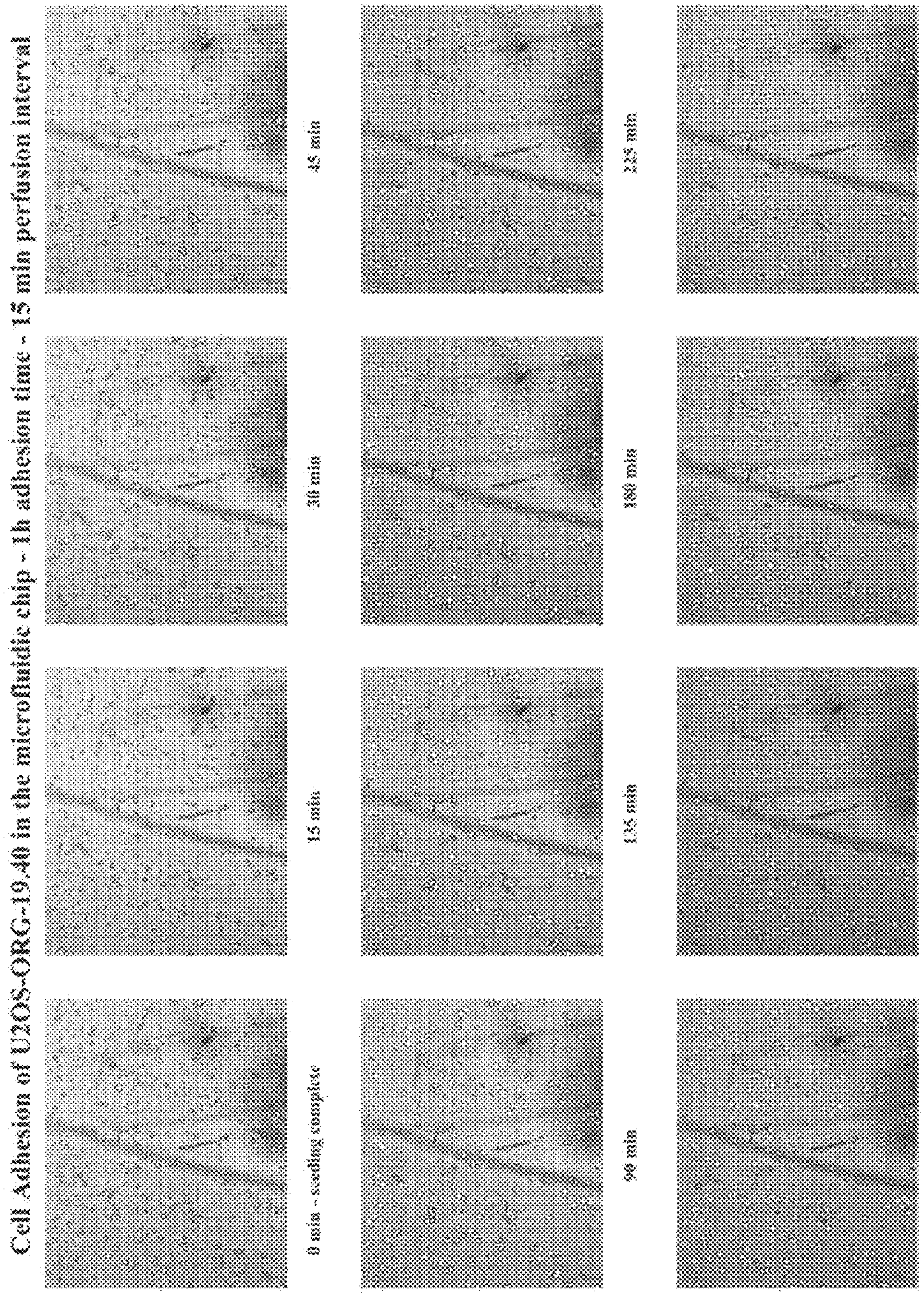
FIG. 15 depicts cell adhesion in a microfluidic chip, in accordance with some embodimets

FIG. 15 depicts cell adhesion in a microfluidic chip, in accordance with some embodiments. FIG. 15 depicts cell adhesion of U2OS TOX$^{ORG}$ (P 40.19) in a microfluidic chip, with one hour adhesion time and 15 minute perfusion interval. The 0-minute image shows the added cells in a well after seeding was completed.

Below, paragraphs [0310]-[0512] contain further discussion of some embodiments relating to the systems, devices, methods and techniques discussed herein.

1 RESULTS OF PHASE I EFFORT

During our successful Phase I effort, we developed a prototype specification for an innovative microfluidic-enabled 'SmartPlate' for precision culture, control and monitoring of living cells in 96-well plate format. Our technical objectives comprised: (1) Development of an initial conceptual design for the multipurpose SmartPlate; (2) Identification of a suitable material for SmartPlate manufacture; (3) Assembly, test and optimization of a sensor module; (4) Assembly, test and optimization of a polydimethlysiloxane (PDMS) 2×3 (6-well) prototype microfluidic array module; (5) Test of microfluidic module under automated control; (6) Demonstration of automated timed compound additions and washouts using the 2×3 prototype microfluidic array; (7) Finalization of a 96-well prototype specification and manufacturing criterion. The research activities and results of our Phase I project are summarized below and presented in detail in our Phase I final report.

The initial conceptual design for the SmartPlate comprised a microfluidic cell culture layer positioned beneath a sensor and electronics module with a footprint and well positioning that conforms to ANSI/SLAS standard 96-well plate specifications. We reviewed our initial conceptual design in the context of its suitability for use with a variety of high-throughput screening and research instrumentation including plate-readers, microscopes, robotic handling equipment and plate hotels. This exercise enabled us to identify ANSI/SLAS plate footprint and well positioning standards to be the most critical parameters for our plate geometry to conform to in order to ensure compatibility with the widest range of equipment possible. We evaluated a panel of microfluidic-compatible materials for inclusion in our prototype manufacturing specification and prioritized cyclo-olefin copolymer (COC) for this purpose since it is biologically inert, optically transparent and suitable for use in a wide-range of biological applications and assay formats such as typical plate-reader luminescence and fluorescence-based readouts, including high-resolution, high-throughput live cell microscopy assays such as those under development at Cairn Biosciences.

We developed the specification for the microfluidic module layer by iterating and testing several 2×3 (6-well) polydimethylsiloxane (PDMS) microfluidic array designs, initially using rapid prototyping and subsequently using arrays manufactured by soft lithography with detailed well geometry that was further optimized using fluid dynamic modeling. Collectively, experimental chip testing and fluid dynamic simulations enabled us to optimize features required for precision live cell assays and culture, including homogeneous well perfusion; precision control of pump volume and fluid flow; and independent well addressing without reagent crosstalk.

Our proof-of-concept sensor module controls and monitors the microfluidic layer and includes 4 operational sensors (temperature, humidity, % $CO_2$ and flow rate). We demonstrated the ability to power and run these sensors using an on-board battery and to broadcast data from these sensors using an on-board WiFi module, thus enabling full functionality of the sensor module while in-use in a plate-reader or other instrument. We tested the individual sensor performance in breadboard configuration and then designed, manufactured, populated and tested a PCB that integrated the subassemblies onto a board with dimensions within the footprint of a standard multiwell plate.

We confirmed the suitability of our 6-well SmartPlate for automated multi-day sterile cell culture with closed-loop temperature monitoring and control and media exchange controlled by our device. We cultured U2OS cells for 3 days in the device on the bench (i.e. outside an incubator) and monitored cell health periodically by microscopy. The permeability of PDMS ultimately limited the maximum duration of culture due to media evaporation issues.

The aggregate results from development and testing of the microfluidic and sensor modules and associated control electronics were used to to develop an updated, detailed specification for a 96-well prototype SmartPlate that will serve as the foundation for development, testing and manufacture of this device in our Phase 2 effort.

Our project establishes compelling proof-of-concept for the feasibility of developing an integrated SmartPlate device for automated cell culture in 96-well format that is compatible with use in a variety of high-throughput plate-reader and robotic instrumentation. The tiered design of our device permits reuse of the sensor module by coupling it to a semi-reusable microfluidic module that is compatible with autoclaving and a disposable cell substrate layer which may be configured using a variety of different materials and geometries according to application need. Furthermore, the work carried out and the bottlenecks and challenges identified in the course of our Phase 1 project, have allowed us to identify opportunities to streamline the development and testing of 96-well device and develop innovative new SmartPlate capabilities that we will implement in Phase 2, e.g. confluency monitoring by impedance measurements in a 96-well array and well-by-well pH sensing. Our successful Phase 1 project has thus strongly positioned us to fully establish and optimize a robust, innovative microfluidic-enabled SmartPlate for precision culture, control and monitoring of living cells in 96-well format. We are confident that our resulting device will enable important next-generation capabilities for the culture and assaying of living cells.

2 DETAILED APPROACH AND METHODOLOGY

2.1 Overview of Technical Objectives

The Technical Objectives described herein may be structured around the overarching project of delivering an innovative 96-well SmartPlate prototype, associated assay application protocols and a robust product manufacturing technique for our device. The SmartPlate is designed to enable plate-based sensing of microenvironment parameters and automated microfluidic-enabled media exchange and perfusion capabilities in an integrated device with a footprint and well positioning that conforms to the ANSI/SLAS microplate standard.

Our project builds on our successful Phase I effort, in which we developed and tested a proof of concept 2×3 (6-well) microfluidic array and associated sensor module and control electronics. The resulting 96-well prototype specification and market research we carried out in parallel may inform the assembly of comprehensive system requirements and conceptual design documentation that will form the initial foundation of our project. Execution of this Phase II project may, in some embodiment, enable these 5 major product development benchmarks:

(1) Production and comprehensive testing of a 96-well prototype SmartPlate
(2) Development of device-specific application protocols
(3) Completion of a pilot product manufacturing run
(4) Field testing of our prototype device and application protocols
(5) Delivery of a robust technique for product manufacture The solutions described herein may, in some embodiments result in a device that can immediately progress to product manufacture and commercialization. A catalog of additional SmartPlate products may be rapidly developed and commercialized for a broad range of cell-based model development and cell-based assay applications and execution of this project will lay an exceptionally strong foundation for us to do so successfully.

The Technical Objectives (TOs) described below may be carried out as a method and/or technique as part of the solutions described herein:

Technical Objective 1: Develop Initial 96-Well SmartPlate Prototype Concept & Requirements TO1 is delivery of a detailed system requirements and prototype concept document. We will carry out additional live cell assay testing of our proof-of-concept 2×3 array to supplement the data acquired in Phase 1, and use the results to inform the content of our requirements and concept documentation. Additionally, we will review OEM sensors and other off-the-shelf components to ensure that we take into account any recently released or updated components that may be useful for addressing the requirements we identify. We will also review market research and gather additional detailed user input from Cairn's cell biologists to inform the preparation of the our documentation.

Technical Objective 2: Identification, Test and Validation of SmartPlate Applications The main focus of this technical objective will be on the identification of application specific system requirements and evaluation of key plate capabilities needed to implement a range of cell based assay applications. We will identify potential sensor and microfluidic technology challenges and implement methods to overcome them. Initial SmartPlate applications that we will consider include high-throughput transfections, high-content screening assays, induced pluripotent stem cell (iPSC) differentiation protocols and automated cell splitting for long term cell culture experiments and we aim to prioritize up to 3 applications for development in the course of this Technical Objective.

Technical Objective 3: Specify, Build and Test all SmartPlate Prototype Subsystems During the execution of this Technical Objective we will build and test the prototype SmartPlate subsystems (primarily microfluidic and sensor modules and microcontroller, in addition to peripheral accessories such as manifolds and reservoirs) needed to meet system requirements and user feedback collected in Phase 1 and TO1. We will characterize and qualify components and subsystems to ensure they enable our system to comply with the system requirements and concept developed in TO1. Additionally, we will design, manufacture and test custom components needed for our prototype development. Rigorous testing of all subsystems and components will enable us to confirm that they meet performance requirements and to identify and mitigate any subsystem risks. Resulting data will be used to inform the design of our final 96-well SmartPlate prototype Technical Objective 4: SmartPlate Prototype System Integration In Technical Objective 4 we will build up to 4 variants of a each subsystem using different methods and/or technologies that have unique risk/benefit profiles. We will integrate the various subsystems and rigorously test them to expose the strengths and weaknesses of the respective overall system architectures and subsystem characteristics, providing further data to inform and derisk our final 96-well SmartPlate prototype design.

Technical Objective 5: SmartPlate Prototype Manufacture and Test

To carry this technical objective we will downselect the subsystem variants tested in TO4 to build two fully integrated prototypes that we will test with protocols established in TO4. The outcomes of these tests and our collective experience with the constituent subsystems, will enable us to establish an optimum single final prototype design that we will produce and test. Finally, this design will undergo a Design for Manufacturability (DFM) phase, wherein a design package will be completed in preparation for a pilot manufacturing run.

Technical Objective 6: SmartPlate Product Manufacturing Pilot

In this Technical Objective we will work with a contract manufacturer to execute a manufacturing pilot run to produce at least 25 prototype 96-well SmartPlates. The design package produced in TO5 will be used as an input for this process and the pilot will be executed in partnership with the contract manufacturer. Product will be shipped from the manufacturer to field-test sites in preparation for Technical Objective 7.

Technical Objective 7: Field Test SmartPlate Product

While the pilot production units are being manufactured in TO6, we will develop SOP's and a standard field test protocol in order to test the full functionality of the SmartPlate system in a regular laboratory environment and in the hands of prospective customers. We will identify up to 10 individual field test sites. Data gathered from these field tests will be analysed and the overall performance of the system and its sub-components will be evaluated. This will allow us to further refine and optimize the device based on the feedback to ensure we have a stable and reliable cell culture analysis system design that meets customer requirements.

Technical Objective 8: Delivery of Detailed Manufacturing Specifications

We will incorporate lessons learned in the course of the manufacturing pilot and addressing issues identified in the course of field testing to produce our finalized prototype design, application specific protocols and manufacturing specification/technique. Concurrently, we will write the Phase 2 final report.

2.2 Detailed Work Plan

The detailed rationale and methodology for each Technical Objective is presented below with associated tasks.

Technical Objective 1: Develop Initial 96-Well SmartPlate Prototype Concept & Requirements In the course of our Phase 1 effort we developed the 96-well SmartPlate prototype concept and delivered associated detailed design documents and a preliminary manufacturing estimate (See Phase I Technical report,). Our design was based on intensive iteration, testing and characterization of a 2×3 well prototype and its sub-components and an associated PCB-based sensor module. This Technical Objective is to further develop these designs and concepts into detailed requirements and concept documentation that will inform downstream Technical Objectives. We will carry out additional testing and development of live cell assay protocols in our 2×3 proof-of-concept microfluidic device to inform the development of the device requirements and concept. Additionally, we will review the suitability of newly released miniaturized sensors and components for incorporation into our device.

We will also refine the design of particular features and components for to mitigate risks identified in Phase I based on testing of our 2×3 proof-of-concept array. For example, we (1) test the performance of an off-chip degasser (2) ensure that any vibration caused by microfluidic pump operation does not negatively impact device performance in the context of high-resolution imaging or other sensitive applications; (3) refine and test our manifold design to ensure its full compatibility with use in a plate-reader or microscope chamber; (4) further develop the concept for modular ink-jet style media reservoirs (3) further develop the concept of our docking station to ensure it meets anticipated user requirements.

The prototype concepts developed in Phase I will enable rapid initiation and progress of Technical Objective 1 and provide a strong foundation to develop a full 96-well prototype specification within the first 12 months of the project.

Tasks

Task 1.1 Cell Experiments in Proof-of-Concept 2×3 Array

We completed a detailed characterization of the microfluidic module including pumping rates and volumes, cross contamination, timed media addition and wash-out in the course of our Phase I project as detailed herein and initiated experiments to characterize these same parameters in the context of live cell culture experiments. Since time did not permit us to complete these experiments, we will complete a more in depth cell culture experiment analysis at the start of our Phase 2 project to provide additional practical insights regarding fluid handling and degasser positioning, well optimization and well perfusion as well as cell loading and system sealing. We aim to establish a reliable protocol for successful sterile cell culture of at least 2 weeks duration using at least 3 cell lines with different characteristics. We test two human immortalized cell lines with different adherence characteristics and doubling times and one iPSC line as follows:

Subtask 1.1.1 Test Delivery of Dilution Series of Doxycycline to Living Reporter Cells in 2×3 Array.

Monitor scaling of fluorescent response to dilution series. Compare with experiment performed manually on cells plated in 6 wells of standard 96 well-plate.

Subtask 1.1.2 Test Timed Delivery of Single Doxycycline Concentration to Individual Wells Containing Live Reporter Cells in 2×3 Array Monitor timing of induction of fluorescent signal relative to timing of compound delivery. Compare with experiment performed manually on cells plated in 6 wells of standard 96 well-plate.

Subtask 1.1.3 Test Timed Wash-Out of Single Doxycycline Concentration to Individual Wells Containing Live Reporter Cells in 2×3 Array Monitor timing of decrease of fluorescent signal relative to timing of compound washout. Compare with experiment performed manually on cells plated in 6 wells of standard 96 well-plate.

Task 1.2 Initial Product System Requirements

We will refine intended use cases and associated requirements for our 96-well prototype SmartPlate system. We will evaluate our Phase I data, live cell data from Task 1.1 and our market research data to specify the equipment and instrumentation requirements for our SmartPlate, associated peripherals and control system. We will prioritize requirements that address stakeholder needs and pain points; i.e. what does our end product need to do for the user. The gathered requirements will determine the following:

- Sensor module measurement and control requirements: E.g. What are the top priority parameters to be monitored and controlled and to what degree of accuracy?
- Fluid transport requirements: E.g. what frequency and volume of fluid transfer is required in/out of wells
- Cell substrate requirements: Materials, surface finishes, coatings and other pertinent characteristics
- Fluid reservoir requirements: How many reservoirs, reusable vs. disposable, etc., volumes
- Base/docking station requirements: Desired characteristics of the overall system enclosure, user interfaces and environment in which it operates (a key parameter to decide here is whether the system should reside inside or outside a tissue culture incubator).
- Controller requirements: Data handling/storage/transmission and system control
- Software/GUI requirements: Data presentation and user interface At the conclusion of this task, we will conduct a design review in which we will review the validity and attainability of all requirements agree upon a final requirements list to use in execution of downstream Technical Objectives.

Task 1.3 Initial Product Conceptual Design

In Task 1.3 we will evaluate and iterate the preliminary prototype system proposed in Phase I and develop into more detailed concept design(s) that will meet updated requirements list from Task 1.2. In the concept design of the system's components and subsystems we will also integrate the solicited user feedback gathered in market research and preliminary experience gathered from the 2×3 system handling. This task also includes investigation of all available technologies that can be used to meet product requirements defined in Task 1.2, and evaluation of how best to integrate these technologies into the subsystems. We will then define detailed system architectures and block diagrams for viable concepts including, but not limited to:

- PCB/sensor concepts
- microfluidics concepts
- Cell substrate concepts
- manifold/connectors concepts
- reservoir concepts
- base/docking station concepts
- controller concepts
- software/GUI concepts Finally, a design review will be held, in which all concepts will be evaluated for compliance with both top-level and derived requirements.

At the conclusion of this task, we will conduct a design review in which we will review all concepts developed to ensure their compliance with the requirements defined in the course of Task 1.2 and agree upon a finalized concept document to be used in the execution of downstream Technical Objectives.

Task 1.4 Specify OEM Components and Identify Custom Component Needs

We will assemble a list of OEM components and identify custom components required to build prototype(s) of the product concept(s) defined in Task 1.3 that fulfil product requirements defined in Task 1.2 and fully document specifications for these components. To arrive at these specifications, extensive engineering models will be employed as needed (thermal and mechanical stress FEA, CFD, etc.). We will conclude this task by reviewing these component specifications against the requirements to ensure compliance.

Alternative Approaches

We consider that a risk associated with TO1 is the possibility of either cell culture data collection or concept and requirements definition taking longer than anticipated. We have resourced cell culture activities generously by assigning both an Associate Engineer and an Application Scientist to their execution. These tasks could be further expedited by involvement of additional Cairn Biosciences cell biology experts if needed. We appreciate that concept and requirements definition could become a very open-ended task.

Technical Objective 2: Identification, Test and Validation of SmartPlate Applications This Technical Objective is the identification of up to 3 SmartPlate applications for further development and evaluation in the course of later field tests. Initial SmartPlate applications that we will consider include high-throughput transfections, high-content screening assays, induced pluripotent stem cell (iPSC) differentiation protocols and automated cell splitting for long term cell culture experiments. After prioritizing up to 3 applications, we will identify application specific system requirements and evaluate key plate capabilities needed to implement a range of cell-based assay applications. We will identify potential sensor microfluidic technology challenges and test methods to overcome them and develop preliminary application protocols using our 2×3 6-well proof-of-concept device.

Task 2.1 Identification and Prioritization of SmartPlate Applications

We will define and identify potential applications for the SmartPlate prototype that are compatible with our anticipated design (based on concepts and requirements developed in TO1). The market research that we conducted indicate a high demand for the SmartPlate in applications including (1) iPSc differentiation, (2) high-content/microscopy-based assays (3) large scale optimization of cell transfection and (4) automated cell culture maintenance for long-term cultures and assays. We will evaluate these applications closely and review more recent market literature to identify any additional priority areas not previously identified. After establishing a short-list of up to 3 potential applications we will evaluate the instrument, sensors, electronics and microfluidic requirements necessary to execute them and prioritize applications that strike a balance of feasibility of implementation using our device and high market need.

Task 2.2 Application Testing on the SmartPlate Prototype

To validate feasibility and experimental procedure we will test the selected applications from Task 2.1 in our 2×3 proof-of-concept array and implement necessary proof-of-concept subsystems to execute these tests. We will write initial application standard operating procedures (SOPs) which will then be further refined in the course of developing field-test protocols in TO7.

Alternative Approaches:

We consider that the main potential pitfall associated with this TO is the possibility that cell culture testing takes longer than anticipated. We will therefore ensure that we prioritize at least one application involving a highly proliferative cell line to ensure that we can test and iterate our protocols rapidly. A second way to mitigate this risk will be to deprioritize applications involving cells such as iPSCs that are either highly sensitive and/or slow to proliferate, which will make applications more time-consuming and challenging to establish. However, given the significant commercial potential of a robust iPSC-culture related application, we will only deprioritize these applications as a last resort.

Technical Objective 3: Specify, Build and Test all SmartPlate Prototype Subsystems This technical objective will be conducted in parallel to the conceptual and planning phase started in TO1.2-1.4 and will allow us to test preliminary components while iterating the final specification. Based on the developed preliminary design specification from Phase 1 we can already produce the first 96 well microfluidic sub-component and evaluate it with existing instrumentation and equipment built previously. Further the sensor-board can be manufactured as well and tested individually. The main-objective in this part is to characterize and qualify components and subsystems to be compliant with the main system requirements. Rigorous testing of all subsystems and components will enable us to confirm that they meet performance requirements and to identify and mitigate any subsystem risks. Resulting data will be used to inform the design of our final 96-well SmartPlate prototype Task 3.1 Design Custom Components As most of the system's components are based on OEM and off-the-shelf components, the majority of these can be bought easily, however a few parts will require custom manufacture. The microfluidics and sensor modules will be manufactured by suppliers used for these purposes in our Phase I effort. Custom components, such as the pneumatic manifold to address the wells individually will require custom manufacture. Only components for which we have developed clearly defined requirements and concepts will be designed in this early phase.

Task 3.2 Write Initial Specification to Meet System Requirements & Solicit User Feedback Based on the custom designed sub-components for the system developed in Task 3.1, we will deliver detailed specification data-sheets for each of the sub-components with its performance estimations and limitations. The specifications will be included for all custom sub-components of the system:

- PCB/sensor specification
- microfluidics specification
- Cell substrate specification
- manifold/connectors specification
- reservoir specification
- base/docking station specification
- controller specification
- software/GUI specification Task 3.3 Test OEM Components; Build and Test Custom Components Once specifications and design have been optimized and meet the required standards, the OEM and off-the-shelf parts for the individual systems sub-components will be ordered, assembled and tested. Subsystems and components will be prototyped and iteratively optimized until performance and specification criteria developed in Tasks 3.1. and 3.2 are met. This development work will likely include multiple candidate variants of a given system component or subsystem, for parallel development and later down-selection.

Task 3.4 Subsystem Build and Test

In order to deliver a reliable 96 well smart-plate prototype and to test its whole functionality and capabilities we will prioritize the manufacturing of the most crucial components in the following order:

- Microfluidic 96 well module
- Sensor-board including temperature control and environmental sensors
- Pneumatic manifold controller
- Docking station and preliminary media and compound reservoir Prioritizing the system's sub-components in this way will allow us to demonstrate functionality, conceptual working protocols and meet the requirements specified in TO1. We will integrate subsystems together, test their performance and gather user-feedback from Cairn's cell biologists. We will iterate the design of our GUI and controller to improve ease of user interaction with the system. We will prioritize our build and test of subsystem components as listed below (highest priority items first):

1. Build, characterize and test individual sub-components of PCB, microfluidics, cell substrate and manifold with basic controller Allows Demonstration of SmartPlate Functionality, Concept, Requirements 2. Add reservoirs, upgraded controller and basic GUI Allows Use in Instruments, Use by Non-Expert User Via Basic Interface 3. Add basic dock station and upgraded GUI Allows Recharging, Longer-Term Culture in Between Use in Common Instruments 4. Add upgraded dock station Full Integrated System Functionality Alternative Approaches Time constraints represent the most significant pitfall associated with this Technical Objective. We will therefore prioritize aggressively to ensure that we deliver a collection of subsystems that enable us to demonstrate and validate the widest possible range of SmartPlate functions and capabilities in the time available.

Technical Objective 4: SmartPlate Prototype System Integration

The results of TO1 and TO3 will yield a variety of different designs and sub-components options. In Technical Objective 4, we will down-select to prioritize 2 system designs that strike the best balance of function, commercial potential and manufacturability. Developing and rigorously testing/characterizing these systems in parallel will expose the strengths and weaknesses of the respective overall system architectures and subsystem characteristics, providing inputs for a robust final system design.

Task 4.1 Prototype System Design x2

Use concepts, requirements and subsystem test data generated in preceding TOs, we will develop at least two prototype system designs for prototype manufacture. This task will conclude with a design review.

Task 4.2 Mechanical Layout x2

We will complete a mechanical layout for each prototype system design developed in Task 4.1. The layout will define the physical relationships of the subsystems and their interfaces. Incorporate design for human factors (ergonomics, safety, durability) at this stage. This task will conclude with a design review.

Task 4.3 Detailed Mechanical Design

Using the mechanical layouts completed in Task 4.2, we complete detailed mechanical design and electromechanical integration design sufficient to build a prototype. This task will conclude with a design review.

Task 4.4 Electrical Design x2

Using the system designs generate in Task 4.1, we will complete schematic-level electrical design and breadboard testing, followed by fully-integrated PCB and cable assembly designs. This task will conclude with a design review.

Alternative Approaches

Component and subsystem risks have been fully addressed in TO3, so risk at this point is low. Potential risk is primarily related to supplier lead times for specialized components, in the event that required components differ from test articles already on hand. We will prioritize early purchase and identify alternative suppliers for any components that appear likely to have a long lead-time to mitigate this risk.

Technical Objective 5: SmartPlate Prototype Manufacture and Test

This technical objective starts with the two prototype designs delivered at the end of TO4 and results in a single, tested, manufacturable design. The two prototype designs will be built, then tested with protocols established in TO4. The systems will then be subjected to alpha testing with a small number of external users to identify issues and solicit user feedback. We intend to invite a prospective NCATS user of the device to participate in this test. Armed with the outcomes of these tests and our collective experience with the systems, we will then down-select to a single prototype design. Finally, this design will undergo a Design for Manufacturability (DFM) phase, wherein a design package will be completed in preparation for a pilot manufacturing run.

Task 5.1 Manufacture Top 2 Prototype Designs

Using the design packages produced in TO4, a small quantity (up to 10 each) of at least two prototype design variants will be manufactured.

Task 5.2 Repeat Test Protocols on Prototype Systems

Using test protocols developed early in the project, perform verification testing on the prototypes in order to confirm compliance with requirements and discover strengths and weaknesses.

Task 5.3 Alpha Test (User)

In a highly-controlled manner, submit a very small quantity of all prototype variants to selected users for evaluation under pre-defined protocols in order to solicit feedback and validate the designs.

Task 5.4 Down-Selection

After analyzing the results of the Alpha test and other concurrent internal testing, select a final system design (or define a final system based on a combination of subsystems within the candidate systems).

Task 5.5 Final Product Design for Manufacture

Adapt system design to accommodate chosen component production manufacturing methods and integrate chosen subsystems into a final, manufacturable design.

Alternative Approaches

Certain aspects of the system design, while working well as components or subsystems, may not integrate well with the rest of the system from the standpoint of size, cost vs. performance, ease of manufacturing, etc. This multi-pronged approach to prototype development, wherein we build multiple variants, mitigates this risk by funneling multiple complementary ideas further down the development path, preserving our ability to substitute an alternative component to address problems of this nature that are identified in the course of prototype build and test.

Technical Objective 6: SmartPlate Product Manufacturing Pilot

This technical objective entails working with a contract manufacturer to produce the final design package from TO5 in as close a manner to final production as possible. Using the final design package as an input, a corresponding manufacturing method/technique/specification may be produced. This may then be executed by the contract manufacturer, and the product may be warehoused and shipped to test sites.

Tasks

Task 6.1 Develop SmartPlate Product Manufacturing Technique

Define complete technique for manufacturing the SmartPlate system including facilities, supply chain management, contract manufacturers, product warehousing, order fulfillment, etc.

Task 6.2 Execute SmartPlate Manufacturing Pilot

Using only final-intent production methods wherever possible, produce up to 100 SmartPlate systems.

Task 6.3 Drop-Ship Product to Field-Test Sites

Using warehousing and order fulfillment methods, deliver production-intent units to test sites for evaluation.

Alternative Approaches

At the point of the manufacturing pilot, designs have already been prototyped with high degree of emphasis manufacturability having been considered throughout the process. The risk of taking a design from prototype processes to full-rate manufacturing processes will therefore be minimized. If there is significant apparent risk at the time these tasks are taking place, multiple approaches can be taken simultaneously to manufacture usable parts. The primary risk in device assembly is associated with bonding of of the SmartPlate microfluidic and associated components. Manufacturing cost is an additional risk, since we have based our estimated cost for the pilot manufacturing run based on requirements and scope that we anticipate at this time. Significant deviations from this may result in increased manufacturing cost, in which case we will manufacture fewer units to compensate. Equally, our deviations may result in reduced manufacturing cost if we are able to identify opportunities to streamline the design and manufacturing process of our design.

Technical Objective 7: Field Test SmartPlate Product

While the pilot production units are being manufactured in TO6, we will develop SOP's and a standard field test protocol in order to test the full functionality of the SmartPlate system in a regular laboratory environment and in the hands of prospective customers. We will identify up to 10 individual field test sites, to include user laboratories at NCATS, if desired. Data gathered from these field tests will be analysed and the overall performance of the system and its sub-components will be evaluated. This will allow us to further refine and optimize the device based on the feedback to ensure we have a stable and reliable cell culture analysis system design that meets customer requirements. In this way we converge the device prototype with the application protocols developed in TO2 for testing in the hands of users so that we may deliver a SmartPlate product that has validated utility for important use cases and demonstrated usability in the hands of typical users of the device.

Task 7.1 Define Field Test Protocol

During the manufacturing process we will establish a main SOP protocol and a user manual for general system handling based on the Application SOPs developed in TO2 and the test protocols established earlier in the project.

Task 7.2 Conduct Field Test

Selected users will work with the system and test various assays and protocols. Further the functionality and the handling of the device will be tested by a variety of different skilled users. Also the use of the SmartPlate in commercially available laboratory instruments and routine laboratory environment can be tested. Cairn technical staff will closely monitor the field tests and be available to address user questions and concerns.

Task 7.3 Field Test Data Analysis

The gathered data and experiences from the field test will be analysed and the overall system performance investigated.

Alternative Approaches

A potential pitfall of this task is that the systems will be sent to sympathetic, ‘friendly’ sites that will not provide honest and direct feedback about the experience of using them. Candid, objective feedback is extremely valuable, as this test is a final step before refining the device in light of user comments and then releasing it to a market that will likely be extremely discerning users of the device. In order to avoid this situation, honest and complete feedback should be specifically requested, and we may consider having the process of field testing managed by a third party in order to ensure that feedback received is objective.

A second potential pitfall is that users receive devices and do not perform the requested testing and/or provide their feedback on the desired timeline. We will endeavor to monitor the field tests closely to mitigate the likelihood of this issue.

3 APPENDICES 3.1 Phase I Technical Report

Summary of Salient Results

In this project, we developed a prototype specification for an innovative microfluidic-enabled ‘SmartPlate’ for live cell assays. Our plate configuration comprises a microfluidic cell culture layer beneath a sensor module with a footprint and well layout that conforms to standard 96-well plate specifications. We developed the microfluidic layer specification by iterating and testing 2×3-well polydimethylsiloxane (PDMS) microfluidic array designs to optimize features including homogenous well perfusion; reproducible, precision pumping; and independent well addressing without reagent crosstalk. We prioritized the biologically inert, optically transparent material cycloolefin copolymer (COC) for 96-well device manufacture. The sensor module controls and monitors the microfluidic layer. We delivered a prototype sensor module by characterizing candidate sensors and associated electrical components (battery, WiFi module) and then integrating individual subassemblies onto a single printed circuit board (PCB). We confirmed the suitability of our 6-well SmartPlate for automated multi-day sterile cell culture with temperature monitoring and control and media exchange controlled by our device.

Our project establishes compelling proof-of-concept for the feasibility of developing an integrated SmartPlate device for automated cell culture in 96-well format. In Phase 2, we will use this foundation to deliver and fully test an innovative device that enables next-generation capabilities for long-term precision culture and assaying of living cells.

Project Results & Discussion

1. Technical Objective 1: Complete Initial Conceptual Design of Multipurpose Smart-Plate For this Technical Objective we proposed to use graphical visualization and design tools to complete an initial conceptual design of our multipurpose Smart-Plate to guide our subsequent prototyping activities (Technical Objectives 2-5). As detailed below, we developed initial conceptual designs for our microcontroller and sensor electronics module and their connection as a basis for subsequent testing and iteration in later milestones. We incorporated 6 priority features into our initial sensor module conceptual design and 4 priority features into our initial microfluidic module conceptual design, thus exceeding the corresponding milestone requirements. We confirmed the compatibility of our preliminary device specification with a variety of high-throughput robotic and plate-reader instrumentation.

1.1 Results and Discussion

Task 1.1: Establish Conceptual Design of the Microcontroller and Sensor Electronics Module We anticipated that compatibility with instrumentation would require our plate to conform to the standard footprint of a 96-well assay plate. Given the ability of several pieces of robotic and high-throughput instrumentation to work with thicker objects (e.g. tip boxes), we assessed that plate height would be the most flexible dimension for our device. We therefore proposed an initial tiered design concept with a 96-well plate footprint because it would allow us to maximize the space available for microcontroller and sensor electronics on the PCB and leave a full 96-well sized footprint for microfluidics in the lower layer. We envisioned that subsequent optimization and prototyping activities would allow us to reduce the plate height of this tiered configuration. We also emphasized a simplified design to minimize manufacturing technical risk and cost.

Additional details on the conceptual design of each sensor module tier follow:

Tier 1 (bottom): Includes all direct sensors (e.g. pH and microfluidic flow rates), environmental controls (such as a heater element), and control over fluid valves.

Tier 2 (middle): Microcontroller/power/amplification: This tier is used for most of the computing and sensor input/output (I/O) needed for the project. Integrated circuits (ICs) on this layer include wireless communications interface, an ATMega2560, microcontroller, op amps, multiplexer/demultiplexer (mux/demux), level shifters and other components typically associated with signal processing and I/O work.

Tier 3 (top): Battery: This layer includes 2 batteries, a power connection for the docking station, a battery charge controller IC, and battery mounts.

Task 1.2: Establish Conceptual Design of the Microfluidic Module

A 6-well 2×3 array is shown for illustrative purposes; our 8×12 96-well array will be configured according to ANSI/SBS well-position standards with volume reduced to the extent necessary to accommodate sensor and actuation components. The microfluidic module is positioned underneath the tiered electromechanical module described in Task 1.1. The footprint of the microfluidic module will conform to ANSI/SBS 96-well plate standards, while sensor and actuation components will be designed to occupy minimum possible volume within a standard multiwell format. Valves and pneumatic control are configured to allow individual well addressing for rapid and automated addition and exchange of assay reagents according to the needs of typical drug discovery assays (e.g., dilution series, timed compound additions). Further detailed discussion of the chip module design is included herein.

Task 1.3: Establish Conceptual Design of the Manifold Connector Module

Since we anticipated that the geometry of sensor and microfluidic module designs would evolve considerably in the course of the project, we limited the conceptual design of our connector module to the following list of features to be incorporated into the finalized prototype design:

- Spring-loads for fast attachment/detachment of the microfluidic system
- Connection ports for the pneumatic actuation of the micropumps and microvalves.
- Electrical connection pins for sensors/controllers integrated in microfluidic layer.
- Fluid connection ports for reagent and media reservoirs.

Task 1.4: Confirm Compatibility of SmartPlate Conceptual Design with a Range of Relevant Instrumentation.

We evaluated microscopes, plate-readers, and high-throughput and robotic instrumentation at core facilities, such as the University of California San Francisco (UCSF) Small Molecule Discovery Center and UCSF's Nikon Imaging Center, to identify aspects of instrumentation that would place a constraint on the dimensions of our proposed SmartPlate. We evaluated plate dimensions that would be compatible with handling by the following classes of instrumentation (actual instrument evaluated noted in parentheses): Plate handling robots (Thermo F5 6-axis plate handling robot); plate hotels (Liconic incubated plate hotel); plate readers (GE InCell Analyzer 2000 high-content reader); research-grade automated microscopes (Nikon TiE microscope with multiwell plate scanning module). This evaluation confirmed that ensuring our plate design conforms to SBS guidelines for plate footprint (width and length) is of prime importance since there is generally very little tolerance to accommodate plates of dimensions that are any wider or longer. While some plate-readers have some flexibility regarding their ability to read plates with different well configurations, automated (and manual multichannel) dispensers are generally not able to accommodate plates with non-standard well spacing, we therefore prioritized standard well spacing for our upscaled 96-well design. The biggest constraint we identified for plate height is the size of the opening through which plates are loaded. For example, the GE InCell Analyzer 2000 limits plate height to ~2 cm. Since different plate readers have different plate loading mechanism designs, we will evaluate the mechanical specifications of additional instruments to identify whether any of them impose tighter constraints on plate height during in Phase 2.

2. Technical Objective 2: Test and Characterize Reusable Materials

For this Technical Objective we proposed to evaluate and characterize the suitability of a panel of materials to identify those best suited for our Smart-Plate application. Our review and testing of relevant materials led us to prioritize cycloolefin copolymer (COC) as a biocompatible, optically transparent material compatible with microfluidic manufacture processes and suitable for typical plate-reader luminescence and fluorescence-based readouts including high-resolution, high-throughput live cell microscopy assays.

2.1 Results and Discussion

Task 2.1: Research a Shortlist of Candidate Microfluidic-Compatible Materials

We evaluated 12 materials and material categories (Appendix A) as candidate materials for manufacturing our reusable Smart-Plate. Our findings led us to prioritize the thermoplastic COC for our initial testing because it is routinely used as a cell culture substrate, has demonstrated suitability for high-resolution fluorescence microscopy, and is reusable. It is also compatible with cost-effective manufacture of complex multilayer microfluidic components with 3D channel profiles using hot embossing[1].

Task 2.2: Empirically Test Up to 5 Materials for their Compatibility with Routine Cell Culture and high-resolution fluorescence microscopy Several manufacturers offer COC plates for cell-based assays. We tested the performance of a commercially available COC plate (Corning 96-well COC plate #4680) by culturing A549 cells over a period of 3 days and comparing with results of cells cultured in glass (Corning 96-well glass plate #353072) and polystyrene (Corning 96-well polystyrene plate #4580) plates. Cells remained healthy throughout the course of incubation in all 3 plates and with comparable proliferation rates. In light of our measurements and the extensive literature and commercial precedent for the use of COC in cell culture applications and reports of its suitability for microfluidic device manufacture, we prioritized this material for inclusion in our detailed prototype specification.

3. Technical Objective 3: Configure and Test Microcontroller and Sensors

For this Technical Objective, we proposed to prioritize a panel of sensors for use in our SmartPlate. We evaluated and tested a panel of commercially available sensors and identified alternatives to sensors with prohibitive cost or lead time. Our final prototype includes 4 operational sensors (temperature, humidity, CO2, flow rate) exceeding the milestone requirement for inclusion of 3 sensors. We demonstrated the ability to power and run these sensors using the on-board battery and to broadcast data from these sensors by the on-board WiFi module, enabling full functionality of the sensor module while in-use in a plate-reader or other instrument. Our PCB design also includes components to enable later addition of pH measurement and impedance measurements for cell confluency. We tested the individual sensor performance in breadboard configuration and then designed, manufactured, populated and tested a PCB that integrated the various sub-assemblies onto a board with dimensions within the footprint of a standard multiwell plate.

3.1 Results and Discussion

Task 3.1: Evaluate Commercially Available Sensors for Integration into SmartPlate The sensors and associated components proposed for the SmartPlate sensor module prototype are summarized in Table 1 and discussed in more detail below and in Task 3.2 purposes[2], which is reporting with full range scale via the 16-bit ADC. Representative status reporting from all integrated sensors is shown below:

/////Report String Example/////

Thrm A,13478,Thrm B,13524,Flow,1.0034,pH,210,Humidity (% RH),41.85,Temperature (C),26.90,Co2 (ppm),620

Thrm A,13487,Thrm B, 13527, Flow,1.0030,pH,210,Humidity (% RH),41.72,Temperature (C),26.90,Co2 (ppm),630

Thrm A, 13509, Thrm B,13545, Flow, 1.0027, pH,210, Humidity (% RH),41.68, Temperature (C),26.90,Co2 (ppm),630

Thrm A, 13522, Thrm B,13559, Flow, 1.0027,pH,210, Humidity (% RH),41.65,Temperature (C),26.90,Co2 (ppm),630

Thrm A,13504, Thrm B,13559, Flow, 1.0041, pH,210, Humidity (% RH),41.68, Temperature (C),26.90,Co2 (ppm),640

Thrm A, 13494, Thrm B,13561, Flow, 1.0050,pH,210, Humidity (% RH),41.72, Temperature (C),26.72,Co2 (ppm),640

Thrm A,13524, Thrm B, 13591, Flow, 1.0050,pH,210, Humidity (% RH),41.65,Temperature (C),26.90,Co2 (ppm),640

Thrm A, 13521, Thrm B,13604, Flow, 1.0061,pH,210, Humidity (% RH),41.68,Temperature (C),26.90,Co2 (ppm),650

////End Example/////

Sensor Module Test Data

WiFi Module

We modified the code of the WiFi component of our assembly to work with our system and provide wireless

TABLE 1

Prioritized sensors and associated components integrated onto sensor module prototype PCB. For self-developed sensors, we note a contingency commercially available sensor.

| Measurement | Device | Manufacturer | Range | Precision | Notes |
|---|---|---|---|---|---|
| Temperature | SHT25 | Sensirion | −40-125° C. | 0.01° C. | |
| Humidity | SHT25 | Sensirion | 0-100% | 0.04% RH | |
| pH[2] | | Self | pH 4-10 | TBD | INA116 impedance amplifier integrated on PCB |
| pH (contingency) | OII1 | Optol | pH 2-12 | 55 mV/pH | Long lead time therefore prioritizing self-developed component |
| $CO_2$ | K-30-10000 | CO2meter.com | 0-10% | 3% of reading | |
| Flow | Thermistor NTC 100 kΩ 1% bead | Murata | 0-100 kΩ | TBD | |
| Flow (contingency) | LPG10 | Sensirion | <1000 μL/min | 5% scale | High cost $150-300/unit therefore prioritizing self-developed component |
| Confluency (impedance) | | Self | | TBD | INA116 impedance amplifier and ADS115 analog-to-digital converter integrated on PCB |
| Battery | Powerboost 1000 | Adafruit | 3.7-5 V | NA | |
| WiFi module | CC3000 | Sparkfun | NA | NA | |

Task 3.2: Assemble 3 Top Priority Sensors with Microcontroller, Test and Demonstrate Device Communication and Control We acquired the CO2, temperature and humidity sensors noted in Table 1 and implemented a prototype thermistor-based flow sensor. We routed the Murata thermistor readings via a 16-bit AGC Analog to Digital Converter (ADC) with integral gain control to ensure adequate precision for ratiometric measurements of fluid temperatures and hence fluid flow. We integrated all sensors and tested their outputs using serial interface to the microcontroller. Readings also include the impedance amplifier, integrated for pH measurement status updates. We demonstrated the ability to upload sensor output data to a live web readout at thingspeak.com.

Battery

We tested the power budget for a full sensor run using only the battery system. The sensor system was polled continually, with all sensors and the wireless module powered on throughout the test. Reports were issued to the online sensor channel once every 15 minutes. The test resulted in a 9-hour power-on duration at full draw. Using sleep state modes in the WiFi module, $CO_2$ sensor, and microcontroller in between web updates should dramatically extend the useful reporting time of the system to an estimated uptime estimate of 7 days if using all sleep state modes for the various subsystems and starting with a fully charged battery.

$CO_2$

Although there are a number of sensors available to integrate $CO_2$ measurement into air quality systems, environmental systems, and HVAC assemblies, the sensor used in our module had to meet 3 unusual requirements: (1) smallest possible form factor; (2) no gas input port/chamber and (3) 0-10% concentration range. Of the available sensors, only the $CO_2$Meter K30-10000 module provided these features. This sensor uses a non-dispersive infrared radiation measurement to report $CO_2$ in decimal parts per million reported over a serial UART at 9600 baud. The non-dispersive IR measurement method can be affected by background variation (heat). The module provides an automatic background compensation method, to produce a claimed sensitivity of 1%, with 3% accuracy. The sensor reads at a maximum interval of 2 seconds. Our controller polls the system more frequently than this; when polling is performed at a faster rate than measurement, the last measured value is returned. The $CO_2$ sensor therefore has a slower response time than other sensors used. A typical fresh air measurement should reflect a value of 400-450 ppm.

In order to first verify the $CO_2$ sensor response to at least 10% range (per the sensor specification and data sheet), we configured it for battery powered operation with WiFi reporting and then sealed it inside a Styrofoam box with a 30 mm deep layer of dry ice pellets. While we found the sensor to be responsive to $CO_2$, we found its readings to be capped at 4.2%, prompting us to obtain a replacement from the supplier for subsequent testing and use on our final PCB build. We tested the replacement $CO_2$ sensor over a 42 hour period, detecting an average reading of 441 ppm (17.3 ppm standard deviation; 3.9% relative standard deviation)

Humidity

We selected the Sensirion SHT21 sensor for % humidity monitoring, which enables sensing from a low-power, small form factor (3 mm×3 mm), pre-calibrated device that also senses temperature. Accuracy of relative humidity sensing for this device is stated by the manufacturer as +/−2.0%. Device communication is via the common i2c protocol. A single microcontroller call results in the device returning a full set of data (humidity and temperature measurement). Accurate measurements require 8 seconds for the sensor to respond, but the sensor may be queried at a maximum rate of 11.75 Hz at an output resolution of 14 bits. We measured change in humidity upon transfer of sensor from indoors to cold. We tested the sensor over a 42-hour period and measured an average relative humidity of 23.68% (0.31% standard deviation; 1.3% relative standard deviation). The increase in humidity measured when the sensor was placed in a sealed box of dry ice.

Temperature

As noted above the Sensirion SHT21 sensor also measures temperature. Accuracy of temperature sensing is stated by the manufacturer as +/−0.3° C. Measured change in temperature upon transfer of sensor from indoors to cold. We tested the sensor over a 42-hour period and measured an average temperature of 46.1° C. (2.93° C. standard deviation; 6.4% relative standard deviation).

Of note, the oscillations measured indicate that the sensor appears to have relatively low temperature performance relative to its datasheet specification. We identified 3 likely causes for this that we did not have time to explore further. First, this sensor did not include the manufacturer-recommended thermal transfers and clearance routes recommended for best performance. It is possible this causes a bootstrapping function on the COB. A second possibility is that the oscillation as measured is accurate, and that either thermal transients on the PCB or in the room were to blame (e.g. temp drops, HVAC turns on, temp rises, and this occurs multiple times in a few days). A third possibility is that the bin selection of this sensor happens to be lower than the stated performance. We will evaluate this further as this sensor is tested in our proposed Phase 2 project.

Flow

Due to the high cost of suitable commercially available flow sensors, e.g. the Sensirion LPG10, we elected to construct our own flow measurement using a ratiometric thermistor bias measurement system based on 2 Murata NTC 100 kΩ 1% bead thermistors. The system was assembled and tested using the flow chamber and flow rates calculated by the thermistor measurements were compared to the input syringe pump-driven flow rate. During this testing, we noted that the system responded to flow changes, unless the input temperature of the flowing fluid was the same as the temperature at the location of the thermistors. Since we need to maintain our SmartPlate and input media at 37° C. for cell culture, i.e. input temperature and thermistor temperature will be equal, we need to reconfigure our flow measurement system to account for this.

This can be addressed by placing a small heating element, e.g. a resistor, in series with the 2 thermistors. Approaching the heater, the fluid temperature increases in the flow direction and the heating effect is more pronounced upstream of the heater. The related downstream/upstream temperature difference can be used to measure flow, which, in this configuration uses the known temperature injected by the heater, rather than the input temperature of the upstream fluid. Although we did not have time to configure our flow sensor accordingly, we tested thermistor performance over 42 hours in ambient conditions. We performed these measurements using channels 2 and 3 of the same ADS1115 ADC used for impedance measurements. These data confirm the stability of the thermistor measurements. Over the 42-hour period, thermistor 1 average reading was 15380 with 138 standard deviation and 0.9% relative standard deviation. The thermistor 2 average reading over the same period was 13925 with 146 standard deviation and 1.05% relative standard deviation.

This measurement still produces several important results. First, both thermistors were routed into the same ADC used for impedance, the ADS1115, on channels 2 & 3. In the 42 hour timelapse below, both thermistors were left exposed to ambient conditions. It follows that measurements obtained through the ADS IC may be used to indicate performance under load of the IC, as well as to measure the relative performance of the 2 thermistors against one another. Were the sensors and ADC perfect, all measurements would result in a 0.000 ratio. Any deviation of this result indicates either a bias between the 2 thermistors, or internal error in the ADC. As a result, several plots are presented below, to investigate the performance of these 3 factors against one another.

Impedance

Our configuration for monitoring impedance comprises an INA116 amplifier, the output of which is routed to a 16-bit ADS1115 low power ADC. This package provides quad inputs for single ended measurement, a stable internal reference, scalable gain, low footprint and wide supply range. The sensor data is output via an i2c interface that affords straightforward connection to our microcontroller.

Due to lack of time, we were not able to test this sensor's ability to measure confluency. However, by running the sensor unconnected to a probe for 42 hours, we could evaluate the inherent system noise of the design. Our data indicate that this setup provides a low-noise baseline which can be used as basis for further development in Phase 2. Data reported is 16-bit signed scale, i.e. values of 0-65535 may be obtained from these measurements. Measurement below varies between 202-204.

PCB Production and Testing

After testing sensors in breadboard configuration, we developed the design of our final sensor prototype by laying out a PCB design that integrates all the previously tested subassemblies on a single board. The footprint of our design is 100×80 mm, well within the 128×85 mm dimensions of a standard multiwell plate. We accomplished a significant reduction in size and complexity by stripping away the Arduino microcontroller headers and using only the components required for our needs. The $CO_2$ and WiFi modules remain in daughter-board configuration, due to their complexity and consequently longer lead time to redesign these components; we may review and redesign these components.

Our PCB design includes 2 impedance amplifiers with no front-end multiplexing to enable proof-of-concept measurements of comparative cell confluence in 2 separate wells. In the course of implementing this capability we identified a hurdle that we will need to overcome in order to scale this solution to a 96-well or higher density format. Since multiplexing systems that would enable measurements of each individual well using one single amplifier inject impedance into any measurement obtained, they are not suitable for this specific application. A direct solution would be to assign a single impedance amplifier to each well, but this is not compatible with scaling to a 96-well format due to board space constraints and increased manufacturing cost. We therefore elected to implement a system to obtain proof-of-concept impedance measurements in 2 wells for this project and we develop an innovative solution to scale this capability to 96-well format in Phase 2.

We populated our initial PCB and soldered components using vapor phase flow soldering. While testing the board, we identified several issues that we determined would be more time efficient to redesign rather than try to troubleshoot around them. Key adjustments include: (1) placement adjustment to ensure impedance sensors line up more accurately with impedance electrodes on microfluidic module; (2) switch to enable battery or USB operation; (3) simplified routing and component placement to make troubleshooting easier; (4) improved component labeling to enable faster component population. PCB fabrication and sensor design files are included in Appendix C.

4. Technical Objective 4: Build and Test Proof-of-Concept 2×3 Microfluidic Array For this Technical Objective, we proposed to build and test initial proof-of-concept 2×3 array prototypes using rapid prototyping in PDMS. We repeated several initial iterations of our preliminary conceptual design using rapid prototyping. We tested these chips and used our finding to converge on a viable design to further iterate and optimize using fluid dynamic modeling and high-resolution photolithography manufacture, ultimately resulting in a 2×3 prototype microfluidic design that is used as the basis for our upscaled 96-well prototype design.

4.1 Results and Discussion

Task 4.1: Design Various Preliminary Designs in a 2×3 Array Scale for Rapid Prototyping We developed our first 2 initial design ideas and manufactured them and related variations using the rapid-prototyping techniques established at UC Berkeley. The first proof-of-principle devices were manufactured using CNC-cutters and photo-masks, which allowed us to test multiple designs in a matter of days, without going through the more labor and time intensive process of soft-lithography in the clean-room. These designs were assembled with our first generation microcontroller design.

We iterated our designs to minimize the number of layers in the design and to accommodate new features identified in the course of designing the sensor module. We implemented our version 3 (v3) designs onwards using soft lithography, allowing us to increase the resolution and detail in our designs. We assembled these designs with an improved Gen2 microcontroller unit that enables control of an increased number of ports and a new manifold connector that allows fast and reliable chip connection without the need for UV/$O_3$ bonding with the glass substrate.

The system control unit was designed and built using OEM and of the shelf components and characterized with the developed microfluidics chips. An Arduino Mega (Arduino Mega 2560 Rev3; Adafruit) is used as the main microprocessor to control a set of switch-boards (ULN2803 Switch board; elexol) which then drive a set of solenoid valves (GAV010E1-12DC; Koganei), a simple 2 row LCD display (HD44780; Adafruit) with key-pad allows the control over step-time, the direct control over the flow-speed of fluid transported in the system. Further the use of conventional microprocessors like Arduino allows a universal, computer independent programing of the unit. In future the Arduino will be replaced by a RaspberryPi with touchscreen on a Python based graphical user interface (GUI) for direct feedback control of the system and reliable assay-protocol design and configuration. Preliminary GUI design has commenced and progress to-date is presented in. This will be further refined and developed in Phase 2.

Task 4.2: Manufacture the Designs Using Rapid Prototyping and Replica Molding

Iteration of subsequent device designs was based on empirical test results and fluid dynamic simulation data. In particular, we used simulation data to optimize well geometry to ensure homogeneous well perfusion profiles.

Several subsequent rounds of optimization led to our finalized 2×3 prototype design that we used as the basis for upscaling our prototype design to 96-well format. The two latest designs were manufactured using soft-lithography with two sizes of microfluidic channels widths (150 μm and 500 μm). All soft-lithography manufactured chips have a final channel height of ~95 μm. The finalized 2×3 prototype encompasses independent addressing of each individual well, preventing cross-talk of media flow between wells; improved well geometry to ensure full and homogenous well perfusion; and a flush valve at the end of each row to enable reliable control of and more rapid wash-out and media exchange.

We the suitability of our iterated chip designs for cell culture on an ongoing basis. Testing of the finalized 2×3 prototype indicated that we could culture U2OS cells for at least 3 days in the chip on the bench (outside incubator) with temperature and media exchange driven automatically by the microcontroller. No contamination was observed, indicating that sterile culture is possible inside our prototype device.

5. Technical Objective 5: Combine 2×3 Microfluidic Array with Sensors and Control Electronics and Test For this technical objective we proposed to assemble our microfluidic system with pneumatic controls and sensors followed by initial system calibration and characterization of system performance and stability. We performed testing that indicated excellent reproducibility and reliability of our microfluidic systems, verified the ability of our degasser geometry to remove air bubbles and confirmed the row-column addressing capabilities of our chip design enabled independent well addressing without cross-contamination between wells.

5.1 Results and Discussion

Task 5.1: Assemble the Microfluidic System and Add External Control Elements for Preliminary Characterization and System Evaluation.

The microfluidic system was characterized using a commercial flow-meter (SLG1430-480; CMOSens) and various test protocols to ensure full valve control and thus precise fluid control over the chip. Fluid was routed from the inlet port through the second row valve into the fourth well chamber and expelled from the system through the pumps towards the outlet port. Calibration data was then analyzed and a flow profile determined. Our data indicate that we can displace as little as 10 nL with 75 ms step time and that this is consistent and reproducible.

The microfluidic layer includes a degasser system which removes air-bubbles from the inlets before they reach the well layers.

Preliminary cross-contamination experiments using rhodamine b (Fastman; 14352) and control (water) were delivered to individual wells and then measured with a fluorescent spectrometer (Spectrofluorometer F-750; Jasco). Cross contamination was negligible and the small residual fluorescent signal is attributed to the porosity of the PDMS causing trapping of some dye molecules that could not be fully removed in the wash-out step. When the microfluidic layer is manufactured in all glass, COC or other non-porous material, this trapping of dye molecules should not occur. We had intended to manufacture a glass chip to test this further, but delivery delays and power outages in the final 2 weeks of the project precluded us from doing so. We will characterize this further in non-PDMS chips during Phase 2.

Task 5.2: Cell Culture and Automated Media Exchange Tests of the Microfluidic System After loading the microfluidic system with complete media for cell maintenance and growth without $CO_2$ equilibration (Leibovitz's 15, supplemented with 10% Fetal Bovine Serum and Penicillin/Streptomycin). To control temperature, we integrated a peltier thermo-element heater element to maintain constant cell culture conditions of 37° C. The thermal image shows a slightly higher temperature of 39.2° C., which is required to compensate for heat loss and dissipation to the environment. We seeded U2OS cells (human osteosarcoma cell line) at 106, $10^5$ and $10^4$ cells/ml. Three hours post-seeding we started the automated flow with a rate of 200 nl/stroke (125 ms step-time; exchange of ~2.3 well-volumes) every 30 minutes for 2 days.

To evaluate cell health and growth we acquired images every day for each well.

6. Technical Objective 6: Demonstrate Timed Compound Additions and Washouts in 2×3 Prototype Array In the course of completing Technical Objective 5, we identified several limitations of our device that precluded its routine use in a cell culture setting. We therefore expended significant effort iterating between device optimization and cell-culture tests to ultimately generate a device suitable for cell culture as shown in Task 5.2. A major limitation we identified was the difficulty of seeding cells into the device using only microfluidic delivery; this is too time-consuming for routine use and biologists are unlikely to want to program cell seeding using the microcontroller when they can address quickly and easily using a manual micropipette.

We therefore reconfigured our device to allow direct seeding of wells by manual micropipetting, enabling us to successfully complete Task 5.2 and Technical Objective 5. Unfortunately, several ordered parts and components arrived later than expected due to manufacturing/delivery delays, slowing our progress. The delays we experienced and the extra time spent optimizing these aspects of the chip was at the expense of completing the Tasks and Milestones of Technical Objective 6, however, we believe that the effort spent on reconfiguring the device and testing it thoroughly positions us strongly to continue cell culture testing at the start of our Phase 2 effort. Given the results of device characterizing and testing in Technical Objective 5, where we showed the precision of the system and its capability to manipulate nanoliter volumes in a precise and repetitive way and its suitability for culturing live cells, we are confident that timed dosing of doxycycline to live cells required for the success of Technical Objective 6 should not pose any insurmountable technical challenge. Furthermore, the results of the cross-contamination dye experiment in Task 5.1 confirm the capability of our system to carry out precise and timed wash-in and wash-out assays with the programmable interface.

6.1 Results and Discussion

The system may be optimized to ensure long-term cell culture of up to two weeks as described in TO5.2 above.

Task 6.1: Test Delivery of Dilution Series of Doxycycline to Living Reporter Cells in 2×3 Array.

One may leverage the system's demonstrated ability to deliver precise volumes of fluid to the wells at timed intervals.

Task 6.2: Test Timed Delivery of Single Doxycycline Concentration to Individual Wells Containing Live Reporter Cells in 2×3 Array.

As for Task 6.1 and discussed above, we demonstrated the necessary device capabilities to complete this task.

Task 6.3: Test Timed Wash-Out of Single Doxycycline Concentration to Individual Wells Containing Live Reporter Cells in 2×3 Array.

As for Tasks 6.1 and 6.2, we demonstrated the necessary device capabilities to complete this task.

7. Technical Objective 7: Finalized Detailed Prototype Specification and Cost Estimate for a 96-Well Format SmartPlate For this Technical Objective, we proposed to evaluate aggregate performance data from preceding Technical Objectives to refine our initial conceptual design into a detailed requirements and design document for a 96-well device that includes mechanical, electrical and microfluidic design details, hardware specifications, communications protocols and manufacturing cost estimates.

7.1 Results and Discussion

Task 7.1: Detailed Microplate Design Based on Experimental Data

We used the finalized 2×3 prototype well-design described under Task 4.2 as the basis for an up-scaled 96-well microfluidic module that conforms with ANSI/SLAS footprint standards.

Well Layer

We note that designing the well layer as a separate module gives us ultimate flexibility to vary its configuration to include, for example, additional sensors (e.g. impedance sensing electrodes); alternative well geometries (e.g. micropatterning or specialized well shape for 3D cultures); or alternative materials (e.g. glass, COC, others) and coatings (e.g. firbonectin, polylysine etc.). Additionally this approach mitigates risk in our product design since, if we were to encounter an insurmountable hurdle with the well design, it does not necessitate an overhaul of the entire microfluidic system, merely a redesign of the well layer. In short, this approach minimizes risk and maximizes flexibility for prototyping and manufacture of new products.

Fluidic Layer

Pneumatic Layer

The pneumatic layer comprises 2 sublayers: (1) a pneumatic well-selection layer and (2) a pneumatic control layer.

In designing the pneumatic well-selection layer, we recognized that scaling the 6-well design with 1 solenoid valve per well would not be a sound choice to generate a cost-effective 96-well SmartPlate. We have therefore drafted a preliminary design for a pneumatic manifold that is driven by a stepper motor. This manifold reduces the necessary solenoid valves for individual well addressing of a 96-well SmartPlate from 96 to one solenoid valve, greatly reducing cost. Detailed design, build and test of this manifold will be included in our Phase 2 project.

ment via sensor modules from mains power and exchange/perfuse media or other reagents into the plates. We have conceptualized an ink-jet cartridge like system for media perfusion that will enable straightforward addition of media or other reagents to the plates in the docking station and we have begun to consider how this could be adapted to a plug-and-play reservoir system that could easily be installed into standard plate-reader instrumentation. We will refine these ideas further in our Phase 2 effort and will seek input from prospective customers and other stakeholders during this exercise.

Task 7.2: Detailed Design Documents for Manufacturing with Cost Estimate Included Detailed design documents are presented in Appendix B and C. Our microfluidic manufacturing cost estimate presented in Table 2 is based on the following assumptions:

- Production parts made from COC manufactured using precision injection molding
- Each part requires a machined steel negative mold (fixed cost tooling investment)
- Each mold can be used to manufacture up to 100,000 units
- Additional cost per run for materials and production labor (run cost)
- Well-layer cost of $2 at 100,000 unit manufacturing scale calculated on basis of $6 cost of standard tissue culture treated plastic 96-well plate, assuming 70% margin.
- Barrier-layer cost assumed to be 50% of well-layer cost at high volume manufacturing

TABLE 2

Manufacturing cost estimates for microfluidic modules assuming manufacture of 1,000 and 100,000 units

| Item # | Layer | Material | Mold Cost | Run Cast (@ 1000/run) | Unit Cast (1000 units) | Unit Cost (100,000 units) |
|---|---|---|---|---|---|---|
| CB-101 | Wells | COC | $4,000 | $3,000 | $7.00 | $2 |
| CB-102 | Fluidics | Solvent bonded to COC | $7,500 | $4,000 | $11.50 | $4 |
| Elastic Sheet | Barrier | PTFE/Silicone/PDMS bonded to fluidic layer | $1,000 | $3,000 | $4.00 | $1 |
| CB-103 | Pneumatics | Bonded to elastic sheet | $7,500 | $4,000 | $11.50 | $4 |
| Full System | Combined | | $23,500 | $15,000 | $34 | $11 |

Sensor Module

As noted in Task 3.2 (PCB Production & Testing subsection) we have left the WiFi module and $CO_2$ sensor in daughter board configuration. We are confident that we will be able to address installing them on the main PCB layer in Phase 2 when we have more time to allot to this task. In order to sense $CO_2$, humidity and temperature conditions on the 96-well format SmartPlate, minimal additional components are required since these parameters will be measured as 'global' plate parameters, rather than on a per well-basis. As discussed in more detail in Task 3.2 (PCB Production & Testing subsection), scaling per-well microenvironment measurements to 96-well, e.g. for impedance or pH sensing may be compatible with additional technical development. Such measurements may be compatible with a modification to the well-layer (e.g. incorporation of electrodes for confluency sensing) and implementation of necessary multiplexing/demultiplexing on the sensor module PCB.

Preliminary Concepts for SmartPlate Docking Station and Peripherals.

While not a requirement of the solicitation, we have begun to conceptualize possibilities for a SmartPlate docking station to which SmartPlates can be returned when not in use in a plate-reading instrument or other experimental setting. The docking station would have capabilities to recharge batteries, monitor and report plate microenviron- As shown in Table 2, our manufacturing cost is estimated to be $11-35 depending on the volume manufactured. The economy of scale for 100,000 units is realistically greater than noted for the fluidic and pneumatic layer because these would be manufactured in runs of more than 1,000 units. This economy of scale is factored in for the well-layer and elastic sheet since we have used estimates based on list prices that account for this. Additionally, these estimates are based on typical mold, materials and production costs for U.S. manufacturing; these costs could be further reduced by outsourcing to overseas manufacturing facilities. Combined, these factors give a realistic manufacturing cost estimate of $5-$10/microfluidic unit, assuming high-volume (>$100 k units) manufacturing.

Our sensor module manufacturing cost estimate presented in Table 3 is based on the assumption that below 100 units, US fabrication, test and assembly is the most cost-effective and that there is negligible component discount for volume purchases. Beyond 100 units, cost decreases rapidly due to economies of scale in materials and component purchase and ability to outsource fabrication, assembly and test overseas.

TABLE 3

Manufacturing cost estimates for sensor modules assuming manufacture of 2, 100, 1000 and 10,000 units

| Item # | Unit cost (2 unit build) | Unit cost (100 unit build) | Unit Cost (1000 unit build) | Unit Cost (10,000 unit build) |
|---|---|---|---|---|
| PCB Fabrication | $35 | $14 | $7 | $4 |
| Components | $185 | $92 | $46 | $23 |
| Assembly & Test | $35 | $14 | $7 | $4 |
| Full System | $255 | $120 | $60 | $30 |

As shown in Table 3, our manufacturing cost is expected to be $30-$120, depending on volume manufactured. Realistically, we expect to be able to further reduce these costs by sourcing or building more cost effective temperature, humidity and CO2 sensing units and WiFi modules which are the major contributors to the sensor module cost. Assuming we could reduce component cost by 50% in this way, this reduces our manufacturing cost to $20-$75, depending on volume.

Assuming manufacture at a scale of at least 10,000 units for the sensor modules and at least 100,000 units for the microfluidic modules, estimated cost for the full SmartPlate (sensor+microfluidic module) is ~$25, of which $5-10 is the semi-reusable microfluidic module and $15-$20 is the reusable sensor module.

8 CONCLUDING REMARKS

The results of our project reported above strongly position Cairn Biosciences to deliver an innovative 96-well SmartPlate prototype in our Phase 2 effort. We have validated our team's ability to conceptualize, build, test and iterate the design of our SmartPlate in proof-of-concept 2×3 (6-well) array format and demonstrated the compatibility of our device with the culture of live cells over several days. We have also planned the scaling of our prototype array to a 96-well device, based on the results of our prototype build and test cycle.

Our development and testing of the proof-of-concept device drove the design of our initial 96-well prototype specification. Our 96-well prototype incorporates all the key characteristics necessary to enable scaling to a commercially viable 96-well SmartPlate for cell-based assays that is suitable for use in a variety of instruments and plate-readers, namely: (i) Close adherence to ANSI/SLAS Microplate standards for plate footprint and well-positioning; (ii) well layer compatible with rapid modification to accommodate different well types, shapes, materials and other features (e.g. electrodes for confluency monitoring); (iii) microfluidic design compatible with well-by-well addressing, such that wells can be used for samples or to perform other functions (e.g media storage, sample collection); (iv) compatibility with culture of live cells over several days; (v) automated sensing of environmental parameters (humidity, temperature and $CO_2$) with real-time transmission via WiFi; (vi) highly modular design that enables incorporation of new features into well or microfluidic layers or sensor module and thus rapid generation of new application-specific product lines; (vii) compatibility with established manufacturing procedures (standard PCB fabrication and assembly, and precision injection molding of COC); (viii) commercially viable manufacturing cost of $25 for the entire device.

These accomplishments give us a very strong foundation to successfully address all the Phase 2 solicitation requirements by building and testing our 96-well SmartPlate and developing a robust manufacturing technique for the device. Furthermore, the findings of our Phase 1 project, combined with market-research data have yielded critical insights that have prompted us to: (i) invest additional time to refine the concept and requirements of our 96-well SmartPlate to ensure that it fully addresses the most critical user needs; (ii) prioritize application-specific development of the SmartPlate to ensure that we deliver a device that is well-optimized for specific uses that we test and refine and test/field test involving prospective users of the SmartPlate. We also ensure the robustness of our manufacturing technique by carrying out a pilot manufacturing run to generate at least 25 units of our device that will be used in field tests. Our project also served to help us identify key risks associated with the project and team and address them by adding in-house expertise to the Cairn Biosciences team and supplementing the expertise of our subcontractors and consultants in Phase 2.

In summary, the aggregate data and learnings from this project have positioned us to fully establish and commercialize an innovative, robust and well-validated SmartPlate in Phase 2. The successful development and commercialization of our device will further enhance Cairn Biosciences' ability to realize their corporate mission of developing next-generation cell-based assays and transformative technologies that enable their scalable implementation.

12 APPENDICES

Appendix A—Candidate Microfluidic-Compatible Materials for SmartPlate

APPENDIX A-TABLE 1

Material properties of common microfluidic-compatible polymer substrates

| Property | silicon/glass | elastomer | thermoset | thermoplastics | hydrogel | paper |
|---|---|---|---|---|---|---|
| common technique for microfabrication | photolithography | casting | casting, photopolymerization | thermomolding | casting, photopolymerization | photolithography, printing |
| smallest channel dimension | <100 nm | <1 μm | <100 nm | ~100 nm | ~10 μm | ~200 μm |
| channel profile | limited 3D | 3D | arbitrary 3D | 3D | 3D | 2D |
| multilayer channels | hard | easy | easy | easy | medium | easy |
| thermostability | very high | medium | high | medium to high | low | medium |
| solvent compatibility | very high | low | high | medium to high | low | medium |
| hydrophobicity | hydrophilic | hydrophobic | hydrophobic | hydrophobic | hydrophilic | amphiphilic |
| surface charge | very stable | not stable | stable | stable | N/A | N/A |
| permeability to oxygen (Barrer*) | <0.01 | ~500 | 0.03-1 | 0.05-5 | >1 | >1 |
| optical transparency | no/high | high | high | medium to high | low to medium | low |

APPENDIX A-TABLE 1-continued

Material properties of common microfluidic-compatible polymer substrates

| Property | silicon/glass | elastomer | thermoset | thermoplastics | hydrogel | paper |
|---|---|---|---|---|---|---|
| Application | | | | | | |
| electrochemical detection | good | limited | moderate | moderate | N/A | N/A |
| droplet formation | excellent | moderate | good | good | N/A | N/A |
| PCR | excellent | good | good | good | N/A | N/A |
| bioculture | moderate | good | moderate | moderate | excellent, 3D | good, 3D |
| cost of production | high | medium | high | low | medium to high | low |
| reusability | yes | no | yes | yes | no | no |
| disposable device use | expensive | good | expensive | good | hard to store | good |

APPENDIX A-TABLE 2

Summary of material categories suitable for microfluidic device fabrication

| | Polymethyl methacrylate (PMMA) | Polycarbonate (PC) | Cycloolefin copolymer (COC) | Polyimide | Polystyrene (PS) | Polydimethylsiloxane (PDMS) |
|---|---|---|---|---|---|---|
| Polymer type | Thermoplastic | Thermoplastic | Thermoplastic | Thermoplastic | Thermoplastic | Elastomer |
| Density (×103 kg/m3) | 1.16 | 1.2 | 1.02 | 1.39 | 1.05 | 1.227 |
| Glass temperature, Tg (° C.) | 106 | 150 | 90-136 | 285 | 100 | −120 |
| Useful temperature range (° C.) | (−70)-100 | (−150)-130 | (−73)-80 | (−73)-240 | (−40)-70 | (−40)-150 |
| Mold (linear) shrinkage | 0.001-0.004 | 0.005-0.007 | 0.001 | 0.0083 | 0.004-0.006 | 0.001-0.006 |
| Linear expansion coefficient (10-6° C.) | 50-90 | 68 | 60 | 45-56 | 70 | 10-19 |
| Thermal conductivity (W mK) | 0.186 | 0.21 | 0.16 | 0.2 | 0.18 | 0.17-0.3 |
| Dielectric Strength (MV/m) | 16-20 | 15-16 | — | 16-22 | 19-135 | 16-22 |
| Optical properties: | | | | | | |
| Transmission of visible light (%) | 92 | 89 | 92-94 | 87 | 90 | 91 |
| UV resistance | Good | Good | Good | Good | Poor | Good |
| Chemical resistance: | | | | | | |
| Acids | Good | Good | Good | Fair-good | Good | Fair-good |
| Alkalis | Excellent | Poor | Good | Fair-good | Good | Poor-Fair |
| Solvent | Poor | Poor | Fair-poor | Fair | Poor | Poor |
| Surface charge (native surface) | Yes | Yes | Yes | No | Yes | Yes |
| Possible fabrication methods | Injection molding, hot embossing, laser ablation | Injection molding, hot embossing, laser ablation | Injection molding, hot embossing | Injection molding, hot embossing, laser ablation | Hot embossing | Soft lithography |

Appendix C—PCB and Sensor Fabrication Design Files

PCB's are made using the Gerber x274 format.

Consumer Needs 3.2 Value of the SBIR Project, Expected Outcomes and Impact 3.2.1 Proposed Project and Key Technology Objectives We have structured the Technical Objectives of our Phase 2 proposal around the overarching project of delivering an innovative 96-well SmartPlate prototype and associated assay application protocols that are designed to address critical customer needs in addition to a robust product manufacturing technique for our device. The SmartPlate is designed to enable plate-based sensing of microenvironment parameters and automated microfluidic-enabled media exchange and perfusion capabilities in an integrated device with a footprint and well positioning that conforms to the ANSI/SLAS microplate standard. Our project builds on our successful Phase I effort, in which we developed and tested a proof of concept 2×3 (6-well) microfluidic array and associated sensor module and control electronics and used our results to develop a prototype specification for a 96-well 'SmartPlate' for precision culture, control and monitoring of living cells.

In Technical Objective 1, we will use the 96-well SmartPlate prototype specification developed in Phase 1 as the initial basis for informing the assembly of comprehensive system requirements and conceptual design documentation that will form the initial foundation of our project. Technical Objective 1 will help us to address user concerns that the plate should be conceptualized to avoid addition of unnecessary features (see customer quotes below). In parallel, we will identify, test and validate up to 3 SmartPlate applications and establish standardized protocols for their use with the SmartPlate in Technical Objective 2. In Technical Objective 3, we will design, build and test all SmartPlate subsystems and use the results to complete SmartPlate prototype system integration in Technical Objective 4. In Technical Objective 5 we manufacture and test the prototype, using the results to inform the manufacturing technique and pilot manufacturing run that will be carried out in Technical Objective 6. Technical Objective 5 will enable us to address the request of prospective users interviewed in the course of our market research who wished to see a prototype before considering further evaluation of our device (see below). In Technical Objective 7 we will field-test our device, using the standardized application protocols developed in Technical Objective 2 as the basis for our field test protocols. We reconnect with interviewees from our market research study who expressed interest in beta testing the SmartPlate. The applications development and testing in Technical Objective 2, the protoype testing for Technical Objective 5 and the field testing for Technical Objective 7 address the requirement of our interviewees for data and validation studies. The aggregate data and findings from Technical Objectives 1-7 will be used to inform preparation of a detailed manufacturing technique and final report in Technical Objective 8. Successful completion of our Phase 2 project will thus enable Cairn Biosciences to reach 5 major product development milestones:

(1) Production and comprehensive testing of a 96-well prototype SmartPlate
(2) Development of device-specific application protocols
(3) Completion of a pilot product manufacturing run
(4) Field testing of our prototype device and application protocols
(5) Delivery of a robust technique/method/specification for product manufacture In summary, the major value of our SBIR project derives from (1) our development and delivery of an innovative SmartPlate device that will enable new paradigms for cell-based assays in drug discovery and cell biology research (2) development and documentation of validated application protocols to ensure the rapid user adoption of the device and (3) delivery of a detailed manufacturing technique/method/specification to enable our device to progress through manufacturing as rapidly as possible and with minimum risk. Our project thus results in a SmartPlate prototype that can progress rapidly to successful product manufacture and commercialization.

3.2.2 Customer Needs Addressed by the Project

Our customer survey identified the complex cell culture market as being the most attractive market segment for our device, based on market size (as assessed by our secondary research, discussed further below), overall demand, unmet user needs and anticipated plate capabilities. Within the complex culture market, long-term 2D culture, induced pluripotent stem cell (iPSC) and 3D culture emerged as the most significant market opportunities. Consequently, we have structured this project (see Table 2) to build towards developing capabilities in these areas. Our Phase 2 strategy takes into account the following customer requirements for our device that were identified in the course of our market research and that are not well-addressed by current industry-standard workflows or other commercially available devices:

- Compatibility with a range of commercially available instrumentation for cell-based assays such as plate-readers, robotics, plate hotels
- Suitability for upgrades to ensure compatibility with emerging new platforms
- Compatibility with imaging instrumentation considered critical
- Construction with proven biocompatible and assay-compatible materials.
- Allow the monitoring, reporting and on-the-fly analysis of cell culture conditions and environmental parameters required for long-term cell culture or shorter term assay manipulations (e.g. temperature, pH, flow rate, confluency, metabolite detection).
- Automated, flexible fluid handling to support addition and exchange of reagents for routine cell culture (adherent, suspension and induced pluripotent stem cell (iPSC) culture and differentiation) and perfusion for 3D models
- Serial compound dilutions and combinatorial test compound additions
- Ease of use for routine and reproducible laboratory work by technician-level employees Implementing a SmartPlate that meets the requirements listed above will enable our device to address unmet customer needs in the fields of (1) long-term 2D cell culture and suspension cell culture-based assays; (2) induced pluripotent stem cell (iPSC) culture and differentiation; (3) development of 3D cell culture models; and (4) the use of assays that leverage these cell types and cellular models.

Our interview respondents working in these areas repeatedly cited the need for new technologies to address media exchange in long term cell culture-based assays, providing examples of the 2-3 week timeline to conduct clonogenic assays for oncology drug discovery, the typical 3 week duration of macrophage-based assays conducted in standard well-plates that require daily manual media changes and the 'technician-heavy' protocols for 3D cell culture model development. These same interviewees noted that, while robotics are well-suited for HTS applications, there is no cost-effective solution for automated long-term assays involving cell culture maintenance in 96-well plate. Furthermore, these interviewees all cited the need for increased assay control and automation to improve reliability and boost throughput.

Based on our interviews, the need for new approaches to optimize and standardize protocols to ensure reliability appears to be most acute for researchers working with iPS cells. These researchers noted that iPSCs are particularly sensitive to changes in environments, making the microenvironment monitoring capabilities of our plate a desirable feature for this community.

In light of the range of pressing customer needs identified by our market research that can be addressed by our SmartPlate, we are confident that our device will rapidly gain market traction. Furthermore, we leverage our SmartPlate to support and accelerate our internal live cell high-content screening assay development and iPSC model development activities.

3.2.3 Innovation and Commercial Applications

The use of advanced cell-based disease models and long-term live cell assays in drug discovery is increasing rapidly. Maintaining these cellular systems in industry standard multiwell plates typically relies on repeated cumbersome and time-consuming visual inspections and manual media exchanges. New approaches to enable the efficient monitoring and manipulation of cell cultures in multiwell plates over a period of several weeks are therefore needed.

The SmartPlate prototype device may form the foundation for development of a novel line of SmartPlate products configured to address the needs of customers implementing complex cell culture approaches, including culture of iPSC cells, cocultures and 3D cell models, and associated assays (see Table 3). We anticipate that researchers working in these areas will be our initial customers and their needs will drive the commercial applications of our product. Innovative application protocols may validate the use of the SmartPlate and illustrate its ability to address critical customer needs.

Our device is configured for microfluidic-enabled cell culture, control and monitoring in a 96-well format, in contrast with existing commercially available microfluidic plates which have up to only 32 wells (Fluidigm Callisto plates). Furthermore, we have designed our prototype to be compatible with independent addressing of each well, enabling use of wells for either experimental purposes, or as reservoirs for assay reagents according to experimental needs. Collectively, these features of the microfluidic module of our chip addresses the customer need for automated solution for long term culturing of cells in 96-well format.

In contrast with existing related commercial products, we have designed our plate to be compatible with as wide a range of plate-reader and microscopy instrumentation as possible and to be adaptable to a wide range of applications. Instrument compatibility is ensured by the plate dimensions that conform to SBS/ANSI standards for plate footprint and well positions. The innovative modular design of our microfluidic plate enables its straightforward adaption to a wide-range of cell biology applications by substituting well-layers with different materials, coatings or well-shapes according to experimental needs, enabling the extension of the product line to address a wide-range of applications.

The integration of our microfluidic module with a reusable sensor module represents a further innovative aspect of our product that is not addressed by related commercially available products. The sensor module prototype is designed to enable closed-loop control and monitoring of microenvironment parameters with the ability to broadcast measured values by WiFi and is fully reusable.

Lastly, we have paid close attention to manufacturing cost of our SmartPlate device and drive down costs by using a streamlined microfluidic design that minimizes associated manufacturing cost and prioritizing the use of commercially available OEM components in our sensor module. These innovations will ensure that the resulting plate is competitively priced compared to existing products. In summary, our project will deliver a validated prototype of a highly innovative 96-well SmartPlate that is optimized to address customer needs and is poised for rapid manufacture and commercialization at a competitive price point.

3.2.4 Societal Benefits

Our SmartPlate product and the next-generation cell-based assays and models it will enable will benefit public health by significantly enhancing the throughput and robustness of live cell systems used to evaluate the efficacy of therapeutics, in turn improving the ability to identify beneficial therapies for unmet medical needs. Our SmartPlate, combined with Cairn Biosciences' innovative live cell high-content assays and iPS cell-based models will enable academic and industry researchers to develop a better understanding of the nature of dynamic fluctuations of phenotypic states within diseased cell subpopulations and the role the consequent heterogeneity plays in disease evolution and response to drug treatment.

There is an industry need for and commercial potential of new assays that interrogate previously inaccessible disease biology and thus increase the pace and precision of preclinical drug discovery. Disclosed herein are various solutions that address that need, including state-of-the art cell-based assays and related technologies and an innovative SmartPlate that enables new formats of cell-based assays is in close alignment with our company mission. These solutions are compatible with innovative high-throughput live-cell microscopy assay platforms and next-generation iPSC model engines as discussed further below. The solutions disclosed herein will address several important needs of iPSC researchers and that compatibility with imaging instrumentation and/or built in imaging capabilities are a high-priority for end-users of our SmartPlate. The disclosures herein enable a SmartPlate that is optimally configured to address customer needs and that has been tested and validated in the context of protocols that are tailored to the priority applications of the end-users of our device.

3.2.5 SmartPlate Applications

Application areas may include complex culture; toxicity testing; and drug discovery. Within the complex culture market, induced pluripotent stem cell (iPSC) and 3D culture may be significant areas of applicability. Biopharma scientists working in the areas of disease modeling using iPSCs and 3D cultures may have needs for solutions described herein. Since iPSC-based assays and models are gaining traction in toxicity assessment for pharmaceutical compounds and disease modeling for neuronal disorders, scientists working in these areas may have needs for solutions described herein. Cancer research applications of our SmartPlate also presents a promising potential area of applicability, since it accounts for ~40% of the sizeable 3D cell culture market.

Applications in the global cell-based assay market may include 3D models and iPSCs. Scaffold-based 3D models and the differentiation and analysis segments of the iPSC market may be important applications for implementation in microfluidic-enabled formats. 3D scaffold-based models may be an important application within the 3D culture market space. Cell analysis and differentiation sub-segments may be an important application within the iPSC space.

The increasing need for the solutions described herein, particularly with regard to broad cell-based assays, may be driven by: increased R&D spending; growing benefits of cell based assays over other methods; increasing adoption of cell based assays in drug discovery and advances in automation and high-throughput techniques compatible with cell based assays[2,10]. The growth of cell based assays in drug discovery is largely due to their emergence as more relevant alternatives to biochemical screening[2,10]. Furthermore, need for the solutions described herein may be rapidly increasing for the in vitro toxicology testing cell based assay market, which may be being driven by the increasing acceptance of in vitro methods over in vivo studies. Furthermore, government initiatives and regulatory pressure to substitute animal testing with new and promising technologies is spurring growth of this segment[7].

One application for our proposed Smart-Plate is cell-based assays within the lab analytics group of applications within drug discovery. We appreciate that our device may also have applications within the adjacent application segment of in vitro diagnostics.

Switching Costs

Switching costs associated with adopting an additional or alternative provider of a consumable are chiefly associated with the costs to implement a new device and reconfigure existing assays to a new consumable format. We believe this barrier is greatly mitigated by the fact that our device may conform to the dimensions of 96-well plates that are widely adopted as a workhorse consumable by life science researchers. Additionally, we believe any perceived residual switching cost is far outweighed by having a plate with additional capabilities including microfluidic and sensor capabilities. We consider that the switching costs associated with switching from a competitor product are relatively small since neither the Fluidigm Callisto or CellAsic Onix systems are especially well established and our product is greatly differentiated from their offerings.

Product Differentiation

The solutions and products described herein differentiate themselves clearly from known solutions. The solutions and products described herein prioritize features that align directly with customer needs 3.2.6 Competitive Landscape and Smart Plate Advantages We identified these competitors by researching market literature, reviewing company reports, websites and catalogs and by interviewing customers to generate a detailed snapshot of each competitor's size, location, revenue, major corporate events, key services and major customers.

From our analysis, certain differentiating strengths of our Smart-Plate platform when compared with competing products are (1) its compatibility with imaging instrumentation and suitability for future incorporation of imaging capabilities; (2) microenvironment control and monitoring and compatibility with confluency monitoring; and (3) it high density 96-well format which greatly exceeds the number of wells on any other commercially available device.

The SmartPlate thus has several significant advantages in terms of (1) improved and new capabilities compared with existing products; (2) well defined and validated application protocols and (3) a more cost-effective price point than competing devices. In summary, we believe the sparsely populated competitive landscape and the significant differentiation of our SmartPlate compared with existing products presents an exciting opportunity for the SmartPlate to meet customer needs.

A product development technique in accordance with some embodiments for our Smart-Plate platform is summarized in Table 3. We may take an application-centric approach to product development by developing Smart-Plate modules that enable a broad general capability, e.g. initially long-term routine 2D cell culture, and a suite of associated applications for which we will develop SOPs. The plate and associated Application SOPs thus lay the groundwork of our product development strategy. Subsequently developed capabilities may require the successive upgrade of different Smart-Plate module capabilities to enable successively more challenging capabilities and applications, e.g. upgrading our basic microfluidic-enabled 2D culture substrate to a specialized substrate to enable long-term complex 2D cell culture capabilities. This product development concept may be further developed and validated in the course of application development. The Smart-Plates described herein may be compatible with and/or may include control boxes, reusable sensor modules, and microfluidic modules comprising a semi-reusable pneumatic activation layer (manufactured in glass and thus autoclavable) and disposable microfluidic substrates.

TABLE 3

Application-centric 4-phase product development technique commences with development of Smart-Plate modules to enable (1) routine 2D-culture capabilities and development of associated applications. Downstream capabilities (2-4) are enabled by stepwise upgrade of relevant Smart-Plate modules (bold) and development of associated application SOPs.

| | Capability | Application examples | Smart-Piste modules |
|---|---|---|---|
| 1 | (Long-term (weeks) routine 2D cell culture | Clonogenic end-point assays<br>Survival assays<br>Transfection and selection | Basic microfluidic-enabled 2D culture substrate<br>Basic liquid handling<br>Basic microenvironment sensing and control (Temperature, pH, confluency)<br>Low resolution image-based monitoring |
| 2 | Long-term complex 2D cell culture maintenance | Differentiated iPSC maintenance<br>Primary cell maintenance<br>Co-cultures | **Specialized microfluidic 2D culture substrate**<br>Basic liquid handling<br>**Precision microenvironment sensing and control (Temperature, pH, confluency)**<br>**Low-medium resolution image-based monitoring** |
| 3 | Precision timed addition/washout of reagents to cultures | iPSC differentiation<br>iPSC reprogramming<br>Precise timed compound addition<br>Live cell high-content assays | Microfluidic culture substrate according to application<br>**Precision, timed liquid handling**<br>Basic/Precision microenvironment sensing and control according to application<br>**Medium-high resolution time-lapse image-based monitoring** |
| 4 | 3D culture-based models | Tumor spheroids<br>Vascular networks<br>Bioprinted 3D tissue models<br>iPSC-derived 3D tissue models | **Specialized microfluidic 3D culture substrate**<br>Precision, timed liquid handling<br>Precision microenvironment sensing and control according to application<br>Medium-high resolution time-lapse image-based monitoring |

4 STATEMENT OF WORK

I Background Information and Objectives

A. Background Information

The use of advanced cell-based disease models and long-term live cell assays in drug discovery is increasing rapidly. Maintaining these cellular systems in industry standard multiwell plates typically relies on repeated cumbersome and time-consuming visual inspections and manual media exchanges. New approaches to enable the efficient monitoring and manipulation of cell cultures in multiwell plates over a period of several weeks are therefore needed. We address this need by delivering a multiwell SmartPlate that enables plate-based sensing of microenvironment parameters and automated microfluidic-enabled media exchange and perfusion capabilities in an integrated device with a footprint and well positioning that conforms to the ANSI/SLAS microplate standard.

B. Phase II Technical Objectives

Technical Objective 1: Develop initial SmartPlate prototype concept and requirements Technical Objective 2: Identification, test and validation of SmartPlate applications Technical Objective 3: Specify, build and test all SmartPlate prototype subsystems Technical Objective 4: SmartPlate prototype system integration Technical Objective 5: SmartPlate prototype manufacture and test Technical Objective 6: SmartPlate product manufacturing pilot Technical Objective 7: Field test SmartPlate product Anticipated End Results:

A multiwell SmartPlate prototype and complete a pilot manufacturing run is provided.

Technical Objective 1: Develop Initial SmartPlate Prototype Concept and Requirements In TO1 we will develop initial SmartPlate prototype concept and requirements that will be informed by our experimental data, user feedback and market research findings.

Tasks

Task 1.1 Cell Experiments in Proof of Concept Device

We will establish a reliable protocol for successful culture of cells for 2 weeks in our proof-of-concept 2×3 microfluidic array.

Task 1.2 Initial Product System Requirements

We will refine and document intended use and basic top level requirements for our device.

Task 1.3 Initial Product Conceptual Design

We will develop and document detailed concept design(s) that will meet the requirements identified in Task 1.2.

Task 1.4 Specify OEM Components and Identify Custom Component Needs

We will write a bill of materials encompassing OEM and custom components required to build a prototype SmartPlate.

Technical Objective 2: Identification, Test and Validation of SmartPlate Applications The main focus of this technical objective will be on the application specific system requirements and evaluation of key parameters to implement cell based assay applications.

Task 2.1 Identification and Prioritization of SmartPlate Applications

We will define and identify potential applications for the SmartPlate prototype based on the current design and system features and market research data.

Task 2.2 Application Testing on the SmartPlate Prototype

We will test the applications identified in T2.1 in our SmartPlate prototype.

Technical Objective 3: Specify, Build and Test all SmartPlate Prototype Subsystems The main objective of this TO is to characterize and qualify components and subsystems to be compliant with our previously documented system requirements and concepts.

Tasks

Task 3.1 Design Custom Components

For those features where OEM and off-the-shelf components are missing we will design custom sub-components.

Task 3.2 Write Initial Specification to Meet System Requirements & Solicit User Feedback We will prepare detailed specification data-sheets for each of the sub-components with its performance estimations and limitations.

Task 3.3 Test OEM Components; Build and Test Custom Components

We will order OEM and off-the-shelf parts for the individual systems sub-components will be ordered, assembled and tested.

Task 3.4 Subsystem Build and Test

We will assemble the OEM and custom components into subsystems and test them.

Technical Objective 4: SmartPlate Prototype System Integration

In this Technical Objective we will rigorously test and characterize the subsystems built in TO5 and use prioritized components as the basis for the design of 2 candidate prototype systems.

Tasks

Task 4.1 Prototype System Design x2

Design 2 candidate prototypes using prioritized subsystems.

Task 4.2 Mechanical Layout x2

Based on system requirements and the characteristics of the various subsystems, define the physical relationships of the subsystems and their interfaces.

Task 4.3 Detailed Mechanical Design

Given complete mechanical layouts, perform detailed mechanical design and electromechanical integration design sufficient to build a prototype.

Task 4.4 Electrical Design x2

Given the system designs defined in TO4.1, perform schematic-level electrical design and breadboard testing.

Technical Objective 5: SmartPlate Prototype Manufacture and Test

We will build and test two prototypes and select one prototype design for manufacture. The selected design will undergo a Design for Manufacturability (DFM) phase, wherein a design package will be completed in preparation for a pilot manufacturing run.

Tasl 5.1 Manufacture Top 2 Prototype Designs

We will manufacture a small quantity (up to 10 each) of the 2 prototypes.

Task 5.2 Repeat Test Protocols on Prototype Systems

We will test the prototypes to confirm compliance with requirements and discover strengths and weaknesses.

Task 5.3 Alpha Test (User)

We will engage select users to test our prototypes using detailed protocols that we will develop.

Task 5.4 Down-Selection

After analyzing the results of the Alpha test and other concurrent internal testing, we will prioritize a single prototype design for manufacture.

Task 5.5 Final Product Design for Manufacture

Adapt system design to accommodate chosen component production manufacturing methods and integrate chosen subsystems into a final, manufacturable design.

Technical Objective 6: SmartPlate Product Manufacturing Pilot

We will working with a contract manufacturer to refine our design for manufacturing persons and to then complete a pilot manufacturing run with product to be be warehoused and shipped to field-test sites.

Tasks

Task 6.2 Execute SmartPlate Manufacturing Pilot

Using only final-intent production methods wherever possible, produce up to 100 SmartPlate units.

Task 6.3 Drop-Ship Product to Field-Test Sites

Using warehousing and order fulfillment methods, deliver production-intent units to test sites for evaluation.

Technical Objective 7: Field Test SmartPlate Product

We will develop standard field test protocols and provide them to field-testers who will test our device in their laboratories. Data gathered from these tests will be analyzed.

Task 7.1 Define Field Test Protocol

We will develop application protocols and a device user manual to guide users during the field-test of our device.

Task 7.2 Conduct Field Test

Selected users will field-test the device in their laboratories.

Task 7.3 Field Test Data Analysis

The gathered data and experiences from the field test will be analyzed and the overall system performance investigated.

Below is an enumerated listing of certain embodiments. In some embodiments, any one or more of the features of any one or more of the embodiments below may be combined with any one or more of the other embodiments, even if the dependencies of the embodiments do not explicitly indicate that the embodiments may be combined.

1. A microfluidic-enabled multiwell device for microfluidic control of fluids for cell cultures comprising:
   a microfluidics module comprising a well layer, a fluid channels layer, and a pneumatic layer,
   a sensor module comprising one or more sensors configured to detect data regarding an environment inside the microfluidic module; and
   one or more processors; and
   memory storing instructions configured to be executed by the one or more processors to cause the multiwell device to execute a cell culture process, comprising:
   receiving data collected from the one or more sensors regarding the environment inside the microfluidic module; and
   based at least in part on the data received, causing fluid to flow to an individually addressable well in the multiwell device.
2. The microfluidic-enabled multiwell device of embodiment 1, wherein the microfluidic-enabled multiwell device further comprises a substrate layer.
3. The microfluidic-enabled multiwell device of any one of embodiments 1-2, wherein the pneumatic layer comprises a pneumatic well-selection layer and pneumatic control layer.
4. The system of any one of embodiments 1-3, wherein the microfluidics module comprises a degasser layer comprising a plurality of well-specific degassers each configured to remove gas bubbles from a specific well in the well layer.
5. The system of embodiment 4, wherein the microfluidics module comprises a gas-permeable degasser membrane between the well layer and the degasser layer.
6. The system of any one of embodiments 4-5, wherein the microfluidics module comprises a degasser control layer comprising a plurality of pneumatic channels pneumatically coupled to one or more of the well-specific degassers.
7. The system of any one of embodiments 4-6, wherein the microfluidics module comprises a global degasser configured to remove gas bubbles from a fluid channel configured to deliver fluid to two or more of the wells of the well layer.
8. The microfluidic-enabled multiwell device of any one of embodiments 1-7, further comprising a control module.
9. The microfluidic-enabled multiwell device of embodiment 8, wherein at least one of the one or more processors are comprised in the control module.
10. The microfluidic-enabled multiwell device of any one of embodiments 1-9, wherein: the microfluidics module comprises a plurality of pumps; and causing fluid to flow to an individual well in the multiwell device comprises causing one or more of the plurality of pumps to be actuated.
11. The microfluidic-enabled multiwell device of embodiment 10, wherein the plurality of pumps comprise one or more of a syringe driven pump, a micro-diaphragm pump, a pneumatic micropump with doormat valve geometry, or a pneumatic micropump with lifting gate valve geometry.
12. The microfluidic-enabled multiwell device of any one of embodiments 1-11, wherein the multiwell device comprises one or more microfluidics module sensors integrated into the microfluidic module of the multiwell device, wherein the one or more microfluidics module sensors are configured to detect a characteristic of a parameter of the environment inside the microfluidic module.
13. The microfluidic-enabled multiwell device of any one of embodiments 1-12, wherein the sensor layer comprises one or more sensors configured to detect an external characteristic of an environment surrounding the multiwell device.
14. The microfluidic-enabled multiwell device of any one of embodiments 1-13, wherein the instructions are configured to be executed by the one or more processors to cause the device to store, in the memory, the data collected from the one or more sensors regarding the environment inside the microfluidic module.
15. The microfluidic-enabled multiwell device of any one of embodiments 1-14, wherein the instructions are configured to be executed by the one or more processors to cause the device to transmit, to a remote computing device for storage, the data collected from the one or more sensors regarding the environment inside the microfluidic module.
16. The microfluidic-enabled multiwell device of any one of embodiments 1-15, wherein the instructions are configured to be executed by the one or more processors to cause the device to:
   transmit instructions for displaying a graphical user interface;
   detect an input executed by a user of the device via the graphical user interface; and
   in response to detecting the input, cause fluid to flow to a user-indicated individual well of the multiwell device.
17. The microfluidic-enabled multiwell device of any one of embodiments 1-16, wherein a footprint of the multiwell device conforms to one or more SBS/ANSI multiwell plate standards.
18. The microfluidic-enabled multiwell device of any one of embodiments 1-17, wherein the multiwell device is compatible with one of industry-standard laboratory plate-reading and industry-standard automation equipment.
19. The microfluidic-enabled multiwell device of any one of embodiments 1-18, wherein one or more of the microfluidic module and the sensor module are configured to be reusable for multiple cell culture procedures.
20. The microfluidic-enabled multiwell device of any one of embodiments 1-19, wherein one or more of the microfluidic module and the sensor module are configured to be removable from the multiwell device.
21. The microfluidic-enabled multiwell device of any one of embodiments 1-20, wherein one or more of the microfluidic module and the sensor module are configured to be removable from the multiwell device following a first cell culture procedure for replacement by another component prior to a second cell culture procedure.

22. The microfluidic-enabled multiwell device of any one of embodiments 1-21, wherein the well layer is configured to be removable from the microfluidics module.

23. The microfluidic-enabled multiwell device of any one of embodiments 1-22, wherein the well layer is configured to be removable from the microfluidics module following a first cell culture procedure for replacement by another component prior to a second cell culture procedure.

24. The microfluidic-enabled multiwell device of any one of embodiments 1-23, wherein the well layer comprises one or more of glass, cyclo-olefin copolymer, plastics, or PDMS.

25. The microfluidic-enabled multiwell device of any one of embodiments 1-24, wherein a coating of the well layer comprises one or more of poly-lysine, fibronectin, or matrigel.

26. The microfluidic-enabled multiwell device of any one of embodiments 1-25, wherein the well layer is micropatterned.

27. The microfluidic-enabled multiwell device of any one of embodiments 1-26, wherein one or more of a thickness, material, micropatterning, coating, and geometrical configuration of the well layer are configured for microscopic imaging.

28. The microfluidic-enabled multiwell device of any one of embodiments 1-27, wherein one or more of a material, micropatterning, coating, and geometrical configuration of the well layer are configured for 2D culture of adherent cells.

29. The microfluidic-enabled multiwell device of any one of embodiments 1-28, wherein one or more of a material, micropatterning, coating, and geometrical configuration of the well layer are configured for co-culture of more than one type of adherent cell.

30. The microfluidic-enabled multiwell device of any one of embodiments 1-29, wherein one or more of a material, micropatterning, coating, and geometrical configuration of the well layer are configured for co-culture of adherent cells with other cell types.

31. The microfluidic-enabled multiwell device of any one of embodiments 1-30, wherein one or more of a material, micropatterning, coating, and geometrical configuration of the well layer are configured for culture of suspension cells.

32. The microfluidic-enabled multiwell device of any one of embodiments 1-31, wherein one or more of a material, micropatterning, coating, and geometrical configuration of the well layer are configured for culture of 3D culture models.

33. The microfluidic-enabled multiwell device of embodiment 32, wherein the 3D models comprise one or more of tumor spheroids, organoids, vascular networks, bioprinted 3D tissue models, and iPSC-derived 3D tissue models.

34. The microfluidic-enabled multiwell device of any one of embodiments 1-33, wherein one or more of a material, micropatterning, coating, and geometrical configuration of the well layer are configured for culture of one or more of immortalized cells, iPSC, iPSC-derived, or primary cells.

35. The microfluidic-enabled multiwell device of any one of embodiments 1-34, wherein the instructions are configured to be executed by the one or more processors to cause multiwell device to control fluid for the cell culture process for at least 24 hours.

36. The microfluidic-enabled multiwell device of any one of embodiments 1-35, wherein causing fluid to flow to an individually addressable well comprises causing a valve to be actuated in association with displacement of a portion of the pneumatic layer.

37. The microfluidic-enabled multiwell device of any one of embodiments 1-36, wherein the instructions are configured to be executed by the one or more processors to cause the multiwell device to cause perfusion of one or more of nutrients, reagents, and media to a plurality of individually-addressable wells in the multiwell device in accordance with a predefined procedure for one or more of 2D culture of adherent cells, co-culture of more than one type of adherent cell, co-culture of adherent cells with other cell types, culture of suspension cells, culture of 3D culture models, culture of immortalized cells, culture of iPSC, culture of iPSC-derived, or culture of primary cells.

38. The microfluidic-enabled multiwell device of any one of embodiments 1-37, wherein the microfluidic module comprises one or more channels having a diameter of less than 1000 μm.

39. The microfluidic-enabled multiwell device of any one of embodiments 1-38, wherein one or more micropumps of the microfluidic module are configured to pump a volume of less than 500 nL per pump stroke.

40. The microfluidic-enabled multiwell device of any one of embodiments 1-39, comprising an array of 96 or more individually-addressable wells.

41. The microfluidic-enabled multiwell device of any one of embodiments 1-40, wherein the instructions are configured to be executed by the one or more processors to cause the microfluidic module to cause automated exchange of cell culture media.

42. The microfluidic-enabled multiwell device of any one of embodiments 1-41, wherein the instructions are configured to be executed by the one or more processors to cause the microfluidic module to cause automated trypsinization of cultured cells.

43. The microfluidic-enabled multiwell device of any one of embodiments 1-42, wherein the instructions are configured to be executed by the one or more processors to cause the microfluidic module to cause automated passaging of cells.

44. The microfluidic-enabled multiwell device of any one of embodiments 1-43, wherein the instructions are configured to be executed by the one or more processors to cause the device to execute an automated cell-based assay and protocol in the multiwell device.

45. The microfluidic-enabled multiwell device of embodiment 44, wherein the instructions are configured to be executed by the one or more processors to cause the device to monitor the assay for a period of at least 24 hours during execution of the assay.

46. The microfluidic-enabled multiwell device of any one of embodiments 44-45, wherein the executing the assay comprises causing the automated addition of one or more compounds to cells.

47. The microfluidic-enabled multiwell device of any one of embodiments 44-46, wherein the assay is a clonogenic assay.

48. The microfluidic-enabled multiwell device of any one of embodiments 44-47, wherein the protocol is a transfection protocol.

49. The microfluidic-enabled multiwell device of any one of embodiments 44-48, wherein the protocol comprises reprogramming cells to induce pluripotency.

50. The microfluidic-enabled multiwell device of any one of embodiments 44-49, wherein the protocol is a protocol to differentiate pluripotent cells.

51. The microfluidic-enabled multiwell device of any one of embodiments 44-50, wherein the assay is one of a high-throughput cell based assay, a survival assay, a viral passaging assay, a clonogenic assays beyond oncology, a T-Cell clone, an assay to evaluate therapeutic resistance, or an assay to evaluate therapeutic resistance evolution.

52. The microfluidic-enabled multiwell device of any one of embodiments 44-51, wherein the assay comprises microscopy measurements.

53. The microfluidic-enabled multiwell device of any one of embodiments 44-52, wherein cells of the assay comprise one or more of immortalized cells, primary cells, pluripotent cells, pluripotent-derived cells, adherent cells, or suspension cells.

54. The microfluidic-enabled multiwell device of any one of embodiments 44-53, wherein cells of the assay are derived from a clinical sample.

55. The microfluidic-enabled multiwell device of any one of embodiments 44-54, wherein cells subject to the assay comprise one or more of a 3D culture model, an organoid model, and a coculture model.

56. The microfluidic-enabled multiwell device of any one of embodiments 44-55, wherein cells subject to the assay comprise reporter cells.

57. The microfluidic-enabled multiwell device of any one of embodiments 44-56, wherein cells subject to the assay comprise a library of cells arrayed in the device.

58. The microfluidic-enabled multiwell device of any one of embodiments 44-57, wherein the assay and protocol is conducted without tissue culture incubators.

59. The microfluidic-enabled multiwell device of any one of embodiments 44-58, wherein the assay and protocol is conducted in a laboratory environment.

60. The microfluidic-enabled multiwell device of any one of embodiments 44-59, wherein assay and protocol is conducted in one of a field location, a point-of-care location, and a pharmacy.

61. The microfluidic-enabled multiwell device of any one of embodiments 1-60, wherein the cell culture is conducted without tissue culture incubators.

62. The microfluidic-enabled multiwell device of any one of embodiments 1-61, wherein at the cell culture is conducted in a laboratory environment.

63. The microfluidic-enabled multiwell device of any one of embodiments 1-62, wherein at the cell culture is conducted in one or more of a field location, a point-of-care, and a pharmacy.

64. The microfluidic-enabled multiwell device of any one of embodiments 1-63, wherein at the well layer contains cryopreserved cells that are thawed during the cell culture.

65. The microfluidic-enabled multiwell device of any one of embodiments 1-64, wherein the instructions are configured to be executed by the one or more processors to cause the device to:

in accordance with receiving the data collected from the one or more sensors regarding the environment inside the microfluidic module, control one or more parameters of an environment inside the microfluidics module, wherein the one or more parameters includes one or more of temperature, pressure, pH, humidity, CO2, O2, confluency, fluid flow, alkalinity, input fluid temperature, output fluid temperature, or ambient light intensity.

66. The microfluidic-enabled multiwell device of any one of embodiments 1-65, wherein the instructions are configured to be executed by the one or more processors to cause the device to:

monitor, by the sensor module, one or more parameters of an environment surrounding the multiwell device;

store data regarding the monitoring of the parameters of the environment surrounding the multiwell device on a computer storage of the device; and wirelessly transmit the stored data regarding the monitoring of the parameters of the environment surrounding the multiwell device to a user.

67. The microfluidic-enabled multiwell device of any one of embodiments 1-66, wherein the instructions are configured to be executed by the one or more processors to cause the device to:

monitor, by the sensor module, one or more parameters of an environment surrounding the multiwell device;

in accordance with monitoring one or more environmental parameters, adjust one or more parameters of the environment inside the microfluidics module.

68. The microfluidic-enabled multiwell device of any one of embodiments 1-67, wherein:

the well layer comprises a first plurality of wells arranged into a plurality of rows;

the fluid channels layer comprises a first input channel and a first output channel both corresponding to a first row of the plurality of rows;

the fluidic channels layer comprises a second input channel and a second output channel both corresponding to a second row of the plurality of rows;

two wells in the first row are individually fluidly connectible to the first input channel by a first plurality of respective input valves;

the two in the first row are individually fluidly connectible to the first output channel by a first plurality of respective output valves;

two wells in the second row are individually fluidly connectible to the second input channel by a second plurality of respective input valves;

the two wells in the second row are individually fluidly connectible to the second output channel by a second plurality of respective output valves.

69. The microfluidic-enabled multiwell device of embodiment 68, wherein:

the first input channel is fluidly connectible to a common input channel via a first channel input valve;

the first output channel is fluidly connectible to a common output channel via a first channel output valve;

the second input channel is fluidly connectible to the common input channel via a second channel input valve;

the second output channel is fluidly connectible to the common output channel via a second channel output valve.

70. The microfluidic-enabled multiwell device of embodiment 69, wherein causing fluid to flow to an individually addressable well in the multiwell device comprises:

opening the first channel input valve and the first channel output to allow flow into and out of the first output channel;

opening one of the first plurality of input valves and a corresponding one of the first plurality of output valves to allow flow into and out of the individually addressable well.

71. The microfluidic-enabled multiwell device of any one of embodiments 68-70, wherein a micropump is configured to provide vacuum force to selectively cause flow through any individual well of the two wells in the first row and the two wells in the second row.

72. The microfluidic-enabled multiwell device of embodiment 71, wherein the micropump is downstream from the common output channel.

73. The microfluidic-enabled multiwell device of any one of embodiments 1-72, wherein the device is configured to be received by a docking component.

74. The microfluidic-enabled multiwell device of embodiment 73, wherein the device is configured to be fluidly coupled to the docking component.

75. The microfluidic-enabled multiwell device of any one of embodiments 73-74, wherein the device is configured to be pneumatically coupled to the docking component.

76. The microfluidic-enabled multiwell device of any one of embodiments 73-75, wherein the device is configured to be electronically communicatively coupled to the docking component.

77. A system for microfluidic control of fluids for cell cultures, wherein the system comprises:

the microfluidic-enabled multiwell device of any one of embodiments 1-76; and a docking component configured to receive the multiwell device and to be fluidly coupled to the multiwell device.

78. The system of embodiment 77, wherein the docking component is configured to be pneumatically coupled to the device.

79. The system of any one of embodiments 77-78, wherein the docking component is configured to be electronically communicatively coupled to the device.

80. The system of any one of embodiments 77-79, wherein the docking component comprises a tabletop docking station.

81. The system of any one of embodiments 77-80, wherein the docking component comprises a portable docking module configured to enable operation of the multiwell device when the portable docking module is inserted in one or more of a plate reader or a microscope stage.

82. The system of any one of embodiments 77-81, wherein the docking component comprises a display configured to display a graphical user interface.

83. The system of any one of embodiments 77-82, wherein the docking component comprises a user input device configured to receive a user input comprising an instruction.

84. The system of any one of embodiments 77-83, comprising an inkjet input reservoir system configured to be fluidly coupled to the multiwell device and to supply one or more of media, cell suspension, and reagents to the multiwell device.

85. The system of any one of embodiments 77-84, comprising an output reservoir configured to be fluidly coupled to the multiwell device and to receive flow of one or more of media, cell suspension, and reagents from the multiwell device.

86. The system of any one of embodiments 77-85, comprising a manifold configured to attach to one or more of a reservoir or a vacuum line.

87. A method for microfluidic control of fluids for cell cultures, comprising:

at a microfluidic-enabled multiwell device comprising a microfluidics module comprising a well layer, a fluid channels layer, and a pneumatic layer; and a sensor module comprising one or more sensors configured to detect data regarding an environment inside the microfluidic module:

receiving data collected from the one or more sensors regarding the environment inside the microfluidic module; and based at least in part on the data received, causing fluid to flow to an individually addressable well in the multiwell device.

88. The method of embodiment 87, comprising, at the microfluidic-enabled multiwell device, storing the data collected from the one or more sensors regarding the environment inside the microfluidic module.

89. The method of any one of embodiments 87-88, comprising, at the microfluidic-enabled multiwell device, transmitting, to a remote computing device for storage, the data collected from the one or more sensors regarding the environment inside the microfluidic module.

90. The method of any one of embodiments 87-89, comprising, at the microfluidic-enabled multiwell device:

transmitting instructions for displaying a graphical user interface;

detecting an input executed by a user of the device via the graphical user interface; and in response to detecting the input, causing fluid to flow to a user-indicated individual well of the multiwell device.

91. The method of any one of embodiments 87-90, comprising, at the microfluidic-enabled multiwell device, controlling fluid for the cell culture process for at least 24 hours.

92. The method of any one of embodiments 87-91, wherein causing fluid to flow to an individually addressable well comprises causing a valve to be actuated in association with displacement of a portion of the pneumatic layer.

93. The method of any one of embodiments 87-92, comprising, at the microfluidic-enabled multiwell device:

in accordance with receiving the data collected from the one or more sensors regarding the environment inside the microfluidic module, controlling one or more parameters of an environment inside the microfluidics module, wherein the one or more parameters includes one or more of temperature, pressure, pH, humidity, CO2, O2, confluency, fluid flow, alkalinity, input fluid temperature, output fluid temperature, or ambient light intensity.

94. The method of any one of embodiments 87-93, comprising, at the microfluidic-enabled multiwell device:

monitoring, by the sensor module, one or more parameters of an environment surrounding the multiwell device;

storing data regarding the monitoring of the parameters of the environment surrounding the multiwell device on a computer storage of the device; and wirelessly transmitting the stored data regarding the monitoring of the parameters of the environment surrounding the multiwell device to a user.

95. The method of any one of embodiments 87-94, comprising, at the microfluidic-enabled multiwell device:

monitoring, by the sensor module, one or more parameters of an environment surrounding the multiwell device;

in accordance with monitoring one or more environmental parameters, adjusting one or more parameters of a the environment inside the microfluidics module.

96. The method of any one of embodiments 87-95, wherein:

the well layer comprises a first plurality of wells arranged into a plurality of rows;

the fluid channels layer comprises a first input channel and a first output channel both corresponding to a first row of the plurality of rows;

the fluidic channels layer comprises a second input channel and a second output channel both corresponding to a second row of the plurality of rows;

two wells in the first row are individually fluidly connectible to the first input channel by a first plurality of respective input valves;

the two in the first row are individually fluidly connectible to the first output channel by a first plurality of respective output valves;

two wells in the second row are individually fluidly connectible to the second input channel by a second plurality of respective input valves;

the two wells in the second row are individually fluidly connectible to the second output channel by a second plurality of respective output valves;

the first input channel is fluidly connectible to a to a common input channel via a first channel input valve;

the first output channel is fluidly connectible to a to a common output channel via a first channel output valve;

the second input channel is fluidly connectible to a to the common input channel via a second channel input valve;

the second output channel is fluidly connectible to a to the common output channel via a second channel output valve;

causing fluid to flow to an individually addressable well in the multiwell device comprises:

opening the first channel input valve and the first channel output to allow flow into and out of the first output channel; and opening one of the first plurality of input valves and a corresponding one of the first plurality of output valves to allow flow into and out of the individually addressable well.

97. A microfluidic enabled multiwell device with closed-loop microenvironment monitoring and control, the device comprising:

a substrate module layer;

a microfluidic module layer; and a sensor module layer;

98. The device of embodiment 97, wherein the substrate module layer is disposable.

99. The device of any one of embodiments 97-98, wherein the microfluidic module layer is reusable or disposable.

100. The device of any one of embodiments 97-99, wherein the sensor module layer is reusable.

101. The device of any one of embodiments 97-100, wherein one or more of the substrate module layer, the microfluidic module layer, and the sensor module layer are configured to be removable from the device for replacement by a different layer.

102. The device of any one of embodiments 97-101 where the substrate module comprises one or more of glass and cyclo-olefin copolymer.

103. The device of any one of embodiments 97-102, wherein one or more of a thickness, material, micropatterning, coating, and geometrical configuration of the substrate module are configured for microscopic imaging.

104. The device of any one of embodiments 97-103, wherein one or more of a material, micropatterning, coating, and geometrical configuration of the substrate module are configured for 2D culture of adherent cells.

105. The device of any one of embodiments 97-104, wherein one or more of a material, micropatterning, coating, and geometrical configuration of the substrate module are configured for co-culture of more than one type of adherent cell.

106. The device of any one of embodiments 97-105, wherein one or more of a material, micropatterning, coating, and geometrical configuration of the substrate module are configured for co-culture of adherent cells with other cell types.

107. The device of any one of embodiments 97-106, wherein one or more of a material, micropatterning, coating, and geometrical configuration of the substrate module are configured for culture of suspension cells.

108. The device of any one of embodiments 97-107, wherein one or more of a material, micropatterning, coating, and geometrical configuration of the substrate module are configured for culture of 3D culture models.

109. The device of embodiment 108, wherein the 3D models comprise one or more of tumor spheroids, organoids, vascular networks, bioprinted 3D tissue models, and iPSC-derived 3D tissue models.

110. The device of any one of embodiments 97-109, wherein one or more of a material, micropatterning, coating, and geometrical configuration of the substrate module are configured for one or more of culture of immortalized cells, iPSC, iPSC-derived, and primary cells.

111. The device of any one of embodiments 97-110, wherein the microfluidic module comprises one or more channels having a diameter ranging from 10-1000 μm.

112. The device of any one of embodiments 97-111, wherein the microfluidic module comprises one or more micro-pumps configured to pump volumes ranging from 10-500 nl per pump stroke.

113. The device of any one of embodiments 97-112, wherein the microfluidic module comprises pump geometries that include one or more of syringe driven pumps, micro-diaphragm pumps, and pneumatic micropumps with doormat or lifting gate valve geometries.

114. The device of any one of embodiments 97-113, wherein the sensor module applies calibration information and controls microenvironment parameters including one or more of temperature, pH, humidity, $CO_2$, $O_2$, confluency, fluid flow, input fluid temperature, output fluid temperature, a visualized 2D/3D gradient heatmap of the microfluidic/substrate layer, ambient light intensity 115. The device of any one of embodiments 97-114, wherein the sensor module collects microenvironment data for local storage.

116. The device of any one of embodiments 97-115, wherein the sensor module transmits measurements wirelessly for remote or local user interaction.

117. The device of any one of embodiments 97-116, wherein the substrate module is micropatterned.

118. The device of any one of embodiments 97-117, wherein a coating of the substrate module comprises one or more of poly-lysine, fibronectin.

119. The device of any one of embodiments 97-118, wherein the device comprises up to 96 wells.

120. The device of any one of embodiments 97-119, wherein the device comprises more than 96 wells.

121. The device of any one of embodiments 97-120, wherein a footprint of the device conforms to one or more SBS/ANSI multiwell plate standards and is compatible with a plurality of industry standard laboratory plate-reading and automation devices and equipment.

122. A method of executing and monitoring automated cell culture, comprising:
monitoring one or more cells in a multiwell microfluidic-enabled device for a period of at least 24 hours, wherein the one or more cells comprise one or more of an immortalized cell, a primary cell, a pluripotent cell, a pluripotent-derived cell, a 3D model, an organoid, and a co culture.

123. The method of embodiment 122 when the automated cell culture process includes thawing of cells that have been cryopreserved in the device of any one of embodiments 97-121.

124. The method of any one of embodiments 122-123, wherein the multiwell microfluidic-enabled device is configured for closed-loop microenvironment monitoring and control and comprises a substrate module layer, a microfluidic module layer, and a sensor module layer.

125. The method of embodiment 124, comprising:
monitoring, by the sensor module, one or more environmental parameters;
storing data regarding the monitoring on a computer storage of the device; and
wirelessly transmitting the data to a user.

126. The method of embodiment 125, comprising, in accordance with monitoring one or more environmental parameters, adjusting one or more parameters of a cellular microenvironment.

127. The method of any one of embodiments 125-126, wherein the one or more parameters comprises a temperature.

128. The method of any one of embodiments 125-127, wherein the one or more parameters comprises an acidity and/or basicity.

129. The method of any one of embodiments 125-128, wherein the one or more parameters comprises cell confluency.

130. The method of any one of embodiments 124-129, comprising executing, by the microfluidic module, automated exchange of cell culture media.

131. The method of any one of embodiments 124-130, comprising executing, by the microfluidic module, automated trypsinization of cultured cells.

132. The method of any one of embodiments 124-131, comprising executing, by the microfluidic module, automated passaging of cells.

133. A method comprising:
executing an automated cell-based assay and protocol in a multiwell microfluidic-enabled device for a period of at least 24 hours; and
monitoring the automated cell-based assay and protocol in the multiwell microfluidic-enabled device for a period of at least 24 hours.

134. The method of embodiment 133, wherein the assay entails the automated addition of one or more compounds to cells.

135. The methods of any of any one of embodiments 133-134, wherein the assay is a clonogenic assay.

136. The methods of any of any one of embodiments 133-135, wherein the protocol is a transfection protocol.

137. The methods of any of any one of embodiments 133-136, wherein the protocol comprises reprogramming cells to induce pluripotency.

138. The methods of any of any one of embodiments 133-137, wherein the protocol is a protocol to differentiate pluripotent cells.

139. The methods of any of any one of embodiments 133-138, wherein the assay is one of a high-throughput cell based assay, a survival assay, a viral passaging assay, a clonogenic assays beyond oncology, a T-Cell clone, an assay to evaluate therapeutic resistance, or an assay to evaluate therapeutic resistance evolution.

140. The method of any of any one of embodiments 133-139, wherein the assay comprises microscopy measurements.

141. The method of any of any one of embodiments 133-140, wherein the cells comprise one or more of immortalized cells, primary cells, pluripotent cells, pluripotent-derived cells, adherent cells, suspension cells.

142. The method of any of any one of embodiments 133-141, wherein the cells are derived from a clinical sample.

143. The method of any of any one of embodiments 133-142, wherein the assayed cells comprise one or more of a 3D culture model, an organoid model, and a coculture model.

144. The method of any of any one of embodiments 133-143, wherein the assayed cells are reporter cells 145. The method of any of any one of embodiments 133-144, wherein the assayed cells are a library of cells arrayed in the device.

146. The method of any of any one of embodiments 122-145, wherein at least one of the cell culture, assays, and protocols is conducted without tissue culture incubators.

147. The method of any of any one of embodiments 122-146, wherein at least one of the cell culture, assays, or protocols is conducted in a standard laboratory environment.

148. The method of any of any one of embodiments 122-147, wherein at least one of the cell culture, assays, or protocols is conducted in one or more of a field location, a point-of-care, and a pharmacy.

149. A docking station configured to house the device of any one of embodiments 97-121.

150. An ink-jet style input reservoir configured to supply one or more of media and reagents to the device of any one of embodiments 97-121.

151. An output reservoir configured to collect analytes from the device of any one of embodiments 97-121.

152. A manifold configured to connect the device of any one of embodiments 97-121 to one or more of reservoirs, vacuum lines, and other instrumentation.

153. A portable manifold connector/docking module to allow the placement, operation and monitoring of the device of any one of embodiments 97-121 when inserted in standard laboratory equipment such as plate-readers, microscope stages etc.

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of any and all patents and publications referred to in this application are hereby incorporated herein by reference. All references, citations, projects, documents, or other publications mentioned anywhere herein are hereby incorporated by reference in their entirety.

The invention claimed is:

1. A microfluidic-enabled multiwell device for microfluidic control of fluids for cell cultures comprising:

a microfluidics module comprising a well layer, a fluid channels layer, and a pneumatic layer, wherein the well layer is located entirely on a first side of a plane and the fluid channels layer is located entirely on a second side, opposite the first side, of the plane, wherein the microfluidics module comprises a degasser layer comprising a plurality of well-specific degassers each configured to remove gas bubbles from a specific well in the well layer, a gas-permeable degasser membrane between the well layer and the degasser layer, a degasser control layer comprising a plurality of pneumatic channels pneumatically coupled to one or more of the well-specific degassers, and a global degasser configured to remove gas bubbles from a fluid channel configured to deliver fluid to two or more of the wells of the well layer;

a sensor module comprising one or more sensors configured to detect data regarding an environment inside the microfluidic module; and one or more processors; and memory storing instructions configured to be executed by the one or more processors to cause the multiwell device to execute a cell culture process, comprising:

receiving data collected from the one or more sensors regarding the environment inside the microfluidic module; and based at least in part on the data received, causing fluid to flow to an individually addressable well in the multiwell device.

2. The microfluidic-enabled multiwell device of claim 1, wherein the microfluidic-enabled multiwell device further comprises a substrate layer.

3. The microfluidic-enabled multiwell device of claim 1, wherein the pneumatic layer comprises (i) a pneumatic well-selection layer configured to deflect a pneumatic membrane within a pneumatic deflection chamber for a respective well-specific fluidic valve and (ii) pneumatic routing layer comprising one or more pneumatic routing channels configured to connect a primary pneumatic connection port to the pneumatic deflection chamber.

4. The microfluidic-enabled multiwell device of claim 1, further comprising a control module.

5. The microfluidic-enabled multiwell device of claim 1, wherein:

the microfluidics module comprises a plurality of pumps; and causing fluid to flow to an individual well in the multiwell device comprises causing one or more of the plurality of pumps to be actuated.

6. The microfluidic-enabled multiwell device of claim 5, wherein the plurality of pumps comprise one or more of a syringe driven pump, a micro-diaphragm pump, a pneumatic micropump with doormat valve geometry, or a pneumatic micropump with lifting gate valve geometry.

7. The microfluidic-enabled multiwell device of claim 1, wherein the multiwell device comprises one or more microfluidics module sensors integrated into the microfluidic module of the multiwell device, wherein the one or more microfluidics module sensors are configured to detect a characteristic of a parameter of the environment inside the microfluidic module.

8. The microfluidic-enabled multiwell device of claim 1, wherein the sensor layer comprises one or more sensors configured to detect an external characteristic of an environment surrounding the multiwell device.

9. The microfluidic-enabled multiwell device of claim 1, wherein the instructions are configured to be executed by the one or more processors to cause the device to store, in the memory, the data collected from the one or more sensors regarding the environment inside the microfluidic module.

10. The microfluidic-enabled multiwell device of claim 1, wherein the instructions are configured to be executed by the one or more processors to cause the device to transmit, to a remote computing device for storage, the data collected from the one or more sensors regarding the environment inside the microfluidic module.

11. The microfluidic-enabled multiwell device of claim 1, wherein the instructions are configured to be executed by the one or more processors to cause the device to:

transmit instructions for displaying a graphical user interface;

detect an input executed by a user of the device via the graphical user interface; and in response to detecting the input, cause fluid to flow to a user-indicated individual well of the multiwell device.

12. The microfluidic-enabled multiwell device of claim 1, wherein a footprint of the multiwell device conforms to one or more SBS/ANSI multiwell plate standards.

13. The microfluidic-enabled multiwell device of claim 1, wherein the multiwell device is compatible with one of industry-standard laboratory plate-reading and industry-standard automation equipment.

14. The microfluidic-enabled multiwell device of claim 1, wherein one or more of the microfluidic module and the sensor module are configured to be reusable for multiple cell culture procedures.

15. The microfluidic-enabled multiwell device of claim 1, wherein one or more of the microfluidic module and the sensor module are configured to be removable from the multiwell device.

16. The microfluidic-enabled multiwell device of claim 1, wherein one or more of the microfluidic module and the sensor module are configured to be removable from the multiwell device following a first cell culture procedure for replacement by another component prior to a second cell culture procedure.

17. The microfluidic-enabled multiwell device of claim 1, wherein the well layer is configured to be removable from the microfluidics module.

18. The microfluidic-enabled multiwell device of claim 1, wherein the well layer is configured to be removable from the microfluidics module following a first cell culture procedure for replacement by another component prior to a second cell culture procedure.

19. The microfluidic-enabled multiwell device of claim 1, wherein the well layer comprises one or more of glass, cyclo-olefin copolymer, plastics, PDMS, poly-lysine, fibronectin, or matrigel.

20. The microfluidic-enabled multiwell device of claim 1, wherein the well layer is micropatterned.

21. The microfluidic-enabled multiwell device of claim 1, wherein one or more of a material, micropatterning, coating, and geometrical configuration of the well layer are configured for 2D culture of adherent cells.

22. The microfluidic-enabled multiwell device of claim 1, wherein the instructions are configured to be executed by the one or more processors to cause multiwell device to control fluid for the cell culture process for at least 24 hours.

23. The microfluidic-enabled multiwell device of claim 1, wherein causing fluid to flow to an individually addressable well comprises causing a valve to be actuated in association with displacement of a portion of the pneumatic layer.

24. The microfluidic-enabled multiwell device of claim 1, wherein the microfluidic module comprises one or more channels having a diameter of less than 1000 μm.

25. The microfluidic-enabled multiwell device of claim 1, wherein one or more micro-pumps of the microfluidic module are configured to pump a volume of less than 500 nL per pump stroke.

26. The microfluidic-enabled multiwell device of claim 1, comprising an array of 96 or more individually-addressable wells.

27. The microfluidic-enabled multiwell device of claim 1, wherein the instructions are configured to be executed by the one or more processors to cause the microfluidic module to cause automated exchange of cell culture media.

28. The microfluidic-enabled multiwell device of claim 1, wherein the instructions are configured to be executed by the one or more processors to cause the device to execute an automated cell-based assay and protocol in the multiwell device.

29. The microfluidic-enabled multiwell device of claim 28, wherein the executing the assay comprises causing the automated addition of one or more compounds to cells.

30. The microfluidic-enabled multiwell device of claim 28, wherein cells of the assay comprise one or more of immortalized cells, primary cells, pluripotent cells, pluripotent-derived cells, adherent cells, or suspension cells.

31. The microfluidic-enabled multiwell device of claim 28, wherein the assay and protocol is conducted without tissue culture incubators.

32. The microfluidic-enabled multiwell device of claim 1, wherein conducting cell culture comprises one or more of the following:

conducting cell culture without tissue culture incubators;
conducting the cell culture in a laboratory environment;
and conducting the cell culture in one or more of a field location, a point-of-care, and a pharmacy.

33. The microfluidic-enabled multiwell device of claim 1, wherein at the well layer contains cryopreserved cells that are thawed during the cell culture.

34. The microfluidic-enabled multiwell device of claim 1, wherein the instructions are configured to be executed by the one or more processors to cause the device to:

in accordance with receiving the data collected from the one or more sensors regarding the environment inside the microfluidic module, control one or more parameters of an environment inside the microfluidics module, wherein the one or more parameters includes one or more of temperature, pressure, pH, humidity, CO2, O2, confluency, fluid flow, alkalinity, input fluid temperature, output fluid temperature, or ambient light intensity.

35. The microfluidic-enabled multiwell device of claim 1, wherein the instructions are configured to be executed by the one or more processors to cause the device to:

monitor, by the sensor module, one or more parameters of an environment surrounding the multiwell device;

store data regarding the monitoring of the parameters of the environment surrounding the multiwell device on a computer storage of the device; and wirelessly transmit the stored data regarding the monitoring of the parameters of the environment surrounding the multiwell device to a user.

36. The microfluidic-enabled multiwell device of claim 1, wherein the instructions are configured to be executed by the one or more processors to cause the device to:

monitor, by the sensor module, one or more parameters of an environment surrounding the multiwell device;

in accordance with monitoring one or more environmental parameters, adjust one or more parameters of the environment inside the microfluidics module.

37. The microfluidic-enabled multiwell device of claim 1, wherein:

the well layer comprises a first plurality of wells arranged into a plurality of rows;

the fluid channels layer comprises a first input channel and a first output channel both corresponding to a first row of the plurality of rows;

the fluidic channels layer comprises a second input channel and a second output channel both corresponding to a second row of the plurality of rows;

two wells in the first row are individually fluidly connectible to the first input channel by a first plurality of respective input valves;

the two in the first row are individually fluidly connectible to the first output channel by a first plurality of respective output valves;

two wells in the second row are individually fluidly connectible to the second input channel by a second plurality of respective input valves;

the two wells in the second row are individually fluidly connectible to the second output channel by a second plurality of respective output valves.

38. The microfluidic-enabled multiwell device of claim 37, wherein:

the first input channel is fluidly connectible to a common input channel via a first channel input valve;

the first output channel is fluidly connectible to a common output channel via a first channel output valve;

the second input channel is fluidly connectible to the common input channel via a second channel input valve;

the second output channel is fluidly connectible to the common output channel via a second channel output valve.

39. The microfluidic-enabled multiwell device of claim 38, wherein causing fluid to flow to an individually addressable well in the multiwell device comprises:

opening the first channel input valve and the first channel output to allow flow into and out of the first output channel;

opening one of the first plurality of input valves and a corresponding one of the first plurality of output valves to allow flow into and out of the individually addressable well.

40. The microfluidic-enabled multiwell device of claim 37, wherein a micropump is configured to provide vacuum force to selectively cause flow through any individual well of the two wells in the first row and the two wells in the second row.

41. The microfluidic-enabled multiwell device of claim 40, wherein the micropump is downstream from the common output channel.

42. The microfluidic-enabled multiwell device of claim 1, wherein the device is configured to be received by a docking component.

43. The microfluidic-enabled multiwell device of claim 42, wherein the device is configured to be one or more of the following:

fluidly coupled to the docking component;

pneumatically coupled to the docking component; and electronically communicatively coupled to the docking component.

44. A system for microfluidic control of fluids for cell cultures, wherein the system comprises:

the microfluidic-enabled multiwell device of claim 1; and a docking component configured to receive the multiwell device and to be fluidly coupled to the multiwell device.

45. The system of claim 44, wherein the docking component is configured to be one or more of the following:

pneumatically coupled to the device; and electronically communicatively coupled to the device.

46. The system of claim 44, wherein the docking component comprises one or more of the following:

a tabletop docking station;

a portable docking module configured to enable operation of the multiwell device when the portable docking module is inserted in one or more of a plate reader or a microscope stage;

a display configured to display a graphical user interface; and a user input device configured to receive a user input comprising an instruction.

47. The system of claim 44, comprising an inkjet input reservoir system configured to be fluidly coupled to the multiwell device and to supply one or more of media, cell suspension, and reagents to the multiwell device.

48. The system of claim 44, comprising an output reservoir configured to be fluidly coupled to the multiwell device and to receive flow of one or more of media, cell suspension, and reagents from the multiwell device.

49. The system of claim 44, comprising a manifold configured to attach to one or more of a reservoir or a vacuum line.

* * * * *